(12) United States Patent
Li et al.

(10) Patent No.: US 12,319,722 B2
(45) Date of Patent: Jun. 3, 2025

(54) INTERLEUKIN-15 (IL-15) FUSION PROTEINS AND USES THEREOF

(71) Applicant: Cugene Inc, Waltham, MA (US)

(72) Inventors: Yue-Sheng Li, Thousand Oaks, CA (US); Lingyun Rui, Weston, MA (US); Jing Xu, Waltham, MA (US)

(73) Assignee: Cugene Inc, Waltham, MA (US)

( * ) Notice: Subject to any disclaimer, the term of this patent is extended or adjusted under 35 U.S.C. 154(b) by 249 days.

(21) Appl. No.: 17/254,004

(22) PCT Filed: Jun. 20, 2019

(86) PCT No.: PCT/US2019/038210
§ 371 (c)(1),
(2) Date: Dec. 18, 2020

(87) PCT Pub. No.: WO2019/246379
PCT Pub. Date: Dec. 26, 2019

(65) Prior Publication Data
US 2022/0106374 A1   Apr. 7, 2022

Related U.S. Application Data

(60) Provisional application No. 62/689,051, filed on Jun. 22, 2018.

(51) Int. Cl.
| | | |
|---|---|---|
| C07K 14/54 | (2006.01) | |
| A61P 35/00 | (2006.01) | |
| C07K 14/715 | (2006.01) | |
| A61K 38/00 | (2006.01) | |
| C07K 1/14 | (2006.01) | |

(52) U.S. Cl.
CPC .......... *C07K 14/5443* (2013.01); *A61P 35/00* (2018.01); *C07K 14/7155* (2013.01); *A61K 38/00* (2013.01); *C07K 1/14* (2013.01); *C07K 2319/30* (2013.01); *C07K 2319/33* (2013.01)

(58) Field of Classification Search
CPC .. C07K 14/5443; C07K 2319/30; A61P 35/00
See application file for complete search history.

(56) References Cited

U.S. PATENT DOCUMENTS

| | | |
|---|---|---|
| 9,328,159 B2 | 5/2016 | Wong et al. |
| 9,428,573 B2 | 8/2016 | Wong et al. |
| 9,493,533 B2 | 11/2016 | Bernard et al. |
| 10,206,980 B2 | 2/2019 | Qu et al. |
| 10,265,382 B2 | 4/2019 | Felber et al. |
| 10,335,460 B2 | 7/2019 | Felber et al. |
| 10,550,185 B2 | 2/2020 | Bernett et al. |
| 10,611,812 B2 | 4/2020 | Wang et al. |
| 2006/0236411 A1 | 10/2006 | Dreher et al. |
| 2006/0257361 A1 | 11/2006 | Watanabe et al. |
| 2009/0238791 A1 | 9/2009 | Jacques et al. |
| 2014/0120096 A1 | 5/2014 | Bakker et al. |
| 2016/0355567 A1 | 12/2016 | Wong et al. |
| 2019/0209653 A1 | 7/2019 | Felber |
| 2021/0106655 A1 | 4/2021 | Qu |

FOREIGN PATENT DOCUMENTS

| | | |
|---|---|---|
| EP | 3093295 | 11/2016 |
| WO | 1998050431 | 12/1998 |
| WO | 2014066527 | 5/2014 |
| WO | 2017046200 | 3/2017 |
| WO | 2019006472 | 1/2019 |

OTHER PUBLICATIONS

Guo et al. Immunobiology of the IL-15/IL-15Ralpha complex as an antitumor and antiviral agent. Cytokine & Growth Factor Reviews, 38:10-21 (Sep. 1, 2017).
Chirifu M et al. Crystal structure of the IL-15-IL-15Ra complex, a cytokine-receptor unit presented in trans. Nature Immunol. 8(9): 1001-1007 (2007).
Hezareh M et al. Effector Function Activities of a Panel of Mutants of a Broadly Neutralizing Antibody against Human Immunodeficiency Virus Type 1. J Virol 75: 12161-8 (2001).
Hu Q et al. Discovery of a novel IL-15 based protein with improved developability and efficacy for cancer immunotherapy. Scientific Reports 8:7675 (2018).
Mortier E et al. Soluble Interleukin-15 Receptor a (IL-15Rα)-sushi as a Selective and Potent Agonist of IL-15 Action through IL-15Rβ/γ. J Biol Chem 281:1612-1619 (2006).
NG SSM et al. Heterodimeric IL-15 Treatment Enhances Tumor Infiltration, Persistence and Effector Functions of Adoptively Transferred Tumor-specific T Cells in the Absence of Lymphodepletion. Clin Cancer Res 23(11): 2817-30 (2016).
Ring AM et al. Mechanistic and structural insight into the functional dichotomy between interleukin-2 and interleukin-15. Nat Immunol 13(12): 1187-1195 (2012).

(Continued)

*Primary Examiner* — Gyan Chandra
(74) *Attorney, Agent, or Firm* — Craig A Crandall, APC; Craig A Crandall

(57) ABSTRACT

The present disclosure provides novel and improved IL-15 fusion proteins for use in the treatment of cancer and other disorders. In various embodiments, the fusion proteins of the invention have two functional domains: an IL-15/IL-15RαSushi domain (also referred to herein as an "IL-15/IL-15RαSushi complex") and an Fc domain, each of which can take different forms, and configured such that the IL-15 is fused to the C-terminal of the Fc domain and co-expressed and non-covalently complexed with IL-15RαSushi. Importantly, the fusions proteins of the present invention address several of the limitations observed with the IL-15 therapeutics evaluated to date; specifically, the fusion proteins demonstrate extended the half-life of IL-15 in vivo, and demonstrate superior preclinical activity compared to rIL-15 or related cytokine therapeutics.

12 Claims, 30 Drawing Sheets

Specification includes a Sequence Listing.

(56) References Cited

OTHER PUBLICATIONS

Shields RL et al. High resolution mapping of the binding site on human IgG1 for Fc gamma RI, Fc gamma RII, Fc gamma RIII and FcRn and design of IgG1 variants with improved binding to the Fc gamma R. J Biol Chem 276(9):6591-604 (2001).
Spangler JB et al. Insights into Cytokine-Receptor Interactions from Cytokine Engineering. Annu Rev Immunol 33: 139-167 (2015).
Steel JC et al. Interleukin-15 biology and its therapeutic implications in cancer. Trends Pharmacol Sci 33(1): 35-41 (2012).
Vincent M et al. Antitumor activity of an immunocytokine composed of an anti-GD2 antibody and the IL-15 superagonist RLI. OncoImmunology 2:11, e26441 (2013).
Wrangle JM et al. ALT-803, an IL-15 superagonist, in combination with nivolumab in patients with metastatic non-small cell lung cancer: a non-randomised, open-label, phase 1b trial. Lancet Oncol 19: 694-704 (2018).
Xu W et al. Efficacy and Mechanism-of-Action of a Novel Superagonist Interleukin-15: Interleukin-15 Receptor α/Fc Fusion Complex in Syngeneic Murine Models of Multiple Myeloma. Cancer Res 73(10); 3075-86 (2013).
PCT International Search Report-Written Opinion, Oct. 2, 2019.

FIG. 1A - IL-15/IL-15Rα heterodimeric Fc fusion format
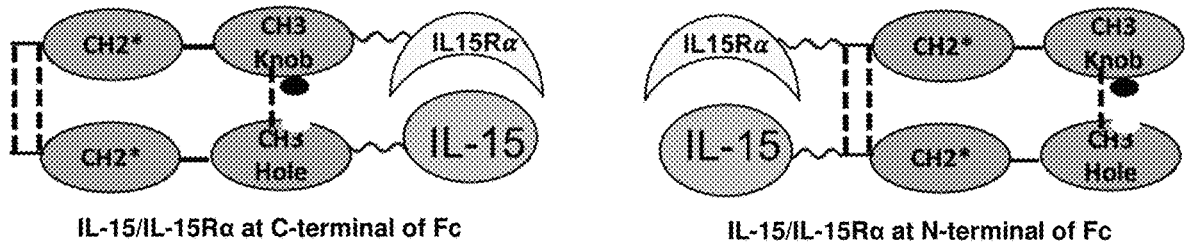
IL-15/IL-15Rα at C-terminal of Fc        IL-15/IL-15Rα at N-terminal of Fc
FIG. 1B - Monovalent IL-15/IL-15Rα (non-covalent) Fc fusion format
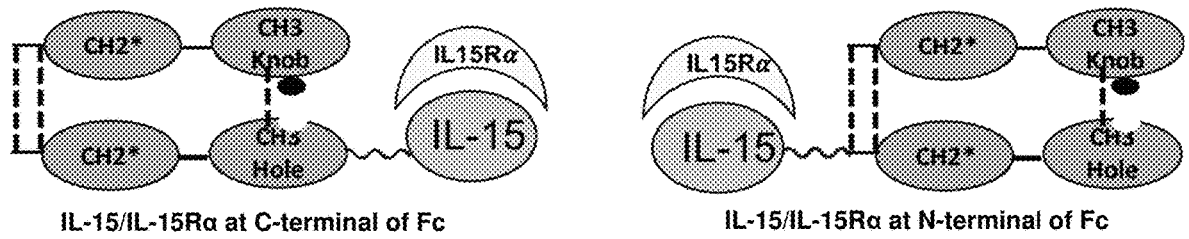
IL-15/IL-15Rα at C-terminal of Fc        IL-15/IL-15Rα at N-terminal of Fc
FIG. 1C - Bivalent IL-15/IL-15Rα (non-covalent) Fc fusion format
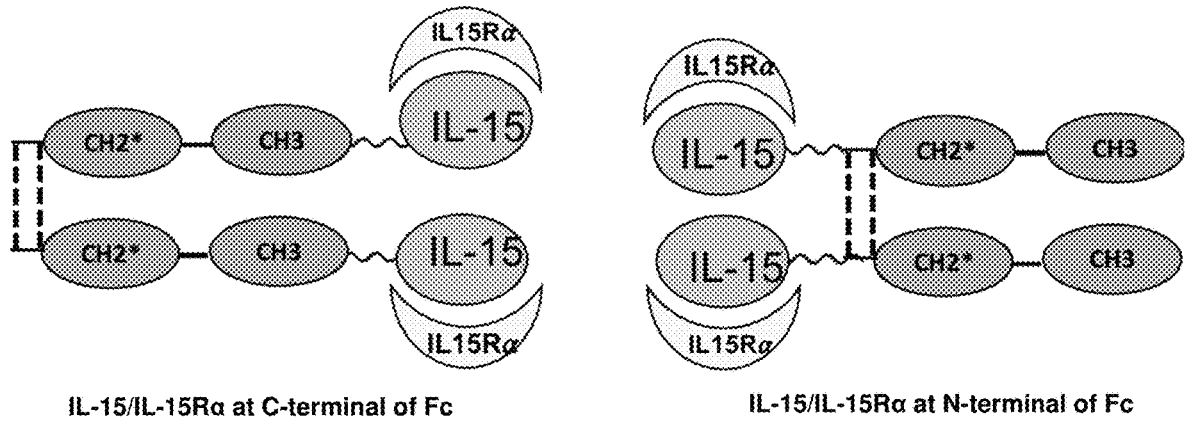
IL-15/IL-15Rα at C-terminal of Fc        IL-15/IL-15Rα at N-terminal of Fc FIG. 1D - Monovalent IL-15 (non-covalent)/IL-15Rα Fc fusion format
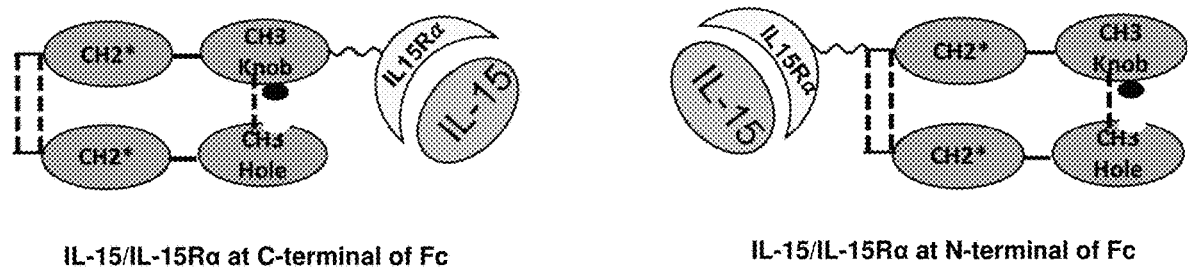
IL-15/IL-15Rα at C-terminal of Fc  IL-15/IL-15Rα at N-terminal of Fc
FIG. 1E - Bivalent IL-15 (non-covalent)/IL-15Rα Fc fusion format
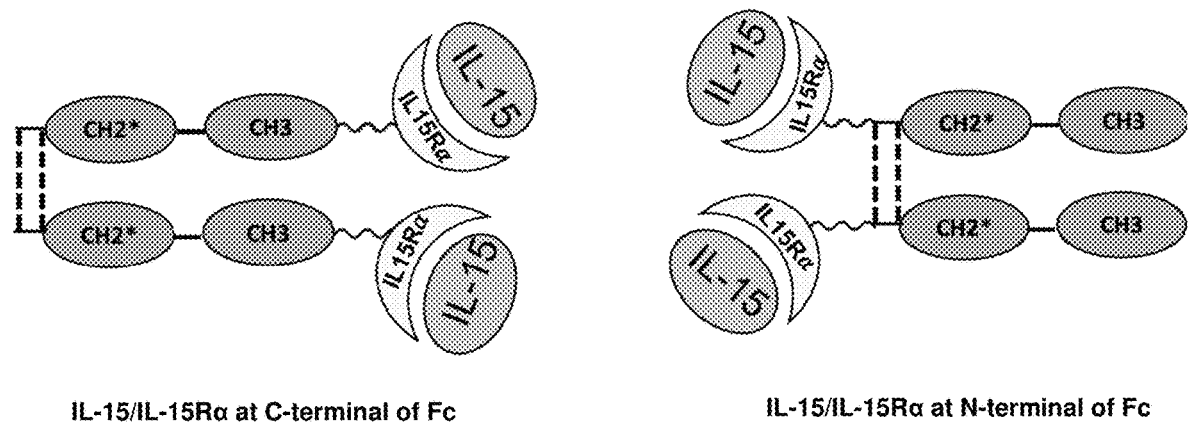
IL-15/IL-15Rα at C-terminal of Fc  IL-15/IL-15Rα at N-terminal of Fc

INTERLEUKIN-15 (IL-15) FUSION PROTEINS AND USES THEREOF

RELATED PATENT APPLICATIONS

This application is a U.S. National Stage Application pursuant to 35 U.S.C. § 371 of PCT/US2019/038210, filed Jun. 20, 2019, which claims benefit of U.S. Provisional Application No. 62/689,051, filed on Jun. 22, 2018, each incorporated in its entirety by reference herein.

BACKGROUND

While cancer has been traditionally treated by chemotherapy, radiation, targeted therapies and surgery, a fifth pillar of cancer treatment, immunotherapy, has emerged over the past 10 years and revolutionized the war on cancer. The benchmark for the immunotherapy drugs has been established by the development of T cell checkpoint (CTLA-4 and PD-1/PD-L1) inhibitors. It has been demonstrated that these therapies effectively expand and reactivate the pool of tumor-specific T cells leading to objective response rates of up to 50% in patients with certain cancers.

Recently, interleukin-15 (IL-15), a member of the four α-helix bundle family of cytokines, has emerged as a candidate immunomodulator for the treatment of cancer. IL-15 binds to its specific receptor, IL-15Rα, which is expressed on antigen-presenting dendritic cells, monocytes and macrophages, and trans-activates a heterodimeric receptor complex composed of IL-15Rβ and the common cytokine receptor γ chain ($γ_c$) on the responding cells, including T and natural killer (NK) cells, to initiate signaling. IL-15 exhibits broad activity and induces the differentiation and proliferation of T, B and natural killer (NK) cells. It also enhances the cytolytic activity of $CD8^+$ T cells and induces long-lasting antigen-experienced $CD8^+CD44^{hi}$ memory T cells. IL-15 stimulates differentiation and immunoglobulin synthesis by B cells and induces maturation of dendritic cells. It does not stimulate immunosuppressive T regulatory cells (Tregs). As such, it was hypothesized that boosting IL-15 activity could enhance innate and adaptive immunity and fight tumors, making it a promising agent for anticancer therapy (Steel et al., Trends in Pharmacological Sciences, 33(1):35-41, 2012).

In a first-in-human phase I clinical trial of intravenous infusions of recombinant human IL-15 in patients with metastatic malignant melanoma, it was reported that IL-15 could be safely administered to patients with metastatic malignancy and that IL-15 administration markedly altered homeostasis of lymphocyte subsets in blood, with NK cells and γδ cells most dramatically affected, followed by CD8 memory T cells (Conlon et al, J Clin Oncol., 33(1), 74-82).

Despite these new advancements using IL-15 as a cancer immunotherapeutic to augment immune responses, there remain limitations to the effective use of IL-15 as a therapeutic. For example, IL-15 has a short half-life (<40 minutes) resulting in 1) low bioavailability that impedes its in vivo antitumor effects and 2) the requirement for administration of a high dose to achieve therapeutic relevant exposure, which results in toxicity. In addition, it is understood that IL-15 has poor expression levels in standard mammalian cell systems.

There remains a critical need to provide novel therapeutics which are both highly effective and safe for the treatment of cancer.

DISCLOSURE OF THE INVENTION

In one aspect, the present invention provides novel and improved IL-15 fusion proteins for use in the treatment of cancer. In various embodiments, the fusion proteins of the present invention have two functional domains: an IL-15/IL-15Receptor α (IL-15Rα) component (also referred to herein as an "IL-15/IL-15Rα complex") and an Fc domain, each of which can take different forms. In various embodiments, the fusion proteins are configured such that the IL-15 is fused to either the C-terminal of the Fc domain or to the N-terminal of the Fc domain and co-expressed and non-covalently complexed with an IL-15Rα domain (see FIGS. 1B and 10).

In various embodiments, the IL-15 fusion proteins of the present invention comprise an IL-15/IL-15Rα complex wherein the IL-15 domain comprises the sequence of the mature human IL-15 polypeptide (also referred to herein as huIL-15 or IL-15 wild type (wt)) as set forth in SEQ ID NO: 2. In various embodiments, the IL-15 domain will be an IL-15 variant (or mutant) comprising a sequence derived from the sequence of the mature human IL-15 polypeptide as set forth in SEQ ID NO: 2. Variants (or mutants) of IL-15 are referred to herein using the native amino acid, its position in the mature sequence and the variant amino acid. For example, huIL-15 "S58D" refers to human IL-15 comprising a substitution of S to D at position 58 of SEQ ID NO: 2. In various embodiments, the IL-15 variant functions as an IL-15 super-agonist as demonstrated by, e.g., increased binding activity for the IL-15Rβ and increased functional activity compared to the native IL-15 polypeptide. In various embodiments, the IL-15 variant functions as an IL-15 antagonist as demonstrated by e.g., binding activity for the IL-15Rβ but no functional activity compared to the native IL-15 polypeptide. In various embodiments, the IL-15 variant has increased binding affinity or a decreased binding activity for the IL-15Rβγc receptors compared to the native IL-15 polypeptide. In various embodiments, the sequence of the IL-15 variant has at least one (i.e., 1, 2, 3, 4, 5, 6, 7, 8, 9, 10, or more) amino acid change compared to the native IL-15 sequence. The amino acid change can include one or more of an amino acid substitution, deletion, or insertion in the domain of IL-15 that interacts with IL-15Rβ and/or IL-15R$γ_c$ and/or IL-15Rβ$γ_c$. In various embodiments, the amino acid change is one or more amino acid substitutions or deletions at position 30, 31, 32, 58, 62, 63, 67, 68, or 108 of SEQ ID NO: 2. In various embodiments, the amino acid change is the substitution of D to T at position 30, V to Y at position 31, H to E at position 32, S to D at position 58, T to D at position 62, V to F at position 63, I to V at position 67, I to F or H or D or K at position 68, or Q to A or M or S at position 108 of the mature human IL-15 sequence, or any combination of these substitutions. In various embodiments, the amino acid change is the substitution of S to D at position 58 of the mature human IL-15 sequence. In various embodiments, the IL-15 polypeptide comprises an IL-15 variant comprising an S58D mutation of SEQ ID NO: 2.

In various embodiments, the IL-15 fusion proteins of the present invention comprise an IL-15/IL-15Rα complex wherein the IL-15Rα comprises either IL-15RαSushi domain (SEQ ID NO: 5) or IL-15Rα extracellular domain (SEQ ID NO: 4) or any binding functional domain of IL-15Rα. In various embodiments, the IL-15Rα domain comprises a sequence that is at least 90% to the sequence set forth in SEQ ID NO: 4. In various embodiments the IL-15Rα domain comprises a sequence that is at least 95% to the sequence set forth in SEQ ID NO: 4. In various embodiments, the IL-15Rα domain is an IL-15RαSushi domain which comprises a sequence that is at least 90% to the sequence set forth in SEQ ID NO: 5. In various embodiments the IL-15RαSushi domain comprises a sequence that is at least 95% to the sequence set forth in SEQ ID NO: 5.

In various embodiments, the IL-15 fusion proteins of the present invention comprise an IL-15/IL-15RαSushi complex and at least one heterologous protein.

In various embodiments, the IL-15 fusion proteins of the present invention comprise an IL-15/IL-15Rα complex wherein the IL-15 is fused to either the C-terminus, or N-terminus of the heterologous protein.

In various embodiments, the IL-15 fusion proteins of the present invention contain an IL-15/IL-15Rα-heterologous protein complex either in dimeric or monomeric format.

In various embodiments, the heterologous protein is an Fc domain (or functional fragment thereof). In various embodiments, the Fc domain is selected from the group consisting of human IgG1 Fc domain, human IgG2 Fc domain, human IgG3 Fc domain, human IgG4 Fc domain, IgA Fc domain, IgD Fc domain, IgE Fc domain, IgG Fc domain and IgM Fc domain; or any combination thereof. In various embodiments, the Fc domain includes an amino acid change that results in an Fc domain having altered complement or Fc receptor binding properties. Amino acid changes to produce an Fc domain with altered complement or Fc receptor binding properties are known in the art. In various embodiments, the Fc domain sequence used to make dimeric IL-15/IL-15Rα complex-Fc fusion proteins is the human IgG1-Fc domain sequence set forth in SEQ ID NO: 6. SEQ ID NO: 6 contains amino acid substitutions that ablate FcγR and C1q binding. In various embodiments, the heterodimeric Fc domain sequence used to make monovalent IL-15/IL-15Rα complex-Fc fusion proteins is the Knob-Fc domain sequence set forth in SEQ ID NO: 7. SEQ ID NO: 7 contains amino acid substitutions that ablate FcγR and C1q binding. In various embodiments, the heterodimeric Fc domain sequence used to make monovalent IL-15/IL-15Rα complex-Fc fusion proteins is the Hole-Fc domain sequence set forth in SEQ ID NO: 8. SEQ ID NO: 8 contains amino acid substitutions that ablate FcγR and C1q binding.

In various embodiments, the IL-15 fusion proteins of the present invention comprise an IL-15/IL-15Rα complex and the heterologous protein is a full-length non-binding Ab for half-life extension or is a specific antibody or fragment used for targeting, multifunction, and half-life extension.

In various embodiments, the IL-15 fusion proteins of the present invention comprise an IL-15/IL-15Rα complex and the heterologous protein is an Ab either in full-length IgG or antibody fragment format (monospecific or bispecific) and provides additive or synergistic effect with IL-15/IL-15RαSushi complex.

In various embodiments, the IL-15 fusion proteins of the present invention comprise an IL-15/IL-15Rα complex and the heterologous protein provides tissue- or tumor-specific targeting to increase IL-15 local concentration and penetration into the tumor microenvironment and to increase tumor cell-killing efficacy and reduce systemic toxicity.

In various embodiments, the heterologous protein is covalently linked to IL-15 polypeptide (or functional fragment thereof) of the IL-15/IL-15RαSushi complex by polypeptide linker sequence. In various embodiments, the linker may be an artificial sequence of between 5, 10, 15, 20, 30, 40 or more amino acids that are relatively free of secondary structure. In various embodiments, the linker is rich in G/S content (e.g., at least about 60%, 70%, 80%, 90%, or more of the amino acids in the linker are G or S). In various embodiments, the linker is selected from the group of sequences set forth in SEQ ID NOs: 9-12. Each peptide linker sequence can be selected independently.

In another aspect, the present disclosure provides a pharmaceutical composition comprising the isolated IL-15 fusion proteins of the present invention in admixture with a pharmaceutically acceptable carrier.

In another aspect, the present disclosure provides a method for treating cancer or cancer metastasis in a subject, comprising administering a therapeutically effective amount of the pharmaceutical compositions of the invention to a subject in need thereof. In one embodiment, the subject is a human subject. In various embodiments, the cancer is selected from pancreatic cancer, gastric cancer, liver cancer, breast cancer, ovarian cancer, colorectal cancer, melanoma, leukemia, myelodysplastic syndrome, lung cancer, prostate cancer, brain cancer, bladder cancer, head-neck cancer, or rhabdomyosarcoma.

In another aspect, the present disclosure provides a method for treating cancer or cancer metastasis in a subject, comprising administering a therapeutically effective amount of the pharmaceutical compositions of the invention in combination with a second therapy selected from the group consisting of: cytotoxic chemotherapy, immunotherapy, small molecule kinase inhibitor targeted therapy, surgery, radiation therapy, stem cell transplantation, cell therapies including CAR-T cell, CAR-NK cell, iPS-induced NK cell, iPS-induced CAR-NK cell, iPS-induced T cell, iPS-induced CAR-T cell or TCR-T cell, and vaccine such as Bacille Calmette-Guerine (BCG). In various embodiments, the combination therapy may comprise administering to the subject a therapeutically effective amount of immunotherapy, including, but are not limited to, treatment using depleting antibodies to specific tumor antigens; treatment using antibody-drug conjugates; treatment using agonistic, antagonistic, or blocking antibodies to co-stimulatory or co-inhibitory molecules (immune checkpoints) such as CD276, CD272, CTLA-4, PD-1, PD-L1, CD40, SIRPa, CD47, OX-40, CD137, GITR, LAGS, ICOS, CD27, 4-1BB, TIM-3, B7-H4, Siglec 7, Siglec 8, Siglec 9, Siglec 15 and VISTA; treatment using bispecific T cell engaging antibodies (BiTE®) such as blinatumomab: treatment involving administration of biological response modifiers such as IL-2, IL-7, IL-10, IL-12, IL-21, G-CSF, GM-CSF, IFN-α, IFN-8 and IFN-γ; treatment using therapeutic vaccines such as sipuleucel-T; treatment using dendritic cell vaccines, or tumor antigen peptide vaccines; treatment using chimeric antigen receptor (CAR)-T cells; treatment using CAR-NK cells; treatment using tumor infiltrating lymphocytes (TILs); treatment using adoptively transferred anti-tumor T cells (ex vivo expanded and/or TCR transgenic T-cells); treatment using TALL-104 cells; and treatment using immunostimulatory agents such as Toll-like receptor (TLR) agents such as TLR4, TLR7, TLR8, TLR9 agonists CpG and imiquimod; and treatment using vaccine such as Bacille Calmette-Guerine (BCG); wherein the combination therapy provides increased effector cell killing of tumor cells, i.e., a synergy exists between the IL-15/IL-15RαSushi-Fc fusion proteins and the immunotherapy when co-administered.

In another aspect, the present disclosure provides a method to expand and renew NK cells and T cells in vitro and in vivo and in combination with any adoptive transfer NK and T cell therapy or CAR-NK and CAR-T therapy to sustain cell survival and half-life.

In another aspect, the present disclosure provides a method for treating a viral infection in a subject, comprising administering a therapeutically effective amount of the pharmaceutical compositions of the invention to a subject in need thereof. In one embodiment, the subject is a human subject.

In another aspect, the disclosure provides uses of the IL-15 fusion proteins for the preparation of a medicament for the treatment of cancer.

In another aspect, the disclosure provides uses of the IL-15 fusion proteins for the preparation of a medicament for the treatment of a viral infection.

In another aspect, the present disclosure provides isolated nucleic acid molecules comprising a polynucleotide encoding an IL-15 fusion protein of the present disclosure. In various embodiments, the isolated nucleic acid molecules comprise the polynucleotides described herein, and further comprise a polynucleotide encoding at least one heterologous protein described herein. In various embodiments, the nucleic acid molecules further comprise polynucleotides encoding the linkers described herein. In various embodiments, the nucleic acid molecules comprise the nucleotide sequences set forth in SEQ ID NOs: 56-63.

In another aspect, the present disclosure provides vectors comprising the nucleic acids described herein. In various embodiments, the vector is an expression vector. In another aspect, the present disclosure provides isolated cells comprising the nucleic acids of the disclosure. In various embodiments, the cell is a host cell comprising the expression vector of the disclosure. In another aspect, methods of making the IL-15 fusion proteins are provided by culturing the host cells under conditions promoting expression of the proteins or polypeptides.

BRIEF DESCRIPTION OF THE FIGURES

FIG. 1 depicts several formats for the IL-15/IL-15Rα-Fc fusion proteins of the present invention. (A) IL-15/IL-15Rα heterodimeric Fc fusion format. (B) Monovalent IL-15/IL-15Rα (non-covalent) Fc fusion format. (C) Bivalent IL-15/IL-15Rα (no-covalent) Fc fusion format; (D) Monovalent IL-15 (non-covalent)/IL-15Rα Fc fusion protein format. (E) Bivalent IL-15 (non-covalent)/IL-15Rα Fc fusion protein format. For each fusion protein format, the IL-15/IL-15Rα complex can be at either the C-terminus or N-terminus of the Fc domain; and IL-15Rα can be either IL-15RαSushi domain or IL-15RαECD.

MODE(S) FOR CARRYING OUT THE DISCLOSURE

Figure 2A:
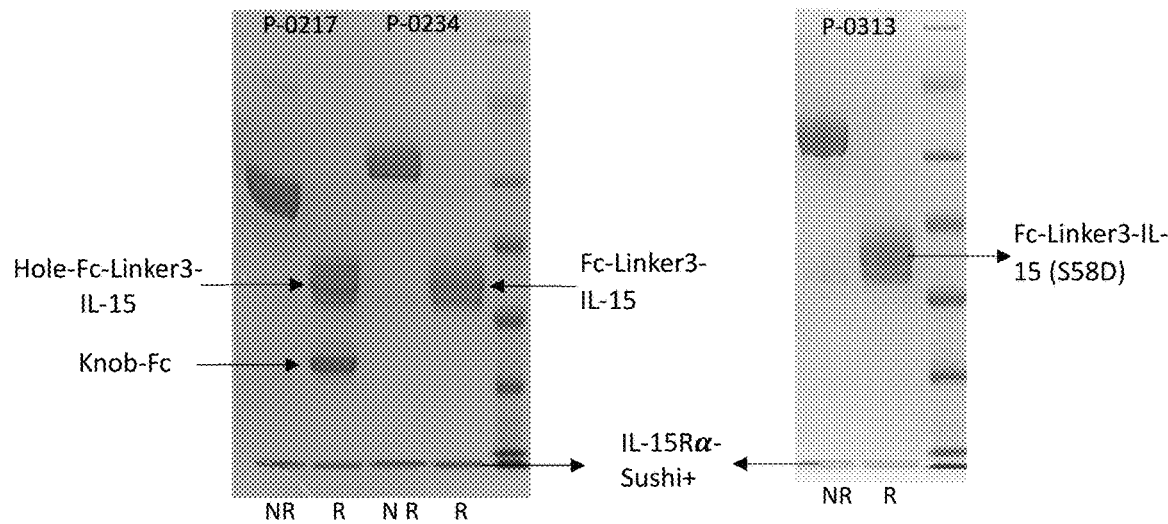
FIG. 2 depicts A) the purity and B) monomer percentage of illustrative IL-15/IL-15Rα (non-covalent)-Fc fusion proteins, P-0217, P-0234, and P-0313, as determined by SDS-PAGE and SEC-HPLC, respectively. All the three fusion proteins comprise IL-15/IL-15Rα complex at the C-terminus. P-0217 is a monovalent IL-15/IL-15Rα (non-covalent) Fc fusion, P-0234 is the dimeric counterpart of P-0217, and P-0313 shares the same fusion configuration as P-0234 but differs only with S58D substitution in the IL-15 domain.

The present disclosure provides novel and improved IL-15 fusion proteins for use in the treatment of cancer and other disorders. In various embodiments, the fusion proteins of the invention have two functional domains: an IL-15/IL-15RαSushi domain (also referred to herein as an "IL-15/IL-15RαSushi complex") and an Fc domain, each of which can take different forms, and configured such that the IL-15 is fused to the C-terminal or N-terminal of the Fc domain, and co-expressed and non-covalently complexed with IL-15Rα, IL-15RαSushi or IL-15RαECD (see FIG. 1).

The present disclosure provides IL-15 variants with amino acid substitution, deletion, insertion and to functions as an IL-15 super-agonist or antagonist for use in the treatment of cancer and other disorders.

The present inventors understood that to extend the circulating half-life of IL-15 or IL-15 fusion protein and/or to increase its biological activity, it is highly desirable to covalently link IL-15 to Fc portion of the human IgG either at the N-terminus or C-terminus to enhance the presentation of IL-15 to its signaling receptors and to prevent the disassociation of IL-15 from the fusion protein and to limit the peak serum concentration of free IL-15 which is commonly associated with side effects of free human IL-15. The present inventors further believed that it was highly desirable to create fusion protein complexes containing the IL-15Rα domain non-covalently bound to IL-15 to more naturally present IL-15 to it's signaling receptors. Using the format of the present invention, the present inventors demonstrate that you can increase protein expression, reduce immunogenicity and protect IL-15 degradation. In various embodiments disclosed or described in this invention, it is preferable to place the IL-15-IL-15Rα complex at the C-terminus in a dimeric format to achieve enhanced biological activity, and developability such as increased expression and low aggregation. Importantly, the fusions proteins of the present invention address several of the limitations observed with the IL-15 therapeutics evaluated to date; specifically, the fusion proteins demonstrate extended the half-life of IL-15 in vivo, and demonstrate superior preclinical activity compared to rIL-15 or related cytokine therapeutics.

Definitions

The terms "polypeptide", "peptide" and "protein" are used interchangeably herein to refer to a polymer of amino acid residues. In various embodiments, "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (amino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to, peptide mimetics such as amino acids joined by an ether as opposed to an amide bond Polypeptides of the disclosure include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (5) confer or modify other physicochemical or functional properties. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" refers to the substitution in a polypeptide of an amino acid with a functionally similar amino acid. The following six groups each contain amino acids that are conservative substitutions for one another:
1) Alanine (A), Serine (S), and Threonine (T)
2) Aspartic acid (D) and Glutamic acid (E)
3) Asparagine (N) and Glutamine (Q)
4) Arginine (R) and Lysine (K)
5) Isoleucine (I), Leucine (L), Methionine (M), and Valine (V)
6) Phenylalanine (F), Tyrosine (Y), and Tryptophan (W)

A "non-conservative amino acid substitution" refers to the substitution of a member of one of these classes for a member from another class. In making such changes, according to various embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in various embodiments, the substitution of amino acids whose hydropathic indices are within +2 is included. In various embodiments, those that are within +1 are included, and in various embodiments, those within +0.5 are included.

It is also understood in the art that the substitution of like amino acids can be made effectively on the basis of hydrophilicity, particularly where the biologically functional protein or peptide thereby created is intended for use in immunological embodiments, as disclosed herein. In various embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in various embodiments, the substitution of amino acids whose hydrophilicity values are within +2 is included, in various embodiments, those that are within +1 are included, and in various embodiments, those within +0.5 are included.

Exemplary amino acid substitutions are set forth in Table 1.

TABLE 1

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | |
| Asp | Glu | |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of polypeptides as set forth herein using well-known techniques. In various embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, the skilled artisan can predict the importance of amino acid residues in a polypeptide that correspond to amino acid residues important for activity or structure in similar polypeptides. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of a polypeptide with respect to its three-dimensional structure. In various embodiments, one skilled in the art may choose to not make radical changes to amino acid residues predicted to be on the surface of the polypeptide, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

The term "polypeptide fragment" and "truncated polypeptide" as used herein refers to a polypeptide that has an amino-terminal and/or carboxy-terminal deletion as compared to a corresponding full-length protein. In certain embodiments, fragments can be, e.g., at least 5, at least 10, at least 25, at least 50, at least 100, at least 150, at least 200, at least 250, at least 300, at least 350, at least 400, at least 450, at least 500, at least 600, at least 700, at least 800, at least 900 or at least 1000 amino acids in length. In certain embodiments, fragments can also be, e.g., at most 1000, at most 900, at most 800, at most 700, at most 600, at most 500, at most 450, at most 400, at most 350, at most 300, at most 250, at most 200, at most 150, at most 100, at most 50, at most 25, at most 10, or at most 5 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

The terms "polypeptide variant", "hybrid polypeptide" and "polypeptide mutant" as used herein refers to a polypeptide that comprises an amino acid sequence wherein one or more amino acid residues are inserted into, deleted from and/or substituted into the amino acid sequence relative to another polypeptide sequence. In certain embodiments, the number of amino acid residues to be inserted, deleted, or substituted can be, e.g., at least 1, at least 2, at least 3, at least 4, at least 5, at least 10, at least 25, at least 50, at least 75, at least 100, at least 125, at least 150, at least 175, at least 200, at least 225, at least 250, at least 275, at least 300, at least 350, at least 400, at least 450 or at least 500 amino acids in length. Hybrids of the present disclosure include fusion proteins.

A "derivative" of a polypeptide is a polypeptide that has been chemically modified, e.g., conjugation to another chemical moiety such as, for example, polyethylene glycol, albumin (e.g., human serum albumin), phosphorylation, and glycosylation.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm and means that a given sequence is at least 80% identical to another length of another sequence. In certain embodiments, the % identity is selected from, e.g., at least 60%, at least 65%, at least 70%, at least 75%, at least 80%, at least 85%, at least 90%, at least 95%, or at least 99% or more sequence identity to a given sequence. In certain embodiments, the % identity is in the range of, e.g., about 60% to about 70%, about 70% to about 80%, about 80% to about 85%, about 85% to about 90%, about 90% to about 95%, or about 95% to about 99%.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. In certain embodiments, the % homology is selected from, e.g., at least 60%, at least 65%, at least 70%, at least 75%, at least 80%, at least 85%, at least 90%, at least 95%, or at least 99% or more sequence homology to a given sequence. In certain embodiments, the % homology is in the range of, e.g., about 60% to about 70%, about 70% to about 80%, about 80% to about 85%, about 85% to about 90%, about 90% to about 95%, or about 95% to about 99%.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., J. Mol. Biol. 215:403-10, 1990 (with special reference to the published default setting, i.e., parameters w=4, t=17) and Altschul et al., Nucleic Acids Res., 25:3389-3402, 1997. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See Id.

In addition to calculating percent sequence identity, the BLAST algorithm also performs a statistical analysis of the similarity between two sequences (see, e.g., Karlin & Altschul, Proc. Nat'l. Acad. Sci. USA, 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is, e.g., less than about 0.1, less than about 0.01, or less than about 0.001.

The term "heterologous" as used herein refers to a composition or state that is not native or naturally found, for example, that may be achieved by replacing an existing natural composition or state with one that is derived from another source. Similarly, the expression of a protein in an organism other than the organism in which that protein is naturally expressed constitutes a heterologous expression system and a heterologous protein.

The term "antibody" as used herein refers to a protein comprising one or more polypeptides substantially or partially encoded by immunoglobulin genes or fragments of immunoglobulin genes and having specificity to a tumor antigen or specificity to a molecule overexpressed in a pathological state. The recognized immunoglobulin genes include the kappa, lambda, alpha, gamma, delta, epsilon and mu constant region genes, as well as subtypes of these genes and myriad of immunoglobulin variable region genes. Light chains (LC) are classified as either kappa or lambda. Heavy chains (HC) are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition.

The term "Fc region" as used herein defines the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain and a CH3 domain, and optionally comprises a CH4 domain. The Fc portion of an antibody mediates several important effector functions e.g. cytokine induction, ADCC, phagocytosis, complement dependent cytotoxicity (CDC) and half-life/clearance rate of antibody and antigen-antibody complexes (e.g., the neonatal FcR (FcRn) binds to the Fc region of IgG at acidic pH in the endosome and protects IgG from degradation, thereby contributing to the long serum half-life of IgG). Replacements of amino acid residues in the Fc portion to alter antibody effector function are known in the art (see, e.g., Winter et al., U.S. Pat. Nos. 5,648,260 and 5,624,821).

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is substantially identical to the nucleotide sequence of the polynucleotide binding partner of the second polynucleotide, or if the first polynucleotide can hybridize to the second polynucleotide under stringent hybridization conditions.

A "vector" is a polynucleotide that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06. A nucleotide sequence is "operably linked" to a regulatory sequence if the regulatory sequence affects the expression (e.g., the level, timing, or location of expression) of the nucleotide sequence.

A "host cell" is a cell that can be used to express a polynucleotide of the disclosure. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The term "isolated molecule" (where the molecule is, for example, a polypeptide or a polynucleotide) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

A protein or polypeptide is "substantially pure," "substantially homogeneous," or "substantially purified" when at least about 60% to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences. A "cleavable linker" refers to a linker that can be degraded or otherwise severed to separate the two components connected by the cleavable linker. Cleavable linkers are generally cleaved by enzymes, typically peptidases, proteases, nucleases, lipases, and the like. Cleavable linkers may also be cleaved by environmental cues, such as, for example, changes in temperature, pH, salt concentration, etc.

The terms "label" or "labeled" as used herein refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^3H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

The term "immunotherapy" refers to cancer treatments which include, but are not limited to, treatment using depleting antibodies to specific tumor antigens; treatment using antibody-drug conjugates; treatment using agonistic, antagonistic, or blocking antibodies to co-stimulatory or co-inhibitory molecules (immune checkpoints) such as CD276, CD272, CTLA-4, PD-1, PD-L1, CD40, SIRPa, CD47, OX-40, CD137, GITR, LAGS, ICOS, CD27, 4-1BB, TIM-3, B7-H4, Siglec 7, Siglec 8, Siglec 9, Siglec 15, and VISTA; treatment using bispecific T cell engaging antibodies (BiTE®) such as blinatumomab: treatment involving administration of biological response modifiers such as IL-2, IL-12, IL-15, IL-21, GM-CSF, IFN-α, IFN-β and IFN-γ; treatment using therapeutic vaccines such as sipuleucel-T; treatment using dendritic cell vaccines, or tumor antigen peptide vaccines; treatment using chimeric antigen receptor (CAR)-T cells; treatment using CAR-NK cells; treatment using tumor infiltrating lymphocytes (TILs); treatment using adoptively transferred anti-tumor T cells (ex vivo expanded and/or TCR transgenic); treatment using TALL-104 cells; and treatment using immunostimulatory agents such as Toll-like receptor (TLR) agonists CpG and imiquimod, and treatment using vaccine such as BCG, whereas the combination therapy provides increased effector cell killing of tumor cells, i.e., a synergy exists between the IL-15 constructs and the immunotherapy when co-administered.

The term "effective amount" or "therapeutically effective amount" as used herein refers to an amount of a compound or composition sufficient to treat a specified disorder, condition or disease such as ameliorate, palliate, lessen, and/or delay one or more of its symptoms. In reference to NHL and other cancers or other unwanted cell proliferation, an effective amount comprises an amount sufficient to: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. An effective amount can be administered in one or more administrations.

The terms "patient," "individual," and "subject" may be used interchangeably and refer to a mammal, preferably a human or a non-human primate, but also domesticated mammals (e.g., canine or feline), laboratory mammals (e.g., mouse, rat, rabbit, hamster, guinea pig), and agricultural mammals (e.g., equine, bovine, porcine, ovine). In various embodiments, the patient can be a human (e.g., adult male, adult female, adolescent male, adolescent female, male child, female child) under the care of a physician or other health worker in a hospital, psychiatric care facility, as an outpatient, or other clinical context. In various embodiments, the patient may be an immunocompromised patient or a patient with a weakened immune system including, but not limited to patients having primary immune deficiency, AIDS; cancer and transplant patients who are taking certain immunosuppressive drugs; and those with inherited diseases that affect the immune system (e.g., congenital agammaglobulinemia, congenital IgA deficiency). In various embodiments, the patient has an immunogenic cancer, including, but not limited to bladder cancer, lung cancer, melanoma, and other cancers reported to have a high rate of mutations (Lawrence et al., Nature, 499(7457): 214-218, 2013).

"Pharmaceutical composition" refers to a composition suitable for pharmaceutical use in a mammal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, vehicles, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 21st Ed. 2005, Mack Publishing Co, Easton. A "pharmaceutically acceptable salt" is a salt that can be formulated into a compound for pharmaceutical use including, e.g., metal salts (sodium, potassium, magnesium, calcium, etc.) and salts of ammonia or organic amines.

The phrase "administering" or "cause to be administered" refers to the actions taken by a medical professional (e.g., a physician), or a person controlling medical care of a patient, that control and/or permit the administration of the agent (s)/compound(s) at issue to the patient. Causing to be administered can involve diagnosis and/or determination of an appropriate therapeutic regimen, and/or prescribing particular agent(s)/compounds for a patient. Such prescribing can include, for example, drafting a prescription form, annotating a medical record, and the like. Where administration is described herein, "causing to be administered" is also contemplated.

"Resistant or refractory cancer" refers to tumor cells or cancer that do not respond to previous anti-cancer therapy including, e.g., chemotherapy, surgery, radiation therapy, stem cell transplantation, and immunotherapy. Tumor cells can be resistant or refractory at the beginning of treatment, or they may become resistant or refractory during treatment. Refractory tumor cells include tumors that do not respond at the onset of treatment or respond initially for a short period but fail to respond to treatment. Refractory tumor cells also include tumors that respond to treatment with anticancer therapy but fail to respond to subsequent rounds of therapies. For purposes of this invention, refractory tumor cells also encompass tumors that appear to be inhibited by treatment with anticancer therapy but recur up to five years, sometimes up to ten years or longer after treatment is discontinued. The anticancer therapy can employ chemotherapeutic agents alone, radiation alone, targeted therapy alone, surgery alone, or combinations thereof. For ease of description and not limitation, it will be understood that the refractory tumor cells are interchangeable with resistant tumor.

The terms "treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

It is understood that aspect and embodiments of the disclosure described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the disclosure described herein include "consisting" and/or "consisting essentially of" aspects and variations.

IL-15/IL-15RαSushi Complexes

Interleukin-15 (IL-15) is a cytokine identified by two independent groups based upon its ability to stimulate proliferation of the IL-2-dependent CTLL-2 T-cell line in the presence of neutralizing anti-IL-2 antibodies (Steel et al., Trends in Pharmacological Sciences, 33(1):35-41, 2012). IL-15 and Interleukin-2 (IL-2) have similar biologic properties in vitro, consistent with their shared receptor (R) signaling components (IL-2/15Rβγ$_c$). However, specificity for IL-15 versus IL-2 is provided by unique private a-chain receptors that complete the IL-15Rαβγ and IL-2Rαβγ heterotrimeric high-affinity receptor complexes and thereby allow differential responsiveness depending on the ligand and high-affinity receptor expressed. Intriguingly, both IL-15 and IL-15Rα transcripts have a much broader tissue distribution than IL-2/IL-2Rα. Further, multiple complex posttranscriptional regulatory mechanisms tightly control IL-15 expression. Thus, based upon complex regulation, as well as differential patterns of IL-15 and IL-15Rα expression, it is likely that the critical in vivo functions of this receptor/ligand pair differ from those of IL-2 and IL-2Rα. Studies to date examining the biology of IL-15 have identified several key nonredundant roles, such as IL-15's importance during natural killer (NK) cell, NK-T cell, and intestinal intraepithelial lymphocyte development and function. A role for IL-15 during autoimmune processes such as rheumatoid arthritis and malignancies such as adult T-cell leukemia suggest that dysregulation of IL-15 may result in deleterious effects for the host (Fehniger et al., Blood, 97:14-32, 2001).

As used herein, the terms "native IL-15" and "native interleukin-15" in the context of proteins or polypeptides refer to any naturally occurring mammalian interleukin-15 amino acid sequences, including immature or precursor and mature forms. Non-limiting examples of GeneBank Accession Nos. for the amino acid sequence of various species of native mammalian interleukin-15 include NP_000576 (human, immature form), CAA62616 (human, immature form), NP_001009207 (*Felis catus*, immature form), AAB94536 (*rattus*, immature form), AAB41697 (*rattus*, immature form), NP_032383 (*Mus musculus*, immature form), AAR19080 (canine), AAB60398 (*macaca* mulatta, immature form), AAI00964 (human, immature form), AAH23698 (*Mus musculus*, immature form), and AAH18149 (human). In various embodiments of the present invention, native IL-15 is the immature or precursor form of a naturally occurring mammalian IL-15. In other embodiments, native IL-15 is the mature form of a naturally occurring mammalian IL-15. In various embodiments, native IL-15 is the precursor form of naturally occurring human IL-15. In various embodiments, native IL-15 is the mature form of naturally occurring human IL-15. In various embodiments, the native IL-15 protein/polypeptide is isolated or purified. In various embodiments, the IL-15 domain is derived from the amino acid sequence of the human IL-15 precursor sequence set forth in SEQ ID NO: 1:

```
                                       (SEQ ID NO: 1)
MRISKPHLRSISIQCYLCLLLNSHFLTEAGIHVFILGCFSAGLPKTEANW

VNVISDLKKIEDLIQSMHIDATLYTESDVHPSCKVTAMKCFLLELQVISL

ESGDASIHDTVENLIILANNSLSSNGNVTESGCKECEELEEKNIKEFLQS

FVHIVQMFINTS
```

IL-15 receptor is a type I cytokine receptor consisting of a beta (β) and gamma (γ) subunit that it shares with IL-2 receptor, and an alpha (a) subunit which binds IL-15 with a high affinity. The full-length human IL-15Rα is a type-1 transmembrane protein with a signal peptide of 32 AAs, an extracellular domain of 173 AAs, a transmembrane domain of 21 AAs, a 37-AA cytoplasmic tail, and multiple N- or O-linked glycosylation sites (Anderson et al., J. Biol Chem, 270:29862-29869, 1995). It has been previously demonstrated that a natural soluble form of IL-15R alpha chain corresponding to the entire extracellular domain of IL-15R alpha behaves as a high affinity IL-15 antagonist. However, in sharp contrast with that finding, it was demonstrated that a recombinant, soluble sushi domain of IL-15R alpha, which bears most of the binding affinity for IL-15, behaves as a potent IL-15 agonist by enhancing its binding and biological effects (proliferation and protection from apoptosis) through the IL-15R beta/gamma heterodimer, whereas it does not affect IL-15 binding and function of the tripartite IL-15R alpha/beta/gamma membrane receptor. These results suggested that, if naturally produced, such soluble sushi domains might be involved in the IL-15 trans-presentation mechanism (Mortier et al., J. Biol Chem, 281(3):1612-1619, 2006).

As used herein, the terms "native IL-15Rα" and "native interleukin-15 receptor alpha" in the context of proteins or polypeptides refer to any naturally occurring mammalian interleukin-15 receptor alpha ("IL-15Rα") amino acid sequence, including immature or precursor and mature forms and naturally occurring isoforms. Non-limiting examples of GeneBank Accession Nos. for the amino acid sequence of various native mammalian IL-15Rα include NP_002180 (human), ABK41438 (*Macaca mulatta*), NP_032384 (*Mus musculus*), Q60819 (*Mus musculus*), Q13261 (human). In various embodiments, native IL-15Rα is the immature form of a naturally occurring mammalian IL-15Rα polypeptide. In various embodiments, native IL-15Rα is the mature form of a naturally occurring mammalian IL-15Rα polypeptide. In various embodiments, native IL-15Rα is a form of a naturally occurring mammalian IL-15Rα polypeptide. In various embodiments, native IL-15Rα is the full-length form of a naturally occurring mammalian IL-15Rα polypeptide. In various embodiments, native IL-15Rα is the immature form of a naturally occurring human IL-15Rα polypeptide. In various embodiments, native IL-15Rα is the mature form of a naturally occurring human IL-15Rα polypeptide. In various embodiments, native IL-15Rα is the form of a naturally occurring human IL-15Rα polypeptide. In various embodiments, native IL-15Rα is the full-length form of a naturally occurring human IL-15Rα polypeptide. In various embodiments, a native IL-15Rα protein or polypeptide is isolated or purified. In various embodiments, the IL-15Rα domain is derived from the amino acid sequence of the human IL-15Rα sequence set forth in SEQ ID NO: 3:

(SEQ ID NO: 3)
MAPRRARGCRTLGLPALLLLLLLRPPATRGITCPPPMSVEHADIWVKSYS

LYSRERYICNSGFKRKAGTSSLTECVLNKATNVAHWTTPSLKCIRDPALV

HQRPAPPSTVTTAGVTPQPESLSPSGKEPAASSPSSNNTAATTAAIVPGS

QLMPSKSPSIGITEISSHESSHGTPSQTTAKNWELTASASHQPPGVYPQG

HSDTTVAISTSTVLLCGLSAVSLLACYLKSRQTPPLASVEMEAMEALPVT

WGTSSRDEDLENCSHHL

In various embodiments, native IL-15Rα is the full extracellular form of a naturally occurring human IL-15Rα polypeptide. In various embodiments, a native IL-15Rα protein or polypeptide is isolated or purified. In various embodiments, the IL-15Rα extracellular domain is derived from the amino acid sequence of the human IL-15Rα sequence set forth in SEQ ID NO: 4:

(SEQ ID NO: 4)
ITCPPPMSVEHADIWVKSYSLYSRERYICNSGFKRKAGTSSLTECVLNKA

TNVAHWTTPSLKCIRDPALVHQRPAPPSTVTTAGVTPQPESLSPSGKEPA

ASSPSSNNTAATTAAIVPGSQLMPSKSPSTGTTEISSHESSHGTPSQTTA

KNWELTASASHQPPGVYPQGHSDTT

In various embodiments, the IL-15 fusion proteins of the present invention contain an IL-15/IL-15RαSushi complex wherein the IL-15 domain comprises the amino acid sequence of the mature human IL-15 polypeptide as set forth in SEQ ID NO: 2:

(SEQ ID NO: 2)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS and wherein the IL-15RαSushi domain comprises the amino acid sequence of the mature human IL-15Rα polypeptide as set forth in SEQ ID NO: 5:

(SEQ ID NO: 5)
ITCPPPMSVEHADIWVKSYSLYSRERYICNSGFKRKAGTSSLTECVLNKA

TNVAHWTTPSLKCIRDPALVHQRPAPP

In various embodiments, the IL-15 domain of the IL-15/IL-15RαSushi complex will be an IL-15 variant (or mutant) comprising a sequence derived from the sequence of the mature human IL-15 polypeptide as set forth in SEQ ID NO: 2. Variants (or mutants) of IL-15 are referred to herein using the native amino acid, its position in the mature sequence and the variant amino acid. For example, "huIL-15S58D" refers to human IL-15 comprising a substitution of S to D at position 58 of SEQ ID NO: 2. In various embodiments, the IL-15 variant binds the IL-15Rα polypeptide and functions as an IL-15 agonist or antagonist. In various embodiments, the IL-15 variants with agonist activity have super agonist activity. In various embodiments, the IL-15 variant can function as an IL-15 agonist or antagonist independent of its association with IL-15Rα. IL-15 agonists are exemplified by comparable or increased biological activity compared to wild type IL-15. IL-15 antagonists are exemplified by decreased biological activity compared to wild type IL-15 or by the ability to inhibit IL-15-mediated responses. In various embodiments, the IL-15 variant binds with increased or decreased activity to the IL-15Rβ$\gamma_c$ receptors. In various embodiments, the sequence of the IL-15 variant has at least one amino acid change, e.g. substitution or deletion, compared to the native IL-15 sequence, such changes resulting in IL-15 agonist or antagonist activity. In various embodiments, the amino acid substitutions/deletions are in the domains of IL-15 that interact with IL-15Rβ and/or $\gamma_c$. In various embodiments, the amino acid substitutions/deletions do not affect binding to the IL-15Rα polypeptide or the ability to produce the IL-15 variant. Suitable amino acid substitutions/deletions to generate IL-15 variants can be identified based on known IL-15 structures, comparisons of IL-15 with homologous molecules such as IL-2 with known structure, through rational or random mutagenesis and functional assays, as provided herein, or other empirical methods. Additionally, suitable amino acid substitutions can be conservative or non-conservative changes and insertions of additional amino acids. In various embodiments, the IL-15 variants of the invention contain one or more than one amino acid substitutions/deletions at position 30, 31, 32, 62, 63, 67, 68, or 108 of the mature human IL-15 sequence set forth in SEQ ID NO: 2. In various embodiments, the D30T ("D30" refers to the amino acid "D" and residue position "30" in the native mature human IL-15 sequence and "T" refers to the substituted amino acid residue at that position in the IL-15 variant), V31Y, H32E, T62D, I68F or Q108M substitutions result in IL-15 variants with antagonist activity and S58D substitutions result in IL-15 variants with agonist activity.

In various embodiments, the IL-15 domain of the IL-15/IL-15RαSushi complex will be a human IL-15 variant polypeptide with a deletion from position 111-114 (SEQ ID NO: 39). In various embodiments, the IL-15 domain of the IL-15/IL-15RαSushi complex will be a human IL-15 variant polypeptide with a deletion from position 109-114 (SEQ ID NO: 40). In various embodiments, the IL-15 domain of the IL-15/IL-15RαSushi complex will be a human IL-15 variant polypeptide with a deletion from position 108-114 (SEQ ID NO: 41). In various embodiments, the IL-15 domain of the IL-15/IL-15RαSushi complex will be a human IL-15 variant polypeptide with a deletion from position 105-114 (SEQ ID NO: 42). In various embodiments, the IL-15 domain of the IL-15/IL-15RαSushi complex will be a human IL-15 variant polypeptide with a 'GS' Insertion after position N95 (SEQ ID NO: 43). In various embodiments, the IL-15 domain of the IL-15/IL-15RαSushi complex will be a human IL-15 variant polypeptide with a 'GGSGG' Insertion after position N95 (SEQ ID NO: 44). In various embodiments, the IL-15 domain of the IL-15/IL-15RαSushi complex will be a human IL-15 variant polypeptide with a 'GSSGGSGGS' insertion after position N95 (SEQ ID NO: 45).

Fc Domains

Immunoglobulins of IgG class are among the most abundant proteins in human blood. Their circulation half-lives can reach as long as 21 days. Fusion proteins have been reported to combine the Fc regions of IgG with the domains of another protein, such as various cytokines and receptors (see, for example, Capon et al., Nature, 337:525-531, 1989; Chamow et al., Trends Biotechnol., 14:52-60, 1996); U.S. Pat. Nos. 5,116,964 and 5,541,087). The prototype fusion protein is a homodimeric protein linked through cysteine residues in the hinge region of IgG Fc, resulting in a molecule similar to an IgG molecule without the heavy chain variable and CH1 domains and light chains. The dimer nature of fusion proteins comprising the Fc domain may be advantageous in providing higher order interactions (i.e. bivalent or bispecific binding) with other molecules. Due to the structural homology, Fc fusion proteins exhibit in vivo pharmacokinetic profile comparable to that of human IgG with a similar isotype.

The term "Fc" refers to molecule or sequence comprising the sequence of a non-antigen-binding fragment of whole antibody, whether in monomeric or multimeric form. The original immunoglobulin source of the native Fc is preferably of human origin and may be any of the immunoglobulins. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), Nucleic Acids Res. 10: 4071-9). The term "native Fc" as used herein is generic to the monomeric, dimeric, and multimeric forms. Fc domains containing binding sites for Protein A, Protein G, various Fc receptors and complement proteins.

In various embodiments, the term "Fc variant" refers to a molecule or sequence that is modified from a native Fc but still comprises a binding site for the salvage receptor, FcRn. International applications WO 97/34631 (published Sep. 25, 1997) and WO 96/32478 describe exemplary Fc variants, as well as interaction with the salvage receptor, and are hereby incorporated by reference. Furthermore, a native Fc comprises sites that may be removed because they provide structural features or biological activity that are not required for the fusion molecules of the present invention. Thus, in various embodiments, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by recombinant gene expression or by other means.

In one aspect, the IL-15 fusion proteins of the present invention comprise an IL-15/IL-15RαSushi complex and at least one heterologous protein attached to the IL-15/IL-15RαSushi complex either directly or through a peptide linker sequence to form an IL-15 fusion protein. As used herein the term "fusion protein" refers to a protein having a heterologous polypeptide attached via recombinant DNA techniques. In various embodiments, the heterologous protein is an Fc domain (or functional fragment thereof) and the resultant fusion protein is an IL-15/IL-15RαSushi complex-Fc fusion protein. In various embodiments, IL-15/IL-15RαSushi complex are fused to at least one polypeptide that confers extended half-life on the fusion molecule. Such polypeptides include an IgG Fc or other polypeptides that bind to the neonatal Fcγ/receptor, human serum albumin, or polypeptides that bind to a protein having extended serum half-life, including IgGs, non-IgG immunoglobulin, proteins and non-protein agents, that have increased in vivo half-lives due to the presence of an IgG constant domain, or a portion thereof that binds the FcRn, having one or more amino acid modifications that increase the affinity of the constant domain or fragment for FcRn. Such proteins and molecules with increased half-lives have the advantage that smaller amounts and or less frequent dosing is required in the therapeutic, prophylactic or diagnostic use of such molecules (see, e.g., U.S. Pat. No. 7,658,921). In various embodiments, the Fc domain is selected from the group consisting of human IgG1 Fc domain, human IgG2 Fc domain, human IgG3 Fc domain, human IgG4 Fc domain, IgA Fc domain, IgD Fc domain, IgE Fc domain, IgG Fc domain and IgM Fc domain; or any combination thereof. In various embodiments, the Fc domain includes an amino acid change that results in an Fc domain having altered complement or Fc receptor binding properties. Amino acid changes to produce an Fc domain with altered complement or Fc receptor binding properties are known in the art.

In various embodiments, the Fc domain sequence used to make dimeric IL-15/IL-15Rα complex-Fc fusion proteins is the human IgG1-Fc domain sequence set forth in SEQ ID NO: 6:

(SEQ ID NO: 6)
DKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

```
GFYPSDIAVEWESNGQPENNYKTTPPVLDSDGSFFLYSKLTVDKSRWQQG

NVFSCSVMHEALHNHYTQKSLSLSPG
``` wherein SEQ ID NO: 6 contains amino acid substitutions (underlined) that ablate FcγR and C1q binding.

In various embodiments, the heterodimeric Fc domain sequence used to make monovalent IL-15/IL-15Rα complex-Fc fusion proteins is the Knob-Fc domain sequence set forth in SEQ ID NO: 7:

```
                                        (SEQ ID NO: 7)
DKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSREEMTKNQVSLWCLVK

GFYPSDIAVEWESNGQPENNYKTTPPVLDSDGSFFLYSKLTVDKSRWQQG

NVFSCSVMHEALHNHYTQKSLSLSPG
``` wherein SEQ ID NO: 7 contains amino acid substitutions (underlined) that ablate FcγR and C1q binding.

In various embodiments, the heterodimeric Fc domain sequence used to make monovalent IL-15/IL-15Rα complex-Fc fusion proteins is the Hole-Fc domain sequence set forth in SEQ ID NO: 8:

```
                                        (SEQ ID NO: 8)
DKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCREEMTKNQVSLSCAVK

GFYPSDIAVEWESNGQPENNYKTTPPVLDSDGSFFLVSKLTVDKSRWQQG

NVFSCSVMHEALHNHYTQKSLSLSPG
``` wherein SEQ ID NO: 8 contains amino acid substitutions (underlined) that ablate FcγR and C1q binding.

Linkers

In various embodiments, the heterologous protein (e.g., Fc domain) is covalently linked to the IL-15 polypeptide (or functional fragment thereof) of the IL-15/IL-15RαSushi complex by polypeptide linker sequence. In various embodiments, the linker may be an artificial sequence of between 5, 10, 15, 20, 30, 40 or more amino acids that are relatively free of secondary structure. In various embodiments, the linker is rich in G/S content (e.g., at least about 60%, 70%, 80%, 90%, or more of the amino acids in the linker are G or S). In various embodiments, the linker is selected from the group of sequences set forth in SEQ ID NOs: 9-12 and SEQ ID NO: 47. Each peptide linker sequence can be selected independently.

Examples of Novel IL-15/IL-15RαSushi Complex-Fc Fusion Proteins

In various embodiments, the IL-15/IL-15RαSushi heterodimeric Fc fusion protein of the present invention (also referred to hereinafter as "P-0153") comprises a chain 1 (Hole-Fc-linker-IL-15) having the amino acid sequence set forth in SEQ ID NO: 13:

```
                                        (SEQ ID NO: 13)
DKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCREEMTKNQVSLSCAVK

GFYPSDIAVEWESNGQPENNYKTTPPVLDSDGSFFLVSKLTVDKSRWQQG

NVFSCSVMHEALHNHYTQKSLSLSPGEPKSSDKTHTSPPSPNWVNVISDL

KKIEDLIQSMHIDATLYTESDVHPSCKVTAMKCFLLELQVISLESGDASI

HDTVENLIILANNSLSSNGNVTESGCKECEELEEKNIKEFLQSFVHIVQM

FINTS
``` wherein the IL-15 domain sequence is underlined, and the peptide linker sequence is in bold; and a chain 2 (Knob-Fc-linker-IL-15Rα-Sushi+) having the amino acid sequence set forth in SEQ ID NO: 14:

```
                                        (SEQ ID NO: 14)
DKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSREEMTKNQVSLWCLVK

GFYPSDIAVEWESNGQPENNYKTTPPVLDSDGSFFLYSKLTVDKSRWQQG

NVFSCSVMHEALHNHYTQKSLSLSPGEPKSSDKTHTSPPSPITCPPPMSV

EHADIWVKSYSLYSRERYICNSGFKRKAGTSSLTECVLNKATNVAHWTTP

SLKCIRDPALVHQRPAPP
``` wherein the IL-15Rα-Sushi+ domain sequence is underlined, and the peptide linker sequence is in bold.

In various embodiments, the IL-15/IL-15RαSushi heterodimeric Fc fusion protein of the present invention (also referred to hereinafter as "P-0156") comprises a chain 1 (IL-15-Linker-Hole-Fc) having the amino acid sequence set forth in SEQ ID NO: 15:

```
                                        (SEQ ID NO: 15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS**GCPPCPAPEAAGAPSVFLFPPKPKDTLMISRTPEVT

CVVVDVSHEDPEVKFNWYVDGVEVHNAKTKPREEQYNSTYRVVSVLTVLH

QDWLNGKEYKCKVSNKALPAPIEKTISKAKGQPREPQVYTLPPCREEMTK

NQVSLSCAVKGFYPSDIAVEWESNGQPENNYKTTPPVLDSDGSFFLVSKL

TVDKSRWQQGNVFSCSVMHEALHNHYTQKSLSLSPG
``` wherein the IL-15 domain sequence is underlined, and the peptide linker sequence is in bold; and a chain 2 (IL-15Rα-Sushi+-Linker-Knob-Fc) having the amino acid sequence set forth in SEQ ID NO: 16:

```
                                        (SEQ ID NO: 16)
ITCPPPMSVEHADIWVKSYSLYSRERYICNSGFKRKAGTSSLTECVLNKA

TNVAHWTTPSLKCIRDPALVHQRPAPPGCPPCPAPEAAGAPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VCTLPPSREEMTKNQVSLWCLVKGFYPSDIAVEWESNGQPENNYKTTPPV

LDSDGSFFLYSKLTVDKSRWQQGNVFSCSVMHEALHNHYTQKSLSLSPG
``` wherein the IL-15Rα-Sushi+ domain sequence is underlined, and the peptide linker sequence is in bold.

In various embodiments, the IL-15/IL-15RαSushi heterodimeric Fc fusion protein of the present invention (also referred to hereinafter as "P-0155") comprises a chain 1 (Hole Fc-linker-IL-15) having the amino acid sequence set forth in SEQ ID NO: 18:

(SEQ ID NO: 18)
DKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCREEMTKNQVSLSCAVK

GFYPSDIAVEWESNGQPENNYKTTPPVLDSDGSFFLVSKLTVDKSRWQQG

NVFSCSVMHEALHNHYTQKSLSLSPGGGGGSGGGGSNWVNVISDLKKIED

LIQSMHIDATLYTESDVHPSCKVTAMKCFLLELQVISLESGDASIHDTVE

NLIILANNSLSSNGNVTESGCKECEELEEKNIKEFLQSFVHIVQMFINTS wherein the IL-15 domain sequence is underlined, and the peptide linker sequence is in bold; and a chain 2 (Knob-Fc-linker-IL-15Rα-Sushi+) having the amino acid sequence set forth in SEQ ID NO: 17:

(SEQ ID NO: 17)
DKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSREEMTKNQVSLWCLVK

GFYPSDIAVEWESNGQPENNYKTTPPVLDSDGSFFLYSKLTVDKSRWQQG

NVFSCSVMHEALHNHYTQKSLSLSPGGGGGSGGGGSITCPPPMSVEHADI

WVKSYSLYSRERYICNSGFKRKAGTSSLTECVLNKATNVAHWTTPSLKCI

RDPALVHQRPAPP wherein the IL-15Rα-Sushi+ domain sequence is underlined, and the peptide linker sequence is in bold.

In various embodiments, the monovalent IL-15Fc fusion protein of the present invention (also referred to hereinafter as "P-0162") comprises a chain 1 (Hole Fc-linker-IL-15) having the amino acid sequence set forth in SEQ ID NO: 13 and a chain 2 (Knob-Fc) having the amino acid sequence set forth in SEQ ID NO: 7.

In various embodiments, the bivalent IL-15 Fc fusion protein of the present invention (also referred to hereinafter as "P-0167") comprises a chain 1 (Hole Fc-linker-IL-15) having the amino acid sequence set forth in SEQ ID NO: 13 and a chain 2 (Knob-Fc-linker-IL-15Rα-Sushi+) having the amino acid sequence set forth in SEQ ID NO: 55:

(SEQ ID NO: 55)
DKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSREEMTKNQVSLWCLVK

GFYPSDIAVEWESNGQPENNYKTTPPVLDSDGSFFLYSKLTVDKSRWQQG

NVFSCSVMHEALHNHYTQKSLSLSPGEPKSSDKTHTSPPSPNWVNVISDL

KKIEDLIQSMHIDATLYTESDVHPSCKVTAMKCFLLELQVISLESGDASI

HDTVENLIILANNSLSSNGNVTESGCKECEELEEKNIKEFLQSFVHIVQM

FINTS wherein the IL-15 domain sequence is underlined, and the peptide linker sequence is in bold.

In various embodiments, the monovalent IL-15/IL-15RαSushi (non-covalent) Fc fusion protein of the present invention (also referred to hereinafter as "P-0197") comprises a chain 1 (Hole-Fc-Linker-IL-15) having the amino acid sequences set forth in SEQ ID NO: 13, a chain 2 (IL-15Rα-Sushi+) having the amino acid sequence set forth in SEQ ID NO: 5, and a chain 3 (Knob-Fc) having the amino acid sequence set forth in SEQ ID NO: 7.

In various embodiments, the bivalent IL-15/IL-15RαSushi (non-covalent) Fc fusion protein of the present invention (also referred to hereinafter as "P-0198") comprises a chain 1 (Hole-Fc-Linker-IL-15) having the amino acid sequences set forth in SEQ ID NO: 13, a chain 2 (IL-15Rα-Sushi+) having the amino acid sequence set forth in SEQ ID NO: 5, and a chain 3 (Knob-Fc-Linker-IL-15) having the amino acid sequence set forth in SEQ ID NO: 55.

In various embodiments, the monovalent IL-15/IL-15RαSushi (non-covalent) Fc fusion protein of the present invention (also referred to hereinafter as "P-0201") comprises a chain 1 (IL-15-Linker-Hole-Fc) having the amino acid sequences set forth in SEQ ID NO: 15, a chain 2 (IL-15Rα-Sushi+) having the amino acid sequence set forth in SEQ ID NO: 5, and a chain 3 (Knob-Fc) having the amino acid sequence set forth in SEQ ID NO: 7.

In various embodiments, the monovalent IL-15/IL-15RαSushi (non-covalent) Fc fusion protein of the present invention (also referred to hereinafter as "P-0207") comprises a chain 1 (Hole-Fc-Linker-IL-15) having the amino acid sequences set forth in SEQ ID NO: 18, a chain 2 (IL-15Rα-Sushi+) having the amino acid sequence set forth in SEQ ID NO: 5, and a chain 3 (Knob-Fc) having the amino acid sequence set forth in SEQ ID NO: 7.

In various embodiments, the monovalent IL-15/IL-15RαSushi (non-covalent) Fc fusion protein of the present invention (also referred to hereinafter as "P-0217") comprises a chain 1 (Hole-Fc-Linker-IL-15) having the amino acid sequences set forth in SEQ ID NO: 54:

(SEQ ID NO: 54)
DKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCREEMTKNQVSLSCAVK

GFYPSDIAVEWESNGQPENNYKTTPPVLDSDGSFFLVSKLTVDKSRWQQG

NVFSCSVMHEALHNHYTQKSLSLSPGGGGGSGGGGSGGGGSNWVNVISDL

KKIEDLIQSMHIDATLYTESDVHPSCKVTAMKCFLLELQVISLESGDASI

HDTVENLIILANNSLSSNGNVTESGCKECEELEEKNIKEFLQSFVHIVQM

FINTS wherein the IL-15 domain sequence is underlined and the peptide linker sequence is in bold; a chain 2 (IL-15Rα-Sushi+) having the amino acid sequence set forth in SEQ ID NO: 5, and a chain 3 (Knob-Fc) having the amino acid sequence set forth in SEQ ID NO: 7.

In various embodiments, the monovalent IL-15/IL-15Rα (non-covalent) complex-Fc fusion protein of the present invention (also referred to hereinafter as "P-0219") comprises a chain 1 (Hole-Fc-Linker-IL-15) having the amino acid sequences set forth in SEQ ID NO: 54, a chain 2 (IL-15Rα-ECD) having the amino acid sequence set forth in SEQ ID NO: 4, and a chain 3 (Knob-Fc) having the amino acid sequence set forth in SEQ ID NO: 7.

In various embodiments, the monovalent IL-15/IL-15RαSushi (non-covalent) Fc fusion protein of the present invention (also referred to hereinafter as "P-0221") comprises a chain 1 (IL-15-Linker-Hole-Fc) having the amino acid sequences set forth in SEQ ID NO: 19:

```
                                          (SEQ ID NO: 19)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTSGGGGSGGGGSGGGGSCPPCPAPEAAGAPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPCREEMTKNQVSLSCAVKGFYPSDIAVEWESNGQPENNYKTIPP

VLDSDGSFFLVSKLTVDKSRWQQGNVFSCSVMHEALHNHYTQKSLSLSPG
``` wherein the IL-15 domain sequence is underlined and the peptide linker sequence is in bold; a chain 2 (IL-15Rα-Sushi+) having the amino acid sequence set forth in SEQ ID NO: 5, and a chain 3 (Knob-Fc) having the amino acid sequence set forth in SEQ ID NO: 7.

In various embodiments, the monovalent IL-15/IL-15Rα (non-covalent) Fc fusion protein of the present invention (also referred to hereinafter as "P-0222") comprises a chain 1 (IL-15-Linker-Hole-Fc) having the amino acid sequences set forth in SEQ ID NO: 19, a chain 2 (IL-15Rα-ECD) having the amino acid sequence set forth in SEQ ID NO: 4, and a chain 3 (Knob-Fc) having the amino acid sequence set forth in SEQ ID NO: 7.

In various embodiments, the bivalent IL-15/IL-15RαSushi (non-covalent) Fc fusion protein of the present invention (also referred to hereinafter as "P-0234") comprises a chain 1 (Fc-Linker-IL-15) having the amino acid sequences set forth in SEQ ID NO: 20:

```
                                          (SEQ ID NO: 20)
DKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGGGGGSGGGGSGGGGSNWVNVISDL

KKIEDLIQSMHIDATLYTESDVHPSCKVTAMKCFLLELQVISLESGDASI

HDTVENLIILANNSLSSNGNVTESGCKECEELEEKNIKEFLQSFVHIVQM

FINTS
``` wherein the IL-15 domain sequence is underlined, and the peptide linker sequence is in bold; and a chain 2 (IL-15Rα-Sushi+) having the amino acid sequence set forth in SEQ ID NO: 5.

In various embodiments, the bivalent IL-15/IL-15RαSushi (non-covalent) Fc fusion protein of the present invention (also referred to hereinafter as "P-0223") comprises a chain 1 (IL-15-Linker-Fc) having the amino acid sequences set forth in SEQ ID NO: 21:

```
                                          (SEQ ID NO: 21)
NWVNVISDLKKIEDLIQSMHIDATLYTESDVHPSCKVTAMKCFLLELQVI

SLESGDASHDTVENLIILANNSLSSNGNVTESGCKECEELEEKNIKEFLQ

SFVHIVQMFINTSGGGGSGGGGSGGGGSCPPCPAPEAAGAPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCAVKGFYPSDIAVEWESNGQPENNYKTIPPV

LDSDGSFFLVSKLTVDKSRWQQGNVFSCSVMHEALHNHYTQKSLSLSPG
``` wherein the IL-15 domain sequence is underlined, and the peptide linker sequence is in bold; and a chain 2 (IL-15Rα-Sushi+) having the amino acid sequence set forth in SEQ ID NO: 5.

In various embodiments, the bivalent IL-15/IL-15Rα (non-covalent) Fc fusion protein of the present invention (also referred to hereinafter as "P-0220") comprises a chain 1 (Fc-Linker-IL-15) having the amino acid sequences set forth in SEQ ID NO: 20, and a chain 2 (IL-15Rα-ECD) having the amino acid sequence set forth in SEQ ID NO: 4.

In various embodiments, the bivalent IL-15/IL-15Rα (non-covalent) Fc fusion protein of the present invention (also referred to hereinafter as "P-0224") comprises a chain 1 (IL-15-Linker-Fc) having the amino acid sequences set forth in SEQ ID NO: 21, and a chain 2 (IL-15Rα-ECD) having the amino acid sequence set forth in SEQ ID NO: 4.

In various embodiments, the monovalent IL-15 (non-covalent)/IL-15RαSushi Fc fusion protein of the present invention (also referred to hereinafter as "P-0165") comprises a chain 1 (IL-15) having the amino acid sequences set forth in SEQ ID NO: 2, a chain 2 (Knob-Fc-linker-IL-15Rα-Sushi+) having the amino acid sequence set forth in SEQ ID NO: 14, and a chain 3 (Hole-Fc) having the amino acid sequence set forth in SEQ ID NO: 8.

In various embodiments, the monovalent IL-15 (non-covalent)/IL-15RαSushi Fc fusion protein of the present invention (also referred to hereinafter as "P-0166") comprises a chain 1 (IL-15) having the amino acid sequences set forth in SEQ ID NO: 2, a chain 2 (Knob-Fc-linker-IL-15Rα-Sushi+) having the amino acid sequence set forth in SEQ ID NO: 22:

```
                                          (SEQ ID NO: 22)
DKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSREEMTKNQVSLWCLVK

GFYPSDIAVEWESNGQPENNYKTTPPVLDSDGSFFLYSKLTVDKSRWQQG

NVFSCSVMHEALHNHYTQKSLSLSPGGGGGSGGGGSITCPPPMSVEHADI

WVKSYSLYSRERYICNSGFKRKAGTSSLTECVLNKATNVAHWTTPSLKCI

RDPALVHQRPAPP
``` wherein the IL-15 RαSushi domain sequence is underlined and the peptide linker sequence is in bold; and a chain 3 (Hole-Fc) having the amino acid sequence set forth in SEQ ID NO: 8.

In various embodiments, the bivalent IL-15 (non-covalent)/IL-15RαSushi Fc fusion protein of the present invention (also referred to hereinafter as "P-0218") comprises a chain 1 (IL-15) having the amino acid sequences set forth in SEQ ID NO: 2, a chain 2 (Fc-linker-IL-15Rα-Sushi+) having the amino acid sequence set forth in SEQ ID NO: 23:

(SEQ ID NO: 23)
DKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGGGGGSGGGGSITCPPPMSVEHADI

WVKSYSLYSRERYICNSGFKRKAGTSSLTECVLNKATNVAHWTTPSLKCI

RDPALVHQRPAPP wherein the IL-15 RαSushi domain sequence is underlined and the peptide linker sequence is in bold.

In various embodiments, the IL-15/IL-15RαSushi complex will comprise an IL-15 variant having the amino acid sequence selected from the group consisting of the sequences set forth in SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, and SEQ ID NO: 45.

In various embodiments, the bivalent IL-15/IL-15RαSushi (non-covalent) Fc fusion protein of the present invention (also referred to hereinafter as "P-0313") comprises a chain 1 (Fc-Linker-IL-15-S58D) having the amino acid sequence set forth in SEQ ID NO: 46:

(SEQ ID NO: 46)
DKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGGGGGSGGGGSGGGGSNWVNVISDL

KKIEDLIQSMHIDATLYTESDVHPSCKVTAMKCFLLELQVISLESGDADI

HDTVENLIILANNSLSSNGNVTESGCKECEELEEKNIKEFLQSFVHIVQM

FINTS wherein the IL-15 S58D variant sequence is underlined and the peptide linker sequence is in bold; and a chain 2 (IL-15 RαSushi) having the amino acid sequence set forth in SEQ ID NO: 5.

In various embodiments, the IL-15/IL-15RαSushi complex-Fc fusion protein of the present invention (also referred to hereinafter as "P-0314") comprises a chain 1 (Fc-linker-IL-15Rα-Sushi+) having the amino acid sequences set forth in SEQ ID NO: 23, and a chain 2 (IL-15 S58D) having the amino acid sequence set forth in SEQ ID NO: 24.

In various embodiments, the monovalent IL-15/IL-15RαSushi (non-covalent) Fc fusion protein of the present invention (also referred to hereinafter as "P-0666") comprises a chain 1 (Hole-Fc-Linker-IL-15-S58D) having the amino acid sequences set forth in SEQ ID NO: 48:

(SEQ ID NO: 48)
DKTHTCPPCPAPEAAGAPSVFLFPPKPKDTLMISRTPEVTCVVVDVSHEDP

EVKFNWYVDGVEVHNAKTKPREEQYNSTYRVVSVLTVLHQDWLNGKEYKCK

VSNKALPAPIEKTISKAKGQPREPQVYTLPPCREEMTKNQVSLSCAVKGFY

PSDIAVEWESNGQPENNYKTTPPVLDSDGSFFLVSKLTVDKSRWQQGNVFS

CSVMHEALHNHYTQKSLSLSPGGGGGSGGGGSGGGGSNWVNVISDLKKIED

LIQSMHIDATLYTESDVHPSCKVTAMKCFLLELQVISLESGDADIHDTVEN

LIILANNSLSSNGNVTESGCKECEELEEKNIKEFLQSFVHIVQMFINTS wherein the IL-15 domain sequence is underlined and the peptide linker sequence is in bold; a chain 2 (IL-15Rα-Sushi+) having the amino acid sequence set forth in SEQ ID NO: 5, and a chain 3 (Knob-Fc) having the amino acid sequence set forth in SEQ ID NO: 7.

In various embodiments, the monovalent IL-15/IL-15RαSushi (non-covalent) Fc fusion protein of the present invention (also referred to hereinafter as "P-0667") comprises a chain 1 (IL-15-558D-Linker-Hole-Fc) having the amino acid sequences set forth in SEQ ID NO: 49:

(SEQ ID NO: 49)
NWVNVISDLKKIEDLIQSMHIDATLYTESDVHPSCKVTAMKCFLLELQVIS

LESGDADIHDTVENLIILANNSLSSNGNVTESGCKECEELEEKNIKEFLQS

FVHIVQMFINTSGGGGSGGGGSGGGGSCPPCPAPEAAGAPSVFLFPPKPKD

TLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTL

PPCREEMTKNQVSLSCAVKGFYPSDIAVEWESNGQPENNYKTIPPVLDSDG

SFFLVSKLTVDKSRWQQGNVFSCSVMHEALHNHYTQKSLSLSPG wherein the IL-15 domain sequence is underlined and the peptide linker sequence is in bold; a chain 2 (IL-15Rα-Sushi+) having the amino acid sequence set forth in SEQ ID NO: 5, and a chain 3 (Knob-Fc) having the amino acid sequence set forth in SEQ ID NO: 7.

In various embodiments, the bivalent IL-15/IL-15RαSushi (non-covalent) Fc fusion protein of the present invention (also referred to hereinafter as "P-0668") comprises a chain 1 (IL-15-Linker-Fc) having the amino acid sequences set forth in SEQ ID NO: 50:

(SEQ ID NO: 50)
NWVNVISDLKKIEDLIQSMHIDATLYTESDVHPSCKVTAMKCFLLELQVIS

LESGDADIHDTVENLIILANNSLSSNGNVTESGCKECEELEEKNIKEFLQS

FVHIVQMFINTSGGGGSGGGGSGGGGSCPPCPAPEAAGAPSVFLFPPKPKD

TLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTL

PPSRDELTKNQVSLTCAVKGFYPSDIAVEWESNGQPENNYKTIPPVLDSDG

SFFLVSKLTVDKSRWQQGNVFSCSVMHEALHNHYTQKSLSLSPG wherein the IL-15 domain sequence is underlined, and the peptide linker sequence is in bold; and a chain 2 (IL-15Rα-Sushi+) having the amino acid sequence set forth in SEQ ID NO: 5.

In various embodiments, the monovalent IL-15 (non-covalent)/IL-15RαSushi Fc fusion protein of the present invention (also referred to hereinafter as "P-0669") comprises a chain 1 (IL-15 S58D) having the amino acid sequences set forth in SEQ ID NO: 24, a chain 2 (Knob-Fc-linker-IL-15Rα-Sushi+) having the amino acid sequence set forth in SEQ ID NO: 22; and a chain 3 (Hole-Fc) having the amino acid sequence set forth in SEQ ID NO: 8.

In various embodiments, the monovalent IL-15 (non-covalent)/IL-15RαSushi Fc fusion protein of the present invention (also referred to hereinafter as "P-0670") comprises a chain 1 (IL-15 S58D) having the amino acid sequences set forth in SEQ ID NO: 24, a chain 2 (IL-15Rα-Sushi+-linker-Knob-Fc) having the amino acid sequence set forth in SEQ ID NO: 51:

```
                                       (SEQ ID NO: 51)
ITCPPPMSVEHADIWVKSYSLYSRERYICNSGFKRKAGTSSLTECVLNKAT

NVAHWTTPSLKCIRDPALVHQRPAPPGGGGSGGGGSCPPCPAPEAAGAPSV

FLFPPKPKDTLMISRTPEVICVVVDVSHEDPEVKFNWYVDGVEVHNAKTKP

REEQYNSTYRVVSVLTVLHQDWLNGKEYKCKVSNKALPAPIEKTISKAKGQ

PREPQVCTLPPSREEMTKNQVSLWCLVKGFYPSDIAVEWESNGQPENNYKT

TPPVLDSDGSFFLYSKLTVDKSRWQQGNVFSCSVMHEALHNHYTQKSLSLS

PG
``` wherein the IL-15 RαSushi domain sequence is underlined and the peptide linker sequence is in bold; and a chain 3 (Hole-Fc) having the amino acid sequence set forth in SEQ ID NO: 8.

In various embodiments, the bivalent IL-15 (non-covalent)/IL-15RαSushi Fc fusion protein of the present invention (also referred to hereinafter as "P-0671") comprises a chain 1 (IL-15 S58D) having the amino acid sequences set forth in SEQ ID NO: 24, a chain 2 (IL-15Rα-Sushi+-Linker-Fc) having the amino acid sequence set forth in SEQ ID NO: 52:

```
                                       (SEQ ID NO: 52)
ITCPPPMSVEHADIWVKSYSLYSRERYICNSGFKRKAGTSSLTECVLNKAT

NVAHWTTPSLKCIRDPALVHQRPAPPGGGGSGGGGSCPPCPAPEAAGAPSV

FLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLS

PG
``` wherein the IL-15 RαSushi domain sequence is underlined and the peptide linker sequence is in bold.

Polynucleotides

In another aspect, the present disclosure provides isolated nucleic acid molecules comprising a polynucleotide encoding IL-15, an IL-15 variant, IL-15Rα, an IL-15Rα variant, an Fc, an Fc variant, an IL-15-Fc fusion protein, an IL-15RαSushi-Fc fusion protein, or an IL-15/IL-15RαSushi-Fc fusion protein of the present disclosure. The subject nucleic acids may be single-stranded or double stranded. Such nucleic acids may be DNA or RNA molecules. DNA includes, for example, cDNA, genomic DNA, synthetic DNA, DNA amplified by PCR, and combinations thereof. Genomic DNA encoding IL-15/IL-15RαSushi complexes is obtained from genomic libraries which are available for a number of species. Synthetic DNA is available from chemical synthesis of overlapping oligonucleotide fragments followed by assembly of the fragments to reconstitute part or all of the coding regions and flanking sequences. RNA may be obtained from prokaryotic expression vectors which direct high-level synthesis of mRNA, such as vectors using T7 promoters and RNA polymerase. cDNA is obtained from libraries prepared from mRNA isolated from various tissues that express IL-15. The DNA molecules of the disclosure include full-length genes as well as polynucleotides and fragments thereof. The full-length gene may also include sequences encoding the N-terminal signal sequence. Such nucleic acids may be used, for example, in methods for making the novel IL-15/IL-15RαSushi-Fc fusion proteins. In various embodiments, the nucleic acid molecules comprise the nucleotide sequences set forth in SEQ ID NOs: 56-63.

In various embodiments, the isolated nucleic acid molecules comprise the polynucleotides described herein, and further comprise a polynucleotide encoding at least one heterologous protein described herein. In various embodiments, the nucleic acid molecules further comprise polynucleotides encoding the linkers or hinge linkers described herein.

In various embodiments, the recombinant nucleic acids of the present disclosure may be operably linked to one or more regulatory nucleotide sequences in an expression construct. Regulatory sequences are art-recognized and are selected to direct expression of the IL-15/IL-15RαSushi-Fc fusion protein. Accordingly, the term regulatory sequence includes promoters, enhancers, and other expression control elements. Exemplary regulatory sequences are described in Goeddel; Gene Expression Technology: Methods in Enzymology, Academic Press, San Diego, Calif. (1990). Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the present disclosure. The promoters may be either naturally occurring promoters, or hybrid promoters that combine elements of more than one promoter. An expression construct may be present in a cell on an episome, such as a plasmid, or the expression construct may be inserted in a chromosome. In various embodiments, the expression vector contains a selectable marker gene to allow the selection of transformed host cells. Selectable marker genes are well known in the art and will vary with the host cell used.

In another aspect of the present disclosure, the subject nucleic acid is provided in an expression vector comprising a nucleotide sequence encoding an IL-15/IL-15RαSushi complex and operably linked to at least one regulatory sequence. The term "expression vector" refers to a plasmid, phage, virus or vector for expressing a polypeptide from a polynucleotide sequence. Vectors suitable for expression in host cells are readily available and the nucleic acid molecules are inserted into the vectors using standard recombinant DNA techniques. Such vectors can include a wide variety of expression control sequences that control the expression of a DNA sequence when operatively linked to it may be used in these vectors to express DNA sequences encoding an IL-15/IL-15RαSushi-Fc fusion protein. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., PhoS, the promoters of the yeast a-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the present disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant IL-15/IL-15RαSushi complex include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coll.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press, 1989) Chapters 16 and 17. In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the B-gal containing pBlueBac III).

In various embodiments, a vector will be designed for production of the subject IL-15/IL-15RαSushi-Fc fusion proteins in CHO cells, such as a Pcmv-Script vector (Stratagene, La Jolla, Calif.), pcDNA4 vectors (Invitrogen, Carlsbad, Calif.) and pCl-neo vectors (Promega, Madison, Wis.). As will be apparent, the subject gene constructs can be used to cause expression of the subject IL-15/IL-15RαSushi-Fc fusion proteins in cells propagated in culture, e.g., to produce proteins, including fusion proteins or variant proteins, for purification.

This present disclosure also pertains to a host cell transfected with a recombinant gene including a nucleotide sequence coding an amino acid sequence for one or more of the subject IL-15/IL-15RαSushi-Fc fusion protein. The host cell may be any prokaryotic or eukaryotic cell. For example, an IL-15/IL-15RαSushi complex of the present disclosure may be expressed in bacterial cells such as E. coli, insect cells (e.g., using a baculovirus expression system), yeast, or mammalian cells. Other suitable host cells are known to those skilled in the art.

Accordingly, the present disclosure further pertains to methods of producing the subject IL-15/IL-15RαSushi-Fc fusion proteins. For example, a host cell transfected with an expression vector encoding an IL-15/IL-15RαSushi complex can be cultured under appropriate conditions to allow expression of the IL-15/IL-15RαSushi complex to occur. The IL-15/IL-15RαSushi complex may be secreted and isolated from a mixture of cells and medium containing the IL-15/IL-15RαSushi-Fc fusion protein. Alternatively, the IL-15/IL-15RαSushi complex may be retained cytoplasmically or in a membrane fraction and the cells harvested, lysed and the protein isolated. A cell culture includes host cells, media and other byproducts. Suitable media for cell culture are well known in the art.

The polypeptides and proteins of the present disclosure can be purified according to protein purification techniques are well known to those of skill in the art. These techniques involve, at one level, the crude fractionation of the proteinaceous and non-proteinaceous fractions. Having separated the peptide polypeptides from other proteins, the peptide or polypeptide of interest can be further purified using chromatographic and electrophoretic techniques to achieve partial or complete purification (or purification to homogeneity). The term "isolated polypeptide" or "purified polypeptide" as used herein, is intended to refer to a composition, isolatable from other components, wherein the polypeptide is purified to any degree relative to its naturally-obtainable state. A purified polypeptide therefore also refers to a polypeptide that is free from the environment in which it may naturally occur. Generally, "purified" will refer to a polypeptide composition that has been subjected to fractionation to remove various other components, and which composition substantially retains its expressed biological activity. Where the term "substantially purified" is used, this designation will refer to a peptide or polypeptide composition in which the polypeptide or peptide forms the major component of the composition, such as constituting about 50%, about 60%, about 70%, about 80%, about 85%, or about 90% or more of the proteins in the composition.

Various techniques suitable for use in purification will be well known to those of skill in the art. These include, for example, precipitation with ammonium sulphate, PEG, antibodies (immunoprecipitation) and the like or by heat denaturation, followed by centrifugation; chromatography such as affinity chromatography (Protein-A columns), ion exchange, gel filtration, reverse phase, hydroxyapatite, hydrophobic interaction chromatography; isoelectric focusing; gel electrophoresis; and combinations of these techniques. As is generally known in the art, it is believed that the order of conducting the various purification steps may be changed, or that certain steps may be omitted, and still result in a suitable method for the preparation of a substantially purified polypeptide.

Pharmaceutical Compositions

In another aspect, the present disclosure provides a pharmaceutical composition comprising the IL-15/IL-15RαSushi-Fc fusion proteins in admixture with a pharmaceutically acceptable carrier. Such pharmaceutically acceptable carriers are well known and understood by those of ordinary skill and have been extensively described (see, e.g., Remington's Pharmaceutical Sciences, 18th Edition, A. R. Gennaro, ed., Mack Publishing Company, 1990). The pharmaceutically acceptable carriers may be included for purposes of modifying, maintaining or preserving, for example, the pH, osmolarity, viscosity, clarity, color, isotonicity, odor, sterility, stability, rate of dissolution or release, adsorption or penetration of the composition. Such pharmaceutical compositions may influence the physical state, stability, rate of in vivo release, and rate of in vivo clearance of the polypeptide. Suitable pharmaceutically acceptable carriers include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute thereof. In one embodiment of the present disclosure, compositions may be prepared for storage by mixing the selected composition having the desired degree of purity with optional formulation agents (Remington's Pharmaceutical Sciences, supra) in the form of a lyophilized cake or an aqueous solution. Further, the therapeutic composition may be formulated as a lyophilizate using appropriate excipients such as sucrose. The optimal pharmaceutical composition will be determined by one of ordinary skill in the art depending upon, for example, the intended route of administration, delivery format, and desired dosage.

When parenteral administration is contemplated, the therapeutic pharmaceutical compositions may be in the form of a pyrogen-free, parenterally acceptable aqueous solution comprising the desired IL-15/IL-15RαSushi complex in a pharmaceutically acceptable vehicle. A particularly suitable vehicle for parenteral injection is sterile distilled water in which a polypeptide is formulated as a sterile, isotonic solution, properly preserved. In various embodiments, pharmaceutical formulations suitable for injectable administration may be formulated in aqueous solutions, preferably in physiologically compatible buffers such as Hanks' solution, Ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Optionally, the suspension may also contain suitable stabilizers or agents to increase the solubility of the compounds and allow for the preparation of highly concentrated solutions.

In various embodiments, the therapeutic pharmaceutical compositions may be formulated for targeted delivery using a colloidal dispersion system. Colloidal dispersion systems include macromolecule complexes, nanocapsules, microspheres, beads, and lipid-based systems including oil-in-water emulsions, micelles, mixed micelles, and liposomes. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

In various embodiments, oral administration of the pharmaceutical compositions is contemplated. Pharmaceutical compositions that are administered in this fashion can be formulated with or without those carriers customarily used in the compounding of solid dosage forms such as tablets and capsules. In solid dosage forms for oral administration (capsules, tablets, pills, dragees, powders, granules, and the like), one or more therapeutic compounds of the present disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof Besides inert diluents, the oral compositions can also include adjuvants such as wetting agents, emulsifying and suspending agents, sweetening, flavoring, coloring, perfuming, and preservative agents.

In various embodiments, topical administration of the pharmaceutical compositions either to skin or to mucosal membranes, is contemplated. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface-active agents. Keratolytic agents such as those known in the art may also be included. Examples are salicylic acid and sulfur. Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required. The ointments, pastes, creams and gels may contain, in addition to a subject compound of the disclosure (e.g., an IL-15/IL-15RαSushi-Fc fusion protein), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Additional pharmaceutical compositions contemplated for use herein include formulations involving polypeptides in sustained- or controlled-delivery formulations. In various embodiments, pharmaceutical compositions may be formulated in nanoparticles, as slow release hydrogel, or incorporated into oncolytic viruses. Techniques for formulating a variety of other sustained- or controlled-delivery means, such as liposome carriers, bio-erodible microparticles or porous beads and depot injections, are also known to those skilled in the art.

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the polypeptide is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.0001 mg/kg to up to about 100 mg/kg or more, depending on the factors mentioned above. Polypeptide compositions may be preferably injected or administered subcutaneously or intravenously. Long-acting pharmaceutical compositions may be administered every three to four days, every week, biweekly, or monthly depending on the half-life and clearance rate of the particular formulation. The frequency of dosing will depend upon the pharmacokinetic parameters of the polypeptide in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

The route of administration of the pharmaceutical composition is in accord with known methods, e.g. orally, through injection by intravenous, intraperitoneal, intratumoral, intracerebral (intra-parenchymal), intracerebroventricular, intramuscular, intra-ocular, intraarterial, intraportal, intralesional routes, intramedullary, intrathecal, intravesicular, intraventricular, transdermal, subcutaneous, or intraperitoneal; as well as intranasal, enteral, topical, sublingual, urethral, vaginal, or rectal means, by sustained release systems or by implantation devices. Where desired, the compositions may be administered by bolus injection or continuously by infusion, or by implantation device. Alternatively, or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

Therapeutic Uses

The present disclosure provides for a method of treating cancer cells in a subject, comprising administering to said subject a therapeutically effective amount (either as monotherapy or in a combination therapy regimen) of an IL-15/IL-15RαSushi-Fc fusion protein of the present disclosure in pharmaceutically acceptable carrier, wherein such administration inhibits the growth and/or proliferation of a cancer cell. Specifically, an IL-15/IL-15RαSushi-Fc fusion protein of the present disclosure is useful in treating disorders characterized as cancer. Such disorders include, but are not limited to solid tumors, such as cancers of the breast, respiratory tract, brain, reproductive organs, digestive tract, urinary tract, eye, liver, skin, head and neck, thyroid, parathyroid and their distant metastases, lymphomas, sarcomas, multiple myeloma and leukemia. Examples of breast cancer include, but are not limited to invasive ductal carcinoma, invasive lobular carcinoma, ductal carcinoma in situ, and lobular carcinoma in situ. Examples of cancers of the respiratory tract include but are not limited to small-cell and non-small-cell lung carcinoma, as well as bronchial adenoma and pleuropulmonary blastoma. Examples of brain cancers include but are not limited to brain stem and hypothalamic glioma, cerebellar and cerebral astrocytoma, neuroblastoma, medulloblastoma, ependymoma, as well as neuroectodermal and pineal tumor. Tumors of the male reproductive organs include but are not limited to prostate and testicular cancer. Tumors of the female reproductive organs include, but are not limited to endometrial, cervical, ovarian, vaginal, and vulvar cancer, as well as sarcoma of the uterus. Tumors of the digestive tract include, but are not limited to anal, colon, colorectal, esophageal, gallbladder, gastric, liver, breast, pancreatic, rectal, small-intestine, and salivary gland cancers. Tumors of the urinary tract include, but are not limited to bladder, penile, kidney, renal pelvis, ureter, and urethral cancers. Eye cancers include but are not limited to intraocular melanoma and retinoblastoma. Examples of liver cancers include but are not limited to hepatocellular carcinoma (liver cell carcinomas with or without fibrolamellar variant), cholangiocarcinoma (intrahepatic bile duct carcinoma), and mixed hepatocellular cholangiocarcinoma. Skin cancers include, but are not limited to squamous cell carcinoma, Kaposi's sarcoma, malignant melanoma, Merkel cell skin cancer, and non-melanoma skin cancer. Head-and-neck cancers include, but are not limited to nasopharyngeal cancer, and lip and oral cavity cancer. Lymphomas include, but are not limited to AIDS-related lymphoma, non-Hodgkin's lymphoma, cutaneous T-cell lymphoma, Hodgkin's disease, and lymphoma of the central nervous system. Sarcomas include but are not limited to sarcoma of the soft tissue, osteosarcoma, malignant fibrous histiocytoma, lymphosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia. In certain embodiments, the cancer will be a cancer with high expression of TGF-β family member, such as activin A, myostatin, TGF-β and GDF15, e.g., pancreatic cancer, gastric cancer, ovarian cancer, colorectal cancer, melanoma leukemia, lung cancer, prostate cancer, brain cancer, bladder cancer, and head-neck cancer.

The present disclosure provides for a method of treating refractory or resistance liquid or solid tumors through enhancing the therapeutic effect of existing cancer therapeutics as an adjuvant.

The present disclosure also provides for a method of treating viral infection including hepatitis A, hepatitis B, hepatitis C, AIDS in HIV infection, human papillomavirus (HPV) infection, genital warts, etc. in a subject, comprising administering to human patient in need of an IL-15/IL-15RαSushi-Fc fusion protein of the present disclosure in pharmaceutically acceptable carrier, wherein such administration inhibits the growth and/or replication of virus.

Therapeutically effective amount" or "therapeutically effective dose" refers to that amount of the therapeutic agent being administered which will relieve to some extent one or more of the symptoms of the disorder being treated.

A therapeutically effective dose can be estimated initially from cell culture assays by determining an $IC_{50}$. A dose can then be formulated in animal models to achieve a circulating plasma concentration range that includes the $IC_{50}$ as determined in cell culture. Such information can be used to more accurately determine useful doses in humans. Levels in plasma may be measured, for example, by HPLC. The exact composition, route of administration and dosage can be chosen by the individual physician in view of the subject's condition.

Dosage regimens can be adjusted to provide the optimum desired response (e.g., a therapeutic or prophylactic response). For example, a single bolus can be administered, several divided doses (multiple or repeat or maintenance) can be administered over time and the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the present disclosure will be dictated primarily by the unique characteristics of the antibody and the particular therapeutic or prophylactic effect to be achieved.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a subject may also be determined, as can the temporal requirements for administering each agent to provide a detectable therapeutic benefit to the subject. Accordingly, while certain dose and administration regimens are exemplified herein, these examples in no way limit the dose and administration regimen that may be provided to a subject in practicing the present disclosure.

It is to be noted that dosage values may vary with the type and severity of the condition to be alleviated and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this disclosure may be based on a variety of factors, including the type of disease, the age, weight, sex, medical condition of the subject, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present disclosure encompasses intra-subject dose-escalation as determined by the skilled artisan. Determining appropriate dosages and regimens are well-known in the relevant art and would be understood to be encompassed by the skilled artisan once provided the teachings disclosed herein.

An exemplary, non-limiting daily dosing range for a therapeutically or prophylactically effective amount of an IL-15/IL-15RαSushi-Fc fusion protein of the disclosure can be 0.0001 to 100 mg/kg, 0.0001 to 90 mg/kg, 0.0001 to 80 mg/kg, 0.0001 to 70 mg/kg, 0.0001 to 60 mg/kg, 0.0001 to 50 mg/kg, 0.0001 to 40 mg/kg, 0.0001 to 30 mg/kg, 0.0001 to 20 mg/kg, 0.0001 to 10 mg/kg, 0.0001 to 5 mg/kg, 0.0001 to 4 mg/kg, 0.0001 to 3 mg/kg, 0.0001 to 2 mg/kg, 0.0001 to 1 mg/kg, 0.0010 to 50 mg/kg, 0.0010 to 40 mg/kg, 0.0010 to 30 mg/kg, 0.0010 to 20 mg/kg, 0.0010 to 10 mg/kg, 0.0010 to 5 mg/kg, 0.0010 to 4 mg/kg, 0.0010 to 3 mg/kg, 0.0010 to 2 mg/kg, 0.0010 to 1 mg/kg, 0.01 to 50 mg/kg, 0.01 to 40 mg/kg, 0.01 to 30 mg/kg, 0.01 to 20 mg/kg, 0.01 to 10 mg/kg, 0.01 to 5 mg/kg, 0.01 to 4 mg/kg, 0.01 to 3 mg/kg, 0.01 to 2 mg/kg, 0.01 to 1 mg/kg, 0.1 to 50 mg/kg, 0.1 to 40 mg/kg, 0.1 to 30 mg/kg, 0.1 to 20 mg/kg, 0.1 to 10 mg/kg, 0.1 to 5 mg/kg, 0.1 to 4 mg/kg, 0.1 to 3 mg/kg, 0.1 to 2 mg/kg, or 0.1 mg/kg, 1 to 50 mg/kg, 1 to 40 mg/kg, 1 to 30 mg/kg, 1 to 20 mg/kg, 1 to 10 mg/kg, 1 to 5 mg/kg, 1 to 4 mg/kg, 1 to 3 mg/kg, 1 to 2 mg/kg, or 1 to 1 mg/kg body weight. It is to be noted that dosage values may vary with the type and severity of the conditions to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Toxicity and therapeutic index of the pharmaceutical compositions of the disclosure can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effective dose is the therapeutic index and it can be expressed as the ratio $LD_{50}/ED_{50}$. Compositions that exhibit large therapeutic indices are generally preferred.

The dosing frequency of the administration of the IL-15/IL-15RαSushi-Fc fusion protein pharmaceutical composition depends on the nature of the therapy and the particular disease being treated. The subject can be treated at regular intervals, such as weekly or monthly, until a desired therapeutic result is achieved. Exemplary dosing frequencies include, but are not limited to: once or twice a week without break; once or twice a week, every other week; once every 2 weeks; once every 3 weeks; weakly without break for 2 weeks, then monthly; weakly without break for 3 weeks, then monthly; monthly; once every other month; once every three months; once every four months; once every five months; or once every six months, or yearly.

Combination Therapy

As used herein, the terms "co-administration", "co-administered" and "in combination with", referring to an IL-15/IL-15RαSushi-Fc fusion protein of the disclosure and one or more other therapeutic agents, is intended to mean, and does refer to and include the following: simultaneous administration of such combination of an IL-15/IL-15RαSushi-Fc fusion protein of the disclosure and therapeutic agent(s) to a subject in need of treatment, when such components are formulated together into a single dosage form which releases said components at substantially the same time to said subject; substantially simultaneous administration of such combination of an IL-15/IL-15RαSushi-Fc fusion protein of the disclosure and therapeutic agent(s) to a subject in need of treatment, when such components are formulated apart from each other into separate dosage forms which are taken at substantially the same time by said subject, whereupon said components are released at substantially the same time to said subject; sequential administration of such combination of an IL-15/IL-15RαSushi-Fc fusion protein of the disclosure and therapeutic agent(s) to a subject in need of treatment, when such components are formulated apart from each other into separate dosage forms which are taken at consecutive times by said subject with a significant time interval between each administration, whereupon said components are released at substantially different times to said subject; and sequential administration of such combination of an IL-15/IL-15RαSushi-Fc fusion protein of the disclosure and therapeutic agent(s) to a subject in need of treatment, when such components are formulated together into a single dosage form which releases said components in a controlled manner whereupon they are concurrently, consecutively, and/or overlappingly released at the same and/or different times to said subject, where each part may be administered by either the same or a different route.

In another aspect, the present disclosure provides a method for treating cancer or cancer metastasis in a subject, comprising administering a therapeutically effective amount of the pharmaceutical compositions of the invention in combination with a second therapy, including, but not limited to immunotherapy, cytotoxic chemotherapy, small molecule kinase inhibitor targeted therapy, surgery, radiation therapy, and stem cell transplantation. For example, such methods can be used in prophylactic cancer prevention, prevention of cancer recurrence and metastases after surgery, and as an adjuvant of other conventional cancer therapy. The present disclosure recognizes that the effectiveness of conventional cancer therapies (e.g., chemotherapy, radiation therapy, phototherapy, immunotherapy, and surgery) can be enhanced through the use of the combination methods described herein.

A wide array of conventional compounds has been shown to have anti-neoplastic activities. These compounds have been used as pharmaceutical agents in chemotherapy to shrink solid tumors, prevent metastases and further growth, or decrease the number of malignant T-cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

In various embodiments, a second anti-cancer agent, such as a chemotherapeutic agent, will be administered to the patient. The list of exemplary chemotherapeutic agent includes, but is not limited to, daunorubicin, dactinomycin, doxorubicin, bleomycin, mitomycin, nitrogen mustard, chlorambucil, melphalan, cyclophosphamide, 6-mercaptopurine, 6-thioguanine, bendamustine, cytarabine (CA), 5-fluorouracil (5-FU), floxuridine (5-FUdR), methotrexate (MTX), colchicine, vincristine, vinblastine, etoposide, teniposide, cisplatin, carboplatin, oxaliplatin, pentostatin, cladribine, cytarabine, gemcitabine, pralatrexate, mitoxantrone, diethylstilbestrol (DES), fluradabine, ifosfamide, hydroxyureataxanes (such as paclitaxel and doxetaxel) and/or anthracycline antibiotics, as well as combinations of agents such as, but not limited to, DA-EPOCH, CHOP, CVP or FOLFOX. In various embodiments, the dosages of such chemotherapeutic agents include, but is not limited to, about any of 10 mg/m$^2$, 20 mg/m$^2$, 30 mg/m$^2$, 40 mg/m$^2$, 50 mg/m$^2$, 60 mg/m$^2$, 75 mg/m$^2$, 80 mg/m$^2$, 90 mg/m$^2$, 100 mg/m$^2$, 120 mg/m$^2$, 150 mg/m$^2$, 175 mg/m$^2$, 200 mg/m$^2$, 210 mg/m$^2$, 220 mg/m$^2$, 230 mg/m$^2$, 240 mg/m$^2$, 250 mg/m$^2$, 260 mg/m$^2$, and 300 mg/m$^2$.

In various embodiments, the combination therapy methods of the present disclosure may further comprise administering to the subject a therapeutically effective amount of immunotherapy, including, but are not limited to, treatment using depleting antibodies to specific tumor antigens; treatment using antibody-drug conjugates; treatment using agonistic, antagonistic, or blocking antibodies to co-stimulatory or co-inhibitory molecules (immune checkpoints) such as CD276, CD272, CTLA-4, PD-1, PD-L1, CD40, SIRPa, CD47, OX-40, CD137, GITR, LAGS, ICOS, CD27, 4-1BB, TIM-3, B7-H4, Siglec 7, Siglec 8, Siglec 9, Siglec 15 and VISTA; treatment using bispecific T cell engaging antibodies (BiTE®) such as blinatumomab: treatment involving administration of biological response modifiers such as IL-2, IL-7, IL-12, IL-21, GM-CSF, IFN-α, IFN-8 and IFN-γ; treatment using therapeutic vaccines such as sipuleucel-T; treatment using dendritic cell vaccines, or tumor antigen peptide vaccines; treatment using NK cells; treatment using TCR-T cells; treatment using chimeric antigen receptor (CAR)-T cells; treatment using CAR-NK cells; treatment using iPS induced-NK cells, iPS induced TCR-T cells, iPS induced CAR-T cells or iPS induced CAR-NK cells; treatment using dendric cells; treatment using tumor infiltrating lymphocytes (TILs); treatment using adoptively transferred anti-tumor T cells (ex vivo expanded and/or TCR transgenic); treatment using vaccine such as Bacille Calmette-Guerine (BCG); treatment using TALL-104 cells; and treatment using immunostimulatory agents such as Toll-like receptor (TLR) agonists CpG, and imiquimod; wherein the combination therapy provides increased effector cell killing of tumor cells, i.e., a synergy exists between the IL-15/IL-15RαSushi-Fc fusion proteins and the immunotherapy when co-administered.

In various embodiments, the combination therapy comprises administering an IL-15/IL-15RαSushi-Fc fusion protein and the second agent composition simultaneously, either in the same pharmaceutical composition or in separate pharmaceutical composition. In various embodiments, an IL-15/IL-15RαSushi-Fc fusion protein composition and the second agent composition are administered sequentially, i.e., an IL-15/IL-15RαSushi-Fc fusion protein composition is administered either prior to or after the administration of the second agent composition. In various embodiments, the administrations of an IL-15/IL-15RαSushi-Fc fusion protein composition and the second agent composition are concurrent, i.e., the administration period of an IL-15/IL-15RαSushi-Fc fusion protein composition and the second agent composition overlap with each other. In various embodiments, the administrations of an IL-15/IL-15RαSushi-Fc fusion protein composition and the second agent composition are non-concurrent. For example, in various embodiments, the administration of an IL-15/IL-15RαSushi-Fc fusion protein composition is terminated before the second agent composition is administered. In various embodiments, the administration second agent composition is terminated before an IL-15/IL-15RαSushi-Fc fusion protein composition is administered.

The following examples are offered to more fully illustrate the disclosure but are not construed as limiting the scope thereof.

EXAMPLE 1

Construction, Expression, and Purification of IL-15/IL-15RαSushi-Fc Fusion Proteins All genes were codon optimized for expression in mammalian cells, which were synthesized and subcloned into the recipient mammalian expression vector (GenScript). Protein expression is driven by an CMV promoter and a synthetic SV40 polyA signal sequence is present at the 3' end of the CDS. A leader sequence has been engineered at the N-terminus of the constructs to ensure appropriate signaling and processing for secretion. The fusion proteins were produced by co-transfecting HEK293-F cells growing in suspension with the mammalian expression vectors using polyethylenimine (PEI, 25,000 MW linear, Polysciences). If there were two or more expression vectors, the vectors will be transfected in a 1:1 ratio. For transfection, HEK293 cells were cultivated in serum free FreeStyle™ 293 Expression Medium (ThermoFisher). For production in 1000 ml shaking flasks (maximum working volume 330 mL), HEK293 cells at density of $0.8 \times 10^6$ cells/ml were seeded 24 hours before transfection. Expression vectors to a total amount of 330 µg DNA were mixed with 16.7 ml Opti-mem Medium (ThermoFisher). After addition of 0.33 mg PEI diluted in 16.7 ml Opti-mem Medium, the mixture was vortexed for 15 seconds and subsequently incubated for 10 min at room temperature. The DNA/PEI solution was then added to the cells and incubated at 37° C. in an incubator with 8% $CO_2$ atmosphere. Sodium butyrate (Millipore Sigma) at the final concentration of 2 mg/L was added to the cell culture at day 4 to help sustain protein expression. After 6 days cultivation, supernatant was collected for purification by centrifugation for 20 min at 2200 rpm. The solution was sterile filtered (0.22 µm filter, Corning). The secreted protein was purified from cell culture supernatants using Protein A affinity chromatography.

The secreted protein was purified from cell culture supernatants using Protein A affinity chromatography. Cell culture supernatant was loaded onto a HiTrap MabSelect SuRe 5 ml column (GE Healthcare) equilibrated with 5 column volumes (CV) of phosphate buffered saline, pH 7.2 (ThermoFisher). Unbound protein was removed by washing with 5 CVs PBS pH 7.2, and target protein was eluted with 25 mM sodium citrate, 25 mM sodium chloride, pH 3.2. Protein solution was neutralized by adding 3% of 1 M Tris pH 10.2. Target protein was concentrated and buffer exchanged to PBS, pH 7.2 using Amicon® Ultra-15 Ultracel 10K (Merck Millipore)

Purity and molecular weight of the purified molecules were analyzed by SDS-PAGE in the presence and absence of a reducing agent and staining with Coomassie (Imperial™ protein stain, ThermoFisher). The NuPAGE® Pre-Cast gel system (4-12% Bis-Tris, ThermoFisher) was used according to the manufacturer's instruction. The aggregate content of the molecules was analyzed on an Agilent 1200 high-performance liquid chromatography (HPLC) system. Samples were injected onto an AdvanceBio size-exclusion column (300 Å, 4.6×150 mm, 2.7 µm, LC column, Agilent) using 150 mM sodium phosphate, pH 7.0 as the mobile phase at 25° C.

The protein concentration of purified protein samples was determined by measuring the absorbance at 280 nm using a Nanodrop spectrophotometer (ThermoFisher) divided by the molar extinction coefficient calculated on the basis of the amino acid sequence. Endotoxin level of purified protein samples were measured using Endosafe nexgen-PTS (Charles River) according to the manufacturer's instruction.

As an example to demonstrate the protein profile of isolated IL-15/IL-15Rα Fc fusion constructs, SDS-PAGE analyses of P-0217, P-0234, and P-0313 are shown in FIG. 2A. P-0217, P-0234, and P-0313 are all IL-15/IL-15Rα (non-covalent)-Fc fusion proteins comprising IL-15/IL-15Rα complex at the C-terminus. P-0217 is a monovalent IL-15/IL-15Rα (non-covalent) Fc fusion, P-0234 is the dimeric counterpart of P-0217, and P-0313 shares the same fusion configuration as P-0234 but differs only with S58D substitution in the IL-15 domain.

The IL-15Rα sushi+ domain with a calculated molecular weight of 8.6 kDa was non-covalently associated with IL-15 or IL-15 variant fused to Fc domain for both monovalent and bivalent Fc fusions, and it was dissociated under denaturing conditions and migrated to the expected position as a sharp band (FIG. 2A). The presence of IL-15Rα-sushi+ band on the gel confirmed the non-covalent association between IL-15 and IL-15Rα during cell culture growth; such association was maintained during Protein A purification under low-pH elution conditions.

Figure 2B:
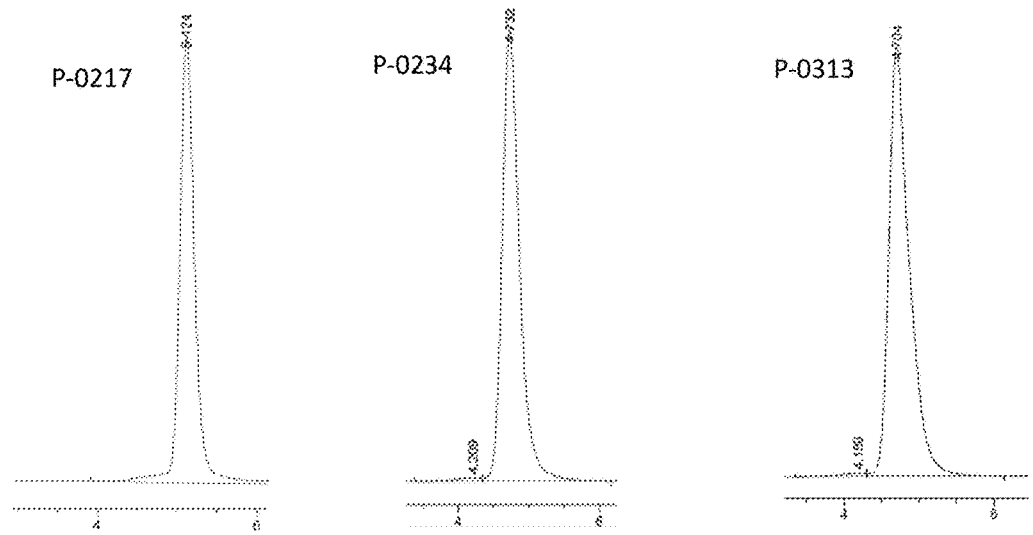

Size exclusion chromatogram in FIG. 2B indicated low aggregation propensity for the two fusion formats as only 1-2% aggregation was present for all three fusion proteins after the initial protein A capture step without polishing step. The sharp main peak further suggests the tight association of IL-15 and IL-15Rα under native buffer conditions.

Further, the expression level of the fusion proteins was comparable (within 2-fold difference) to that of Fc-only protein under the same vector and culturing conditions. The high yield and low aggregation propensity demonstrated favorable developability profile of both monovalent and bivalent of IL-15/IL-15Rα (non-covalent) Fc fusion proteins. Additionally, amino acid substitution in IL-15, exemplified by P-0313, did not impact expression profile of the fusion protein; P-0313 exhibited almost identical purity and aggregation propensity as its wild type equivalent P-0234 (FIG. 2).

EXAMPLE 2

Purity-Focused Developability Assessment of Different Fusion Protein Formats Underscored the Role of Properly Complexed IL-15Rα Domain in Enhancing Fusion Protein Developability Profile SEC analysis of the protein A purified samples was used to assess the impact of different fusion formats on protein aggregation propensity and purity. It was the observation of the inventors that while protein expression level may vary between different batches due to cell growth variations, protein aggregation propensity and purity seemed to be an intrinsic property associated with a particular protein with little variance from lot to lot, as exemplified by FIGS. 3F and 3H for P-0234.

First, the impact of complexation of IL-15Rα on protein purity of IL-15-Fc fusion proteins were evaluated based on 5 molecules. P-0162 is a C-terminal monomeric IL-15 alone Fc fusion protein containing a Hole-Fc-Linker1-IL-15 chain (SEQ ID NO: 13) and an empty Knob-Fc chain (SEQ ID NO: 7). P-0197 is a C-terminal monovalent IL-15/IL-15Rα (non-covalent) Fc fusion with its schematic diagram depicted in FIG. 1B. P-0197 differs from P-0162 only by the presence of a free IL-15RαSushi+domain that is non-covalently complexed with IL-15. P-0153 is a N-terminal monomeric IL-15/IL-15Rα fusion with the heterodimeric Fc fusion format with its cartoon diagram shown in FIG. 1A. P-0167 and P-0198 are the dimer counterparts of P-0162 and P-0197, respectively. The size exclusion diagrams of the 5 molecules are illustrated in FIG. 3A-3E.

Figure 3A:
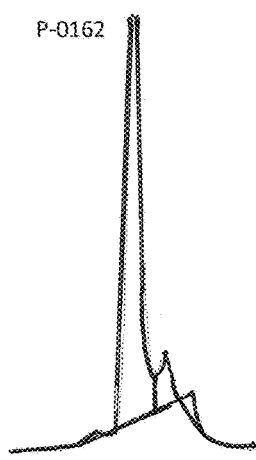
FIG. 3 depicts the SEC chromatograms of several the IL-15/IL-15Rα-Fc fusion proteins of different configurations. These exemplary fusion proteins all comprise IL-15/IL-15Rα complex at the C-terminus unless otherwise stated. P-0162 is a monomeric IL-15 alone Fc fusion protein. P-0197 is a monovalent IL-15/IL-15Rα (non-covalent) Fc fusion with its schematic diagram depicted in FIG. 1B. P-0153 is a monomeric IL-15/IL-15Rα fusion with the heterodimeric Fc fusion format (FIG. 1A). P-0167 and P-0198 are the dimeric counterparts of P-0162 and P-0197, respectively. P-0234, and P-0220, and P-0223 are all bivalent IL-15/IL-15Rα (non-covalent) Fc fusion Proteins (FIG. 1C). P-0220 contains IL-15RαECD, P-0234 contains IL-15RαSushi+domain; P-0223 differs from P-0234 with its IL-15/IL-15Rα complex attached to the N-terminus of Fc.
Figure 3B:
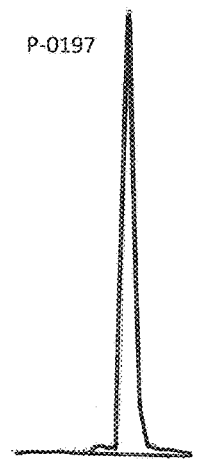
Figure 3C:
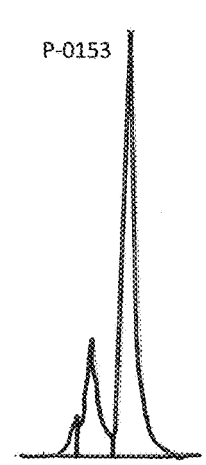
Figure 3D:
Figure 3E:
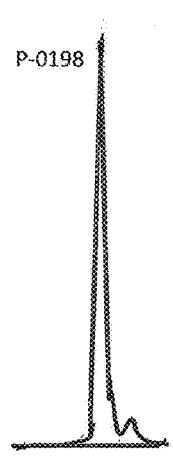

As seen in FIG. 3A, IL-15-Fc monomeric fusion without IL-15Rα has a monomer content of 84.5% and the majority of impurities are of lower molecular weights. In contrast, P-0197 contains 98.6% monomer content (FIG. 3B), and such significantly improvement in protein was apparently contributed from the free IL-15RαSushi+domain. The effect of free IL-15RαSushi+domain on the protein quality of IL-15-Fc fusion proteins were further highlighted for the dimeric formats, which is depicted with P-0167 and P-0198 SEC chromatograms in FIGS. 3D and 3E, respectively. P-0167 contains a broad and irregular peak with shoulders on both sides of the main peak. More notably, P-0167 did not show any ex vivo activity in activating NK and T cells of fresh human PBMC, which was likely due to the incorrect folding of the protein. However, P-0198, which contains a non-covalently bound IL-15RαSushi+domain in dimeric form, demonstrated a sharp main peak with 90.5% monomer content (FIG. 3E). Somewhat intriguing, if the IL-15RαSushi+domain was not free, but covalently fused to a matching heterodimeric Fc as in P-0153, its complexation with IL-15-Fc did not yield any improvement in protein purity; rather, the protein sample contains >25% dimer and higher molecular weight soluble aggregates (FIG. 3C). Fusion of both IL-15 and IL-15Rα to Fc domains likely created spatial constrains that prevented them from interacting in the physiological way. In summary, IL-15RαSushi+domain can significantly improve IL-15-Fc fusion protein purity and biophysical property, but only when IL-15Rα domain can associate with IL-15 in a favorable and unconstrained manner.

Figure 3F:
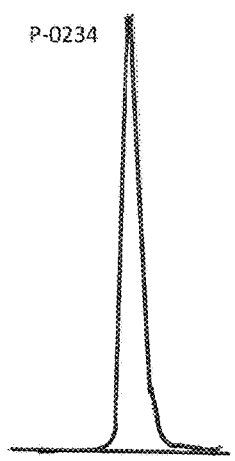
Figure 3G:
Figure 3H:

Second, the effect of IL-15RαECD (SEQ ID NO: 4) vs. IL-15RαSushi+ (SEQ ID NO: 5) on the developability of IL-15/IL-15Rα-Fc fusion proteins were evaluated by comparing P-0234 and P-0220. Both constructs are C-terminal Fc fusion sharing the same configuration as depicted in FIG. 1C with IL-15RαSushi+domain in P-0234, and IL-15RαECD in P-0220. Their SEC chromatograms are shown in FIGS. 3F and 3G, respectively. P-0220, the protein comprising IL-15RαECD domain, not only has a lower purity than its IL-15RαSushi+-containing counterpart P-0234 (88.5% vs. 100%), but also expressed at a 2.5-fold lower level in the same batch of cells. In short, it is evident that IL-15RαSushi+domain is a preferred partner over IL-15RαECD in constructing more developable IL-15/IL-15Rα-Fc fusion proteins.

Figure 3I:

Further, the impact of fusion terminus on the developability of IL-15/IL-15Rα-Fc fusion proteins was evaluated. P-0234 and P-0223 are dimeric IL-15/IL-15Rα (non-covalent) Fc fusion proteins with the IL-15/IL-15RαSushi complex attached to the C-terminus and N-terminus of Fc, respectively. Their SEC chromatograms (FIGS. 3H and 3I) show rather subtle difference in purity (98.5% vs. 93.9%). However purified P-0223 consistently contains a broad peak of higher molecular weight species and a small but appreciable peak containing lower molecular impurities, which were virtually absent in P-0234. Despite the small differences, P-0234 with C-terminal fusion has unarguably better SEC purity profile and is the preferred format from developability point of view considering that both molecules expressed at a comparable level.

In conclusion, complexing IL-15Rα subunit with IL-15-Fc fusion can significantly improve expression, purity, and reduce aggregation; and such improvement requires proper IL-15Rα association with IL-15 with minimal spatial constrains. And IL-15RαSushi+, the truncated version of IL-15Rα ECD, appeared to be preferred over the full length ECD based on both productivity and purity assessment. Further, placing IL-15/IL-15Rα complex to the C-terminus of Fc is advantageous over N-terminus fusion to achieve high purity. Consequently, the dimeric IL-15/IL-15Rα (non-covalent)C-terminal Fc fusion format, exemplified by P-0234, integrates all the preferable components and represents the superior format.

EXAMPLE 3

Non-Covalent Association of IL-15Rα Enhances Receptor Binding and Biological Activities of IL-15/IL-15Rα Fc Fusion Proteins IL-15 binds to its specific receptor IL-15Rα with high affinity and both are expressed on antigen presenting cells. The association of IL-15Rα with IL-15 trans-presents IL-15 to a heterodimeric receptor complex composed of IL-15Rβ and $\gamma_c$ on the responding lymphocytes, including NK, T and B cells. The formation of the ligand-trimeric receptor complex (IL-15-IL-15Rαβγ) initiates intracellular signaling cascades leading to downstream biological effects. The complexity of the IL-15 receptor biology eludes challenges to engineer an optimal IL-15 fusion protein that enables a conformationally effective ligand-trimeric receptor signaling complex.

We hypothesized that the covalent linkage of IL-15 to the Fc portion of the human IgG either at the N-terminus or C-terminus would be more advantageous for in vivo half-life extension than IL-15 in non-covalent association with an IL-15Rα Fc fusion protein. We further postulated that IL-15Rα domain is required for IL-15 Fc fusion protein to enhance its interaction with the intermediate affinity IL-2Rβγ receptor and facilitate the formation of high affinity ligand-trimeric receptor signaling complex. Furthermore, we believe that the non-covalent association of IL-15Rα domain with the IL-15 Fc fusion protein retains a natural IL-15 and IL-15Rα association and an optimal conformation for IL-15 trans-presentation. Moreover, we hypothesized it is feasible to produce such a fusion protein complex due to the extremely high binding affinity between IL-15 and IL-15Rα domain.

Different formats of IL-15 Fc fusion proteins containing IL-15/IL-15Rα domain complex in various configurations were constructed. The binding activity of the fusion proteins to IL-15Rβ subunit was determined and their biological activity in stimulating lymphocyte activation was analyzed by measuring CD69 expression on human CD8 and NK cells. The exemplary structural diagrams of the fusion proteins are shown in FIG. 1.

The binding activity was tested in ELISA assay. Briefly, Nunc Maxisorp (ThermoFisher) plates were coated overnight at 4° C. with huIL-15Rβ-6His at 1 μg/well (100 μl/well) in bicarbonate buffer pH 9.4 (ThermoFisher). After washing 3 times with PBS/0.05% Tween20, plates were incubated with SuperBlock (300 μl/well) at room temperature for 2 hrs. to block nonspecific binding. After washing, IL-15 compounds each at 3-fold serial dilutions with blocking buffer were added to the plates (100 μl/well) and incubated at room temperature for 1 hr. After washing, the Fc fusions were detected by 1 hr. incubation at room temperature with a goat anti-human IgG Fc secondary antibody conjugated with horseradish peroxidase (HRP) at 1:5000 dilution in blocking buffer (ThermoFisher) (100 μl/well). After washing, TMB substrate (ThermoFisher) was added (100 ul/well). Plates were sealed and incubated 5-20 min at room temperature in dark. Reaction was stopped by adding 2N sulfuric acid (Ricca Chemical) (50 uL/well) and absorbance was read at 450-590 nm.

The biological activity was determined by measuring the induction of CD69 expression on human NK and CD8 T cells. CD69 is a cell surface glycoprotein that is early induced during lymphocyte activation. An ex vivo human peripheral blood mononuclear cell (PBMC) assay was established to analyze the number/percent of NK or CD8 T cells expressing CD69 following IL-15 treatment. Specifically, human PBMCs were isolated by Ficoll-Hypaque centrifugation from the buffy coat purchased from Blood Oklahoma Institute. Purified human PBMCs were treated with serial dilutions of each IL-15 test compound and incubated at 37° C. for 48 hours. Cells were collected by 300G centrifugation and resuspended in FACS buffer. After blocking Fc receptor by adding human TruStain FcX (1:50 dilution), cells were stained with anti-human CD56-FITC, anti-human CD69-PE and anti-human CD8-APC antibodies (1:50 dilution). After 30-minutes incubation with the antibodies at room temperature, cells were collected and washed, resuspended in FACS buffer and ready for the flow cytometric analysis. CD69 expression was determined on CD56+NK and CD8+ T cells and data are expressed as of CD69 positive cells in gated population.

Figure 4:
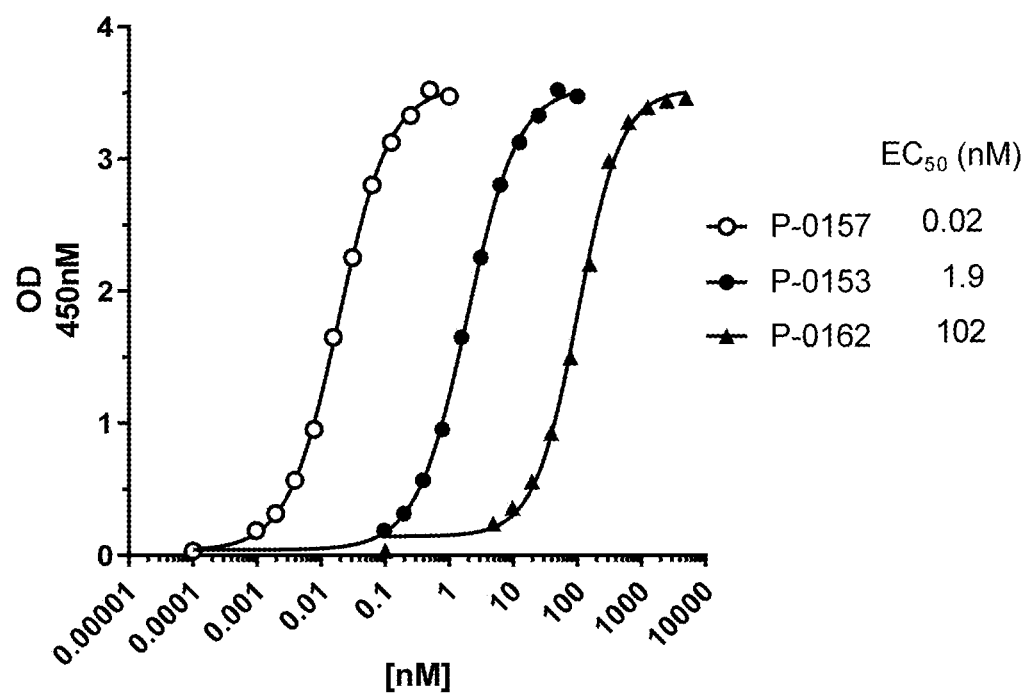
FIG. 4 depicts the effect of different IL-15/IL-15Rα Fc fusion formats on the binding activity to IL-15Rβ in ELISA assay. IL-15Rα is demonstrated to increase IL-15Rβ binding activity of IL-15 Fc fusion proteins. P-0157 (open circle) is a N-terminal bivalent IL-15 (non-covalent)/IL-15RαSushi Fc fusion protein; P-0153 (closed circle) is a C-terminal IL-15/IL-15RαSushi heterodimeric Fc fusion protein; P-0162 (closed triangular) is a C-terminal monovalent IL-15 Fc fusion protein without IL-15RαSushi complexed.

P-0157 is an N-terminal bivalent IL-15 (non-covalent)/IL-15RαSushi Fc fusion protein; P-0153 is a C-terminal IL-15/IL-15RαSushi heterodimeric Fc fusion protein; P-0162 is a C-terminal monovalent Fc-IL-15 fusion protein without IL-15RαSushi complexed. An ELISA binding assay indicated that the incorporation of IL-15RαSushi domain significantly increased the binding strength of the IL-15 Fc fusion proteins (P-0157 & P0153) to the IL-15Rβ as compared to the fusion protein without the IL-15Rα complexed (P-0162) (FIG. 4), suggesting the essential role of IL-15Rα in facilitating the fusion proteins' interaction with the receptor. Furthermore, the receptor binding activity was reduced when both IL-15 and IL-15Rα were covalently conjugated to the Fc in a heterodimeric form (P-0153) as opposed to IL-15 bounded non-covalently to IL-15Rα Fc fusion protein (P-0157) (FIG. 4), suggesting a conformationally constrained fusion format would negatively affect the receptor binding activity.

Figure 5A:
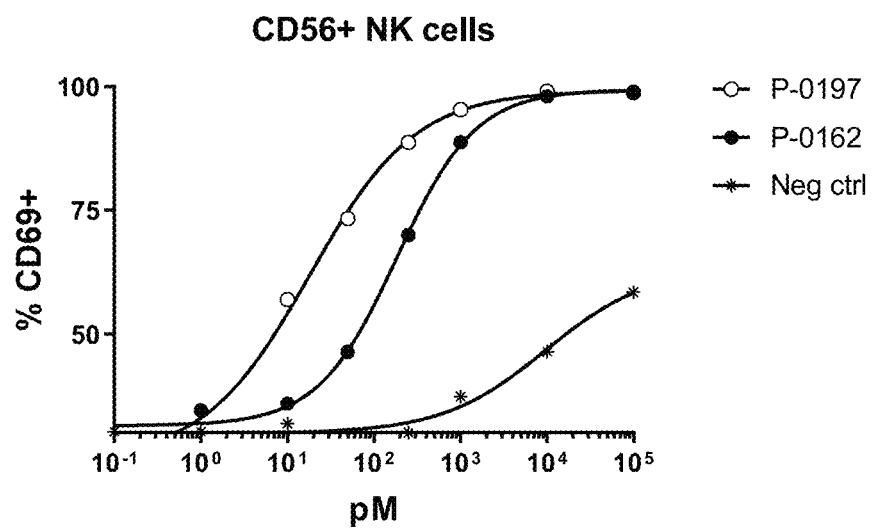
FIG. 5 depicts the effect of IL-15Rα on the biological activity of IL-15 Fc fusion proteins. IL-15Rα is demonstrated to enhance the biological activity of IL-15 Fc fusion proteins. Induction of CD69 positive NK (FIG. 5A) and CD8 T (FIG. 5B) cells was measured in an ex vivo human PBMC FACS based assay. P-0197 (open circle) is a C-terminal monovalent IL-15/IL-15RαSushi (non-covalent) Fc fusion protein; P-0162 (closed circle) is a fusion protein with the same structure as P-0197 without IL-15RαSushi complexed.
Figure 5B:
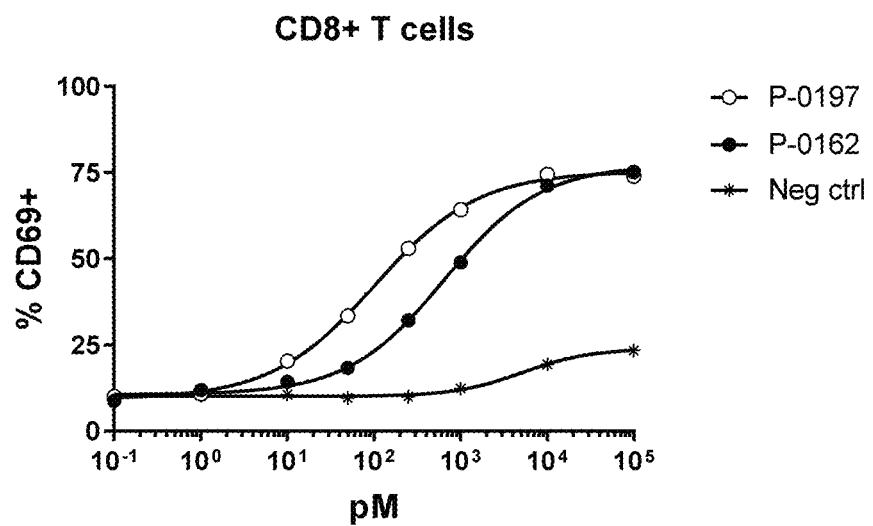

Consistent with the binding potency, the incorporation of IL-15Rα also increased the biological activity of the IL-15 fusion protein as compared to the fusion protein without IL-15Rα. P-0197 is a C-terminal monovalent IL-15/IL-15Rα (non-covalent) Fc fusion protein and P-0162 share the same structure as P-0197 without IL-15Rα sushi included. P-0197 demonstrated 10-fold and 6-fold increased potency in induction of CD69 positive NK cells (FIG. 5A) and CD8 T cells (FIG. 5B) compared to P-0162, respectively, attributed to the inclusion of IL-15Rα.

Figure 6A:
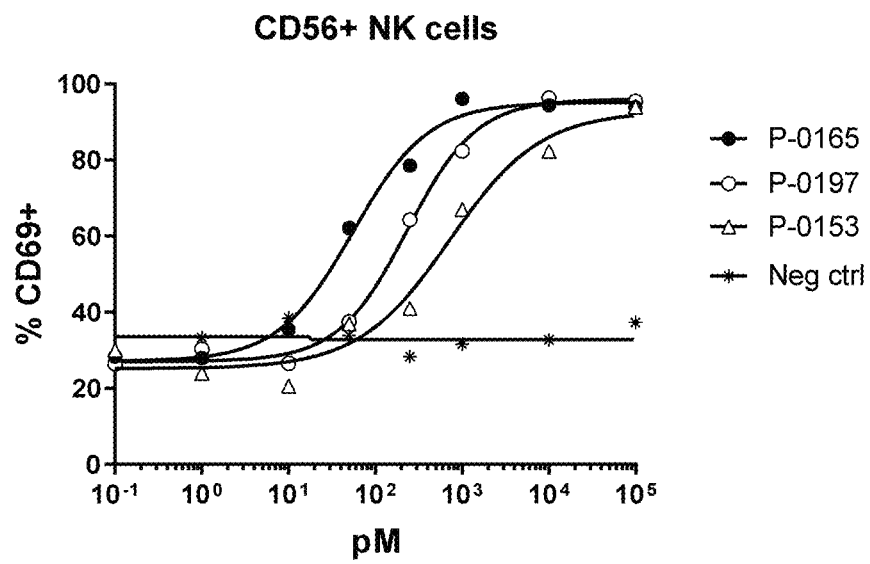
FIG. 6 depicts the effect of different configurations of IL-15/IL-15Rα complexation on the biological activity of IL-15 Fc fusion proteins. Induction of CD69 positive NK (FIG. 6A) and CD8+ T (FIG. 6B) cells was measured in an ex vivo human PBMC FACS based assay. P-0165 (closed circle) is a C-terminal monovalent IL-15 (non-covalent)/IL-15Rα Fc fusion protein; P-0197 (open circle) is a C-terminal monovalent IL-15/IL-15Rα (non-covalent) Fc fusion protein; P-0153 (open triangular) is a C-terminal IL-15/IL-15Rα heterodimeric Fc fusion protein.
Figure 6B:
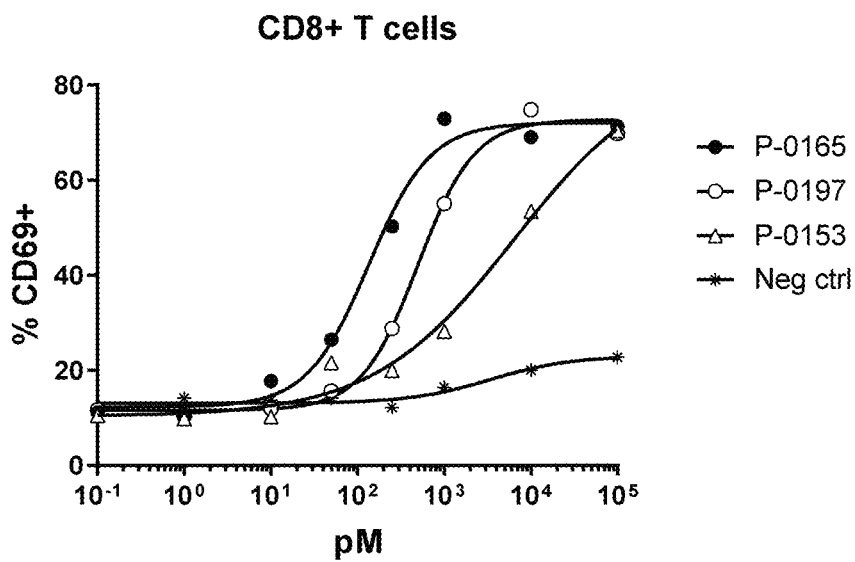

Lastly, the biological activity of three C-terminal monovalent IL-15/IL-15Rα Fc fusion proteins was compared. P-0165 is an Fc fusion protein with IL-15Rα fused to the Fc domain and IL-15 non-covalently bound; P-0197 is configured reversely with IL-15 fused to the Fc domain and IL-15Rα non-covalently bound; P-0153 has a heterodimeric structure with both IL-15 and IL-15Rα fused to the Fc domain. As shown in FIG. 6, the fusion proteins with non-covalent complexation with either IL-15 or IL-15Rα demonstrated better potency in induction of CD69 positive NK (FIG. 6A) and CD8 T cells (FIG. 6B) than the fusion protein with both IL-15/IL-15Rα covalently and heterodimerically fused to Fc. Data suggest a conformationally optimal association between IL-15 and IL-15Rα is critical for IL-15 fusion protein to bind its receptor and exert its biological activity. Increased conformational constrains, e.g. the heterodimeric Fc fusion format, negatively affect the biological activity.

EXAMPLE 4

Effect of Linker on the Activity of IL-15/IL-15Rα Fc Fusion Proteins

Selection of a suitable linker to join the protein domains is critical in fusion protein engineering. The peptide linker not only provides a spatial distance between the fusion protein domains and allows their independent folding, but also directly affects the structural stability and functional property of the fusion proteins. Here we examine the effect of flexibility and length of a linker on the biological activity of IL-15/IL-15Rα Fc fusion proteins.

Figure 7A:
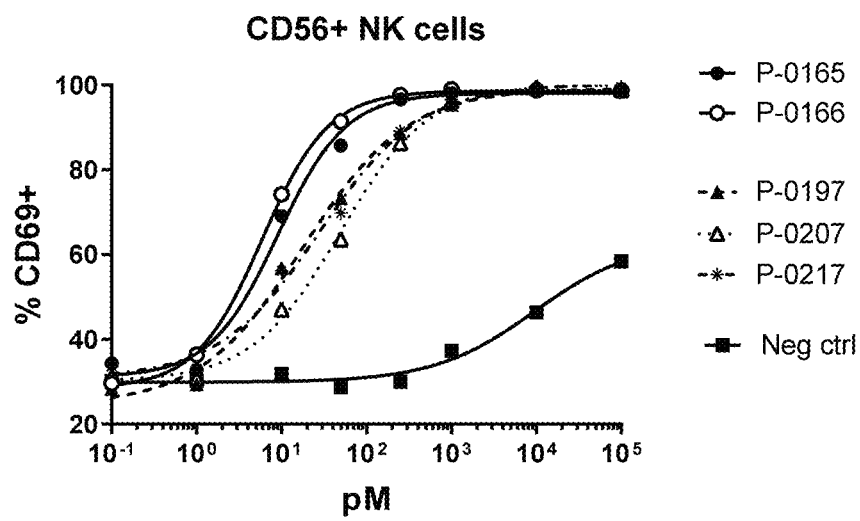
FIG. 7 depicts the effect of linkers on the biological activity of IL-15/IL-15Rα Fc fusion proteins at different formats. Induction of CD69 positive NK (FIG. 7A) and CD8 T (FIG. 7B) cells was measured in an ex vivo human PBMC FACS based assay. P-0165 (closed circle) & P-0166 (open circle) are monovalent IL-15 (non-covalent)/IL-15Rα Fc fusions with a fifteen-amino acid rigid linker and ten-amino acid flexible linker, respectively. P-0197 (closed triangular), P-0207 (open triangular), and P-0217 (star) are monovalent IL-15/IL-15Rα (non-covalent) Fc fusion proteins with a rigid, 10-aa and 15-aa GS rich flexible linker, respectively.
Figure 7B:
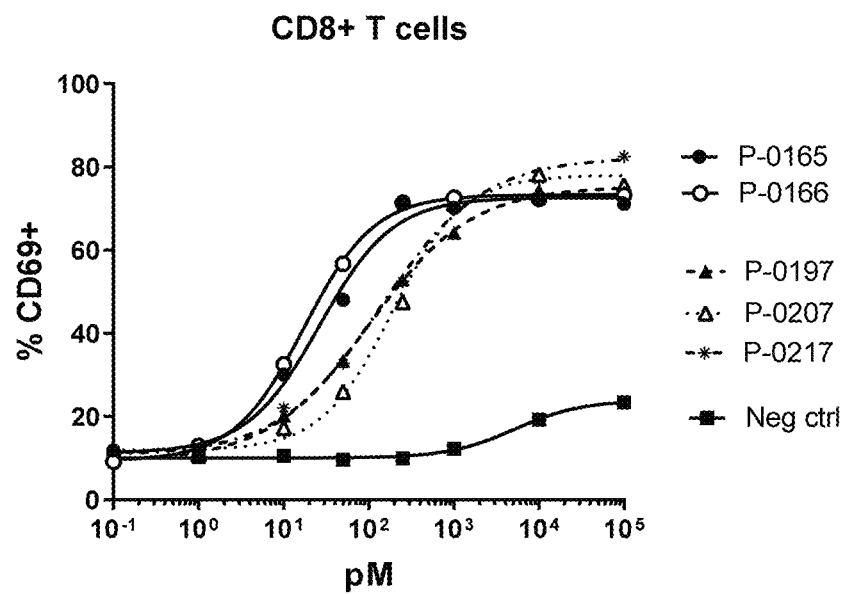

The biological activity was determined by measuring the induction of CD69 expression on human NK and CD8 T cells in an ex vivo human PBMC FACS-based assays as described previously. P-0165 and P-0166 are monomeric IL-15 (non-covalent)/IL-15Rα Fc fusions with a 10 amino acid rigid and flexible linker, respectively. P-0197, P-0207 and P-0217 are monovalent IL-15/IL-15Rα (non-covalent) Fc fusion proteins with a rigid linker, a GS rich flexible linker of 10 and 15 amino acid length, respectively. Results indicated that the rigidity or the length of the peptide linker joining the Fc and IL-15 (P-0165 & P-0166) or Fc and IL-15Rα (P-0197, P-0207 and P-0217) didn't affect the biological activity of the fusion proteins tested (FIGS. 7A & 7B).

EXAMPLE 5

Effect of Valency on the Activity of IL-15/IL-15Rα Fusion Proteins

Fc fusion proteins for therapeutic use are mostly homodimeric because the IgG1 Fc naturally homodimerizes due to the disulfide bonds formed in the hinge region. The dimeric protein has advantages in avidity, stability, quantity, size and function. However, Fc engineering could generate monomeric Fc fusion proteins. The alteration could affect the biological activity, pharmacokinetics, side effects, or reduce the size of dimeric protein for tissue penetration. To evaluate the effect of valency on the biological activity of IL-15/IL-15Rα Fc fusion proteins, both monomeric and homodimeric forms with different IL-15/IL-15Rα Fc fusion configurations were constructed and biological activity tested.

The biological activity was determined by measuring the induction of CD69 expression on human NK and CD8 T cells in an ex vivo human PBMC FACS-based assays as described previously. Results indicated that the homodimeric form of IL-15/IL-15Rα Fc fusion proteins showed approximately 2-fold enhancement in the biological activity compared to the respective monomeric counterpart across all the fusion formats tested (Table 2), suggesting the dimeric valency may offer advantages in functionality.

TABLE 2

Effect of the IL-15/IL-15RαSushi complex valency on the biological activity of IL-15/IL-15Rα fusion proteins

| Protein ID | Description | CD8+ T cell activation (pM) | CD56+ NK activation (pM) |
|---|---|---|---|
| P-0166 | IL-15 (non-covalent)/IL-15Ra Fc monomer, C-terminal | 17.4 | 5.9 |
| P-0218 | Dimeric counterpart of P-0166 | 10 | 3.1 |
| P-0217 | IL-15/IL-15Ra (non-covalent) Fc monomer, C-terminal | 139 | 28.3 |
| P-0234 | Dimeric counterpart of P-0217 | 45.8 | 4.1 |
| P-0197 | IL-15/IL-15Ra (non-covalent) Fc monomer, C-terminal, rigid linker | 498 | X |
| P-0198 | Dimeric counterpart of P-0197 | 293 | X |
| P-0221 | IL-15/IL-15Ra (non-covalent) Fc monomer, N-terminal | 50.3 | 12.5 |
| P-0223 | Dimeric counterpart of P-0221 | 47.2 | 9.1 |

EXAMPLE 6

Effect of N- or C-Terminal Fc Fusion on the Biological Activity of IL-15

Fc fusion protein can be constructed by placing IL-15/IL-15Rα complex to either the N- or C-terminus of Fc connected by a spacing linker. The optimal scaffold is determined by whether the fusion protein is folded and expressed correctly, and whether the biological activity is retained. The IL-15/IL-15Rα Fc fusion proteins were generated by attaching the IL-15/IL-15Rα complex to either the N- or C-terminus of Fc spaced by a linker. The IL-15/IL-15Rα complex was also configured differently in the context of the C- and N-terminal fusions. P-0218 is the C-terminal bivalent IL-15 (non-covalent)/IL-15Rα Fc fusion protein, and the benchmark is the N-terminal counterpart of P-0218 additionally harboring N72D substitution in IL-15. P-0234 is the C-terminal bivalent IL-15/IL-15Rα (non-covalent) Fc fusion protein, and P-0223 is the N-terminal counterpart of P-0234.

The biological activity of the fusion proteins was determined by measuring Ki67 expression in the nucleus of NK and CD8 T cells following IL-15 compound treatment. IL-15 is a potent lymphocyte growth factor that stimulates NK, T and B cell proliferation and differentiation. Ki67 is a nuclear protein induced in all active phases of cell cycle (G1, S, G2 and M), but not in quiescent phase (G0) and therefore is a marker for cell proliferation.

An ex vivo human PBMC assay was established. Briefly, purified human PBMCs were treated with serial dilutions of IL-15 test compounds and incubated at 37° C. for 3 days. Every 2 days, 50% of medium were replenished with fresh medium and test compounds. At Day 3, cells were washed once with FACS buffer (1% FBS/PBS) and first stained with Fc-blocker and surface marker antibodies, including anti-human CD56-FITC, anti-human CD8-APC and anti-human CD4-Percp-cy5.5 (1:50 dilution). After 30-minutes incubation and wash, cell pellets were fully resuspended by 200 μl/well of 1×Foxp3 fixation & permeabilization working solution and incubated for 30-minutes at room temperature in dark. After centrifugation, 200 μl of 1× permeabilization buffer were added to each well for another wash. Cell pellets were resuspended in permeabilization buffer with anti-human Ki67-PE (1:10 dilution). After 30-minutes incubation at room temperature, cells were collected and washed, resuspended in FACS buffer and ready for the flow cytometric analysis. Data are expressed as % of Ki67 positive cells in gated population.

Figure 8A:
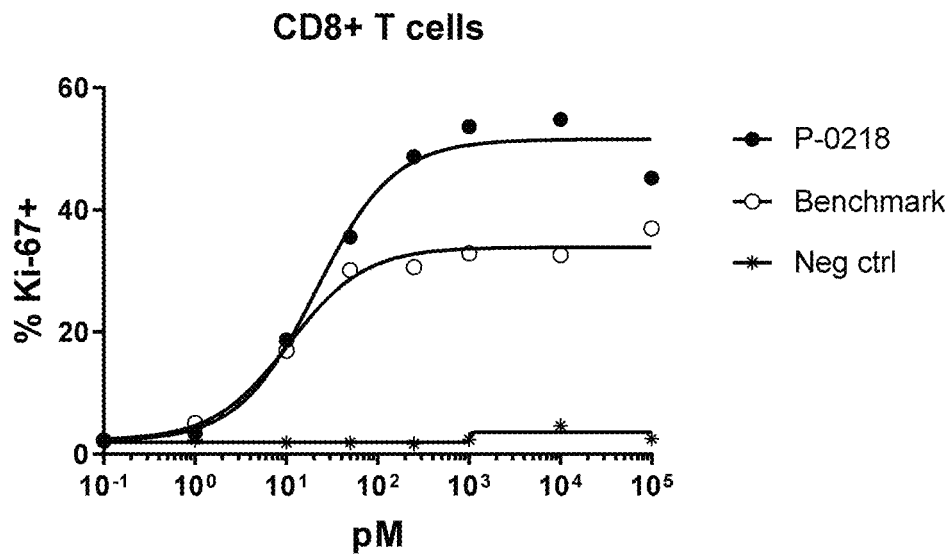
FIG. 8 depicts the effect of N- or C-terminal fusion on the activity of IL-15/IL-15Rα Fc fusion proteins. Percent Ki67 positive CD8 T cells was measured in an ex vivo human PBMC FACS based assay following the treatments. (A) P-0218 (closed circle) and the benchmark (open circle) are the C-terminal and N-terminal bivalent IL-15 (non-covalent)/IL-15Rα Fc fusion proteins, respectively. (B) P-0234 (closed triangular) and P-0223 (open triangular) are the C-terminal and N-terminal bivalent IL-15/IL-15Rα (non-covalent) Fc fusion proteins, respectively.
Figure 8B:
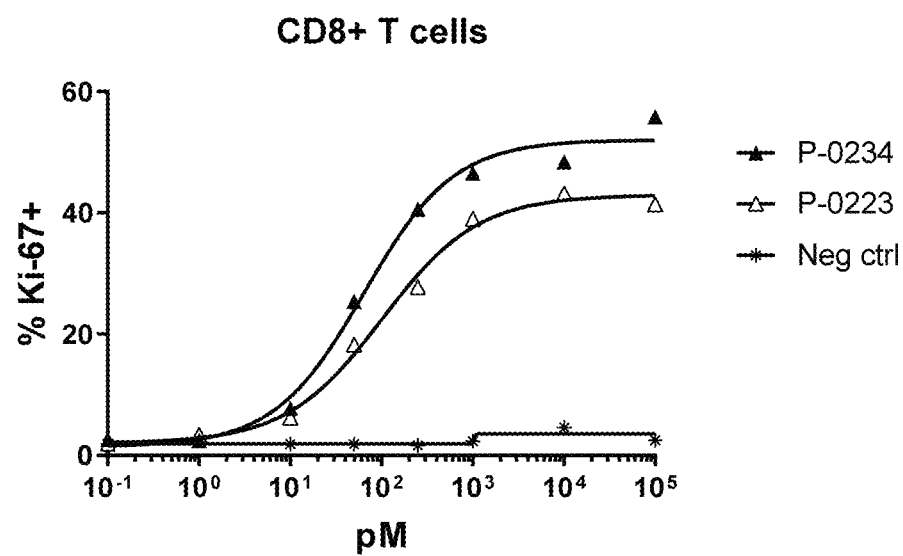

As shown in FIG. 8, the C-terminal Fc fusions (P-0218 and P-0234) consistently demonstrated stronger induction of Ki67 positive CD8 T cells or CD8 T cell proliferation than the N-terminal Fc fusion counterparts (Benchmark and P-0223) (FIGS. 8A and 8B). Data suggest that the C-terminus of Fc is a preferred site for linkage of IL-15/IL-15Rα complex and allows preservation of the biological activity.

EXAMPLE 7

Effect of Receptor-Alpha Domain Selection on the Activity of IL-15/IL-15Rα Fc Fusion Proteins IL-15 binds to the extracellular domain (ECD) of IL-15Rα and the binding is mainly contributed to a conserved protein binding motif called sushi-domain. For construction of a fusion protein, the short and truncated version of IL-15Rα may be desirable to reduce the size and structural complexity. To ensure the binding specificity and affinity, the full or part (the Sushi domain with additional 12 AA) of the ECD domain conferring the binding of IL-15 was constructed into the fusion proteins and the functional activity was determined.

Figure 9A:
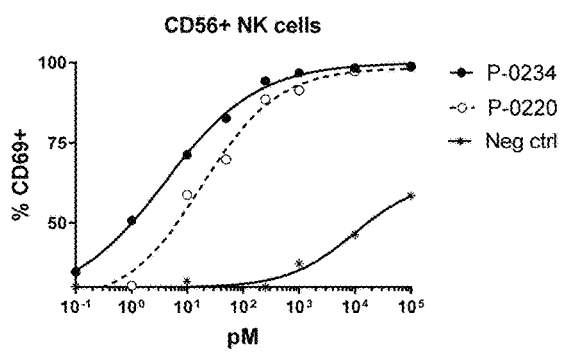
FIG. 9 depicts the effect of IL-15Rα full ECD or Sushi domain on the biological activity of IL-15/IL-15Rα Fc fusion proteins. Induction of CD69 positive NK cells was measured in an ex vivo human PBMC FACS based assay. (A) P-0234 (closed circle) and P-0220 (open circle) are C-terminal bivalent IL-15/IL-15Rα (non-covalent) Fc fusion proteins with IL-15Rα sushi and full ECD, respectively. (B) P-0223 (closed circle) and P-0224 (open circle) are N-terminal bivalent IL-15/IL-15Rα (non-covalent) Fc fusion proteins with IL-15Rα sushi and full ECD, respectively. (C) P-0221 (closed circle) and P-0222 (open circle) are N-terminal monovalent IL-15/IL-15Rα (non-covalent) Fc fusion proteins with IL-15Rα sushi and full ECD, respectively.
Figure 9B:
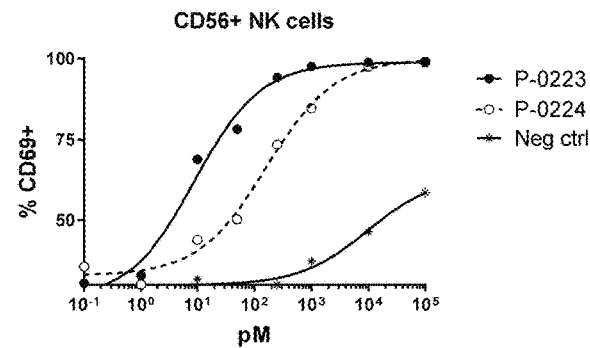
Figure 9C:
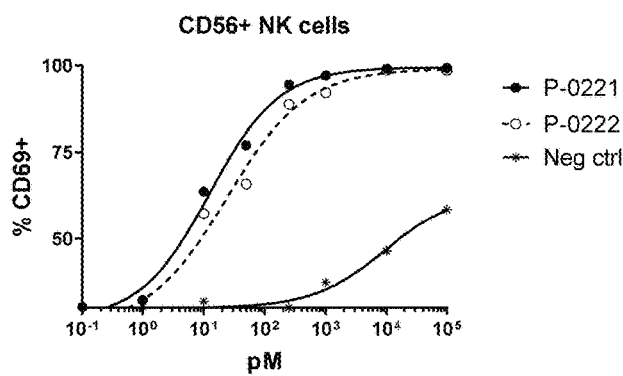

P-0234 and P-0220 are the C-terminal dimeric IL-15/IL-15Rα (non-covalent) fusion proteins, where IL-15Rα is sushi and full ECD, respectively. P-0223 and P-0224 are N-terminal dimeric IL-15/IL-15Rα (non-covalent) Fc fusion proteins, where IL-15Rα is sushi and full ECD, respectively. P-0221 and P-0222 are N-terminal monovalent IL-15/IL-15Rα (non-covalent) Fc fusion proteins, where IL-15Rα is sushi and full ECD, respectively. Results indicated that the fusion proteins non-covalently complexed with the IL-15Rα sushi domain were more potent than those complexed with IL-15Rα full ECD in inducing CD69 positive NK cells, irrespective of the fusion format as N-terminal or C-terminal, dimeric or monomeric (FIG. 9). Data suggest the IL-15Rα sushi domain is more desirable than the full ECD to construct IL-15/IL-15Rα Fc fusion proteins and to confer an optimal conformation for IL-15 to interact with the signaling receptors.

EXAMPLE 8

IL-15 Mutants and the Binding Activity of the Variant Fusion Proteins to IL-15Rβ

In searching for IL-15 agonist, super-agonist or antagonist, deletion, insertion or point mutations were introduced into the human IL-15 peptide sequence at the contact interphase between IL-15 and receptor beta or gamma. The variants were introduced into different formats of the IL-15/IL-15Rα Fc fusion proteins and the binding activity to IL-15Rβ was quantified by Enzyme-linked Immunosorbent Assays (ELISAs) as described previously.

Table 3 shows the IL-15Rβ binding activity of the C-terminal IL-15 variant/IL-15Rα heterodimeric Fc fusion proteins. The IL-15 variants have amino acid deletion, insertion or point mutations introduced in the human IL-15 peptide. The truncation of 3 amino acids from the C-terminus of IL-15 retained the binding activity of the fusion protein to IL-15Rβ as compared to the full-length wide type IL-15 fusion protein, while further truncation of 6 or 9 amino acids from the C-terminus of IL-15 led to gradual reductions in the binding activity of the fusion proteins. GS insertion with various lengths after N95 resulted in reductions of the IL-15Rβ binding activity of the fusion proteins. Single point mutations at the position 108 (Q108S and Q108A) and the combinational mutation (Q108S, D30T, V31Y, H31E) largely retained the Rβ binding potency of the wild type fusion protein.

Table 4 shows the IL-15Rβ binding activity of the monomeric IL-15 variant (non-covalent)/IL-15Rα Fc fusion proteins, where the human IL-15 domain contains single amino acid substitution at positions 58, 62, 63, 67 or 68. P-0185, the Fc fusion protein containing IL-15 (I67V) variant, demonstrated a similar binding activity to IL-15Rβ as the wild type fusion protein. P-0182, a fusion protein containing an IL-15 variant having an amino acid substitution at position 58 from serine to aspartic acid (S58D), demonstrated 4-fold enhancement in the binding potency to IL-15Rβ compared to wild type fusion protein. The substitutions at positions 62, 63 and 68 of the IL-15 peptide resulted in different degrees of reductions in IL-15Rβ binding activity of the fusion proteins.

Table 5 shows the IL-15Rβ binding activity of the dimeric IL-15 variant/IL-15Rα (non-covalent) Fc fusion proteins, where the human IL-15 contains single amino acid substitution at positions 58 or 68 or amino acid insertion after N95. Similarly, as seen in P-0182 (Table 4), P-0313, which contains the same IL-15 variant with S58D, demonstrated 2-fold enhancement in the binding potency to IL-15Rβ as compared to its respective wild fusion protein P-0234. The data strengthened the notion that the S58D substitution in the IL-15 peptide may tune IL-15 into a super-agonist attributed to the enhanced receptor binding activity.

In summary, IL-15 variant Fc fusion proteins were created and identified with differential IL-15Rβ binding activities. Some of the IL-15 variants exhibited reduced potency to bind to IL-15Rβ as compared to their wildtype counterparts (Tables 3-5). Some variants, such as P-0173, P-0179, P-0180, P-0181, P-0185, retained the binding activity to IL-15Rβ similarly as the wild types (Table 3). A Single point mutation with the substitution of serine at position 58 to aspartic acid in the human IL-15 domain offered enhanced binding activity of the fusion proteins (P-0182 & P-0313) to IL-15Rβ (Tables 4 & 5).

TABLE 3

| Protein ID | IL-15/IL-15Rα heterodimeric Fc fusion format | ELISA binding $EC_{50}$ (nM) | Fold change |
|---|---|---|---|
| P-0153 | IL-15 wild type | 0.65 | 1 |
| P-0173 | IL-15d1 (111-114 deletion) | 0.66 | 1 |
| P-0174 | IL-15d2 (108-114 deletion) | 4.54 | 7 |
| P-0175 | IL-15d3 (105-114 deletion) | 23.1 | 36 |
| P-0176 | IL-15i1 (GS insertion after N95) | 10.2 | 16 |
| P-0177 | IL-15i2 (GGSGG insertion after N95) | 38.0 | 59 |
| P-0178 | IL-15i3 (GSSGGSGGS insertion after N95) | 23.1 | 36 |
| P-0179 | IL-15m1 (Q108S) | 1.42 | 2 |
| P-0180 | IL-15m2 (Q108A) | 2.76 | 4 |
| P-0181 | IL-15m3 (Q108S, D30T, V31Y, H31E) | 5.57 vs 3.9 (WT) | 1.4 |

TABLE 4

| Protein ID | Monovalent IL-15 (non-covalent)/ IL-15Rα Fc fusion format | ELISA binding $EC_{50}$ (nM) | Fold change |
|---|---|---|---|
| P-0165 | IL-15 wild type | 1.24 | 1 |
| P-0182 | IL-15m8 (S58D) | 0.31 | 0.25 |
| P-0183 | IL-15(T62D) | 6.29 | 5 |
| P-0184 | IL-15(V63F) | 15.6 | 13 |
| P-0185 | IL-15(I67V) | 1.96 | 1.6 |
| P-0186 | IL-15m9 (I68F) | 106 | 86 |

TABLE 5

| Protein ID | Bivalent IL-15/IL-15Rα (non-covalent) Fc fusion format | ELISA binding $EC_{50}$ (nM) | Fold change |
|---|---|---|---|
| P-0234 | IL-15 wild type | 0.83 | 1 |
| P-0313 | IL-15m8 (S58D) | 0.36 | 0.43 |
| P-0356 | IL-15m9 (I68F) | 1717 | 2068 |
| P-0357 | IL-15m10 (I68K) | 219 | 264 |
| P-0358 | IL-15m11 (I68D) | 2835 | 3415 |
| P-0359 | IL-15m12 (I68H) | 2486 | 2995 |
| P-0361 | IL-15i1 (GS insertion after N95) | 7.66 | 9 |

EXAMPLE 9

Functional Activity of IL-15 Variant/IL-15Rα Fc Fusion Proteins

The Fc fusion proteins of IL-15 variant/IL-15Rα complex were evaluated for their functional activity in stimulating lymphocyte activation. An ex vivo human PBMC assay was established to analyze the number/percent of CD8 T cells expressing CD69, a lymphocyte activation marker, as previously described.

P-0234 is a C-terminal dimeric IL-15/IL-15Rα sushi (non-covalent) Fc fusion protein optimized by a combination of preferred configurations, including covalent IL-15 linkage to Fc, C-terminal fusion, dimeric valency and non-covalent IL-15Rα sushi complexation. P-0313 is the S58D counterpart of P-0234. It shares the same fusion configuration as P-0234 but differs only with S58D substitution in the IL-15 polypeptide. P-0313 demonstrated increased IL-15Rβ binding activity compared to the wild type counterpart P-0234 previously (Table 5). Consistent with the enhanced binding activity to IL-15Rβ, the variant P-0313 harboring the S58D mutation also demonstrated an increased potency in inducing CD69 positive T cells (Table 6), confirming P-0313 exhibits super-agonist activity. Interestingly, two IL-15 variant fusion proteins (P-0179 and P-0181), which bound to IL-15Rβ comparably as the wild type fusion protein (Table 3), showed complete loss of their ability to induce CD69 positive CD8 T cells (Table 6), suggesting these two IL-15 variants may have impaired ability to interact with $\gamma_c$ and this leads to abolished signaling activity and dampened biological functions. These variants, including P-0179 and P-0181, could serve as dominant negative antagonists to block the endogenous IL-15 function.

Additional Fc fusion proteins of IL-15 variant/IL-15RαSushi complex were also tested in CD69 assays, and their biological activities were either retained or reduced as compared to the respective wild type fusion (Table 6 and Table 7).

TABLE 6

| Description | | Fold change in binding $EC_{50}$ | % increase in CD69+ CD8 T cells $EC_{50}$ (nM) | Note |
|---|---|---|---|---|
| IL-15/IL-15Rα heterodimeric Fc fusion format | | | | |
| P-0153 | IL-15 wild type | 1 | 3.1 | |
| P-0173 | IL-15d1 (111-114 deletion) | 1 | 0.1 | Agonist |
| P-0179 | IL-15m1 (Q108S) | 2 | NA* | Antagonist |
| P-0181 | IL-15m3 (Q108S, D30T, V31Y, H31E) | 1.4 | NA | Antagonist |
| Monovalent IL-15 (non-covalent)/IL-15Rα Fc fusion format | | | | |
| P-0165 | IL-15 wild type | 1 | 0.081 | |
| P-0185 | IL-15 (I67V) | 1.6 | 0.161 | Agonist |
| Bivalent IL-15/IL-15Rα (non-covalent) Fc fusion format | | | | |
| P-0234 | IL-15 wild type | 1 | 0.012 | |
| P-0313 | IL-15m8 (S58D) | 0.4 | 0.007 | Super-agonist |

*NA, not applicable because of too low to quantify

TABLE 7

| Description | | % increase in CD69+ CD8 T cells $EC_{50}$ (pM) | % increase in CD69+ NK cells $EC_{50}$ (pM) |
|---|---|---|---|
| IL-15/IL-15Rα heterodimeric Fc fusion format | | | |
| P-0153 | IL-15 wild type | 3.1 | |
| P-0209 | IL-15m4 (Q108S, D30T) | NA | |
| P-0210 | IL-15m5 (Q108S, V31Y) | NA | |
| P-0211 | IL-15m6 (Q108S, H32E) | NA | |
| Monovalent IL-15 (non-covalent)/IL-15Rα Fc fusion format | | | |
| P-0165 | IL-15 wild type | 170 | 39.5 |
| P-0235 | IL-15m7(Q108M) | 2322 | 306.4 |
| Bivalent IL-15/IL-15Rα (non-covalent) Fc fusion format | | | |
| P-0356 | IL-15m9 (I68F) | 1047 | 1223 |
| P-0357 | IL-15m10 (I68K) | NA | NA |
| P-0358 | IL-15m11 (I68D) | 7465 | NA |
| P-0359 | IL-15m12 (I68H) | 983 | 770 |
| P-0360 | IL-15d4 (deletion 109-114) | NA | NA |
| P-0361 | IL-15i1 (GS insertion after N95) | NA | NA |

*NA, not applicable - too low to quantify

EXAMPLE 10

The Signaling Activity of IL-15(S58D)/IL-15Rα Fc Fusion Proteins

The IL-15(S58D) variant demonstrated increased binding activity to IL-15Rβ and enhanced potency in stimulating CD69 positive lymphocytes. The current study examined the signaling activity of IL-15(S58D)/IL-15Rα fusion proteins in stimulating intracellular phosphorylation of the signal transducer and activator of transcription 5 (pSTAT5) in NK and T cells.

STAT5 phosphorylation was determined by intracellular FACS analysis in an ex vivo human PBMC assay following IL-15 compound treatment. Briefly, purified human PBMCs were treated with serial dilutions of IL-15 test compounds and incubated at 37° C. for 15 minutes. At the end of the treatment, cells were washed once with FACS buffer (1% FBS/PBS) and incubated in 150 μl/well of pre-warmed Cytofix fixation buffer at 37° C. for 15 minutes. Fixed cells should be washed again and resuspended in 150 μl/well pre-cooled Perm buffer II at 4° C. for 30 minutes. After blocking Fc receptor by adding human TruStain FcX (1:50 dilution), cells were stained with anti-human CD56-FITC, anti-human pSTAT5-PE, anti-human CD8-APC and anti-human CD4-Percp-cy5.5 (1:50 dilution). After 45-minutes incubation with the antibodies at room temperature, cells were collected and washed, resuspended in FACS buffer and ready for the flow cytometric analysis. Data are expressed as % of pSTAT5 positive cells in gated population.

Figure 10A:
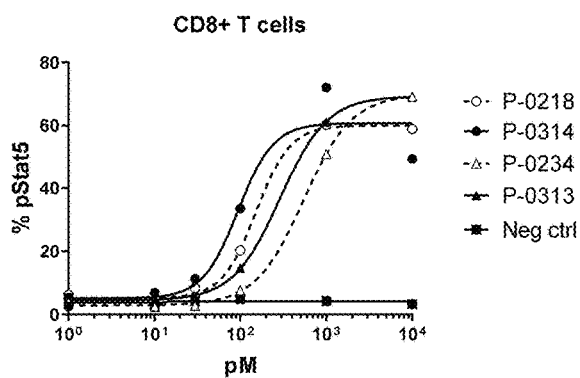
FIG. 10 depicts that the S58D substitution in the IL-15 polypeptide enhanced the ability of IL-15 fusion proteins to induce STAT5 phosphorylation on CD8+ T cells (A), CD4+ T cells (B), and NK cells (C). P-0218 (open circle) and P-0314 (closed circle) are bivalent IL-15 (non-covalent)/IL- 15Rα Fc fusion proteins, comprising IL-15 wild type and S58D variant, respectively. P-0234 (open triangular) and P-0313 (closed triangular) are bivalent IL-15/IL-15Rα (non-covalent) Fc fusion proteins, comprising IL-15 wild type and S58D variant, respectively.
Figure 10B:
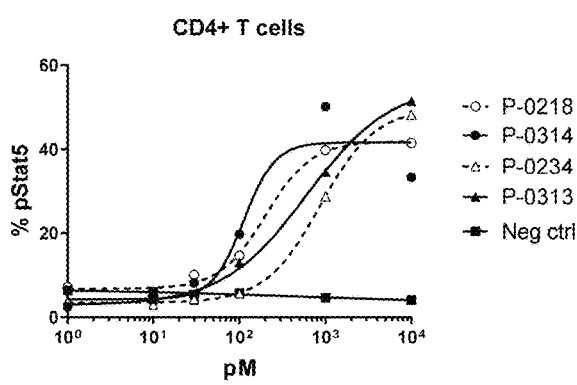
Figure 10C:
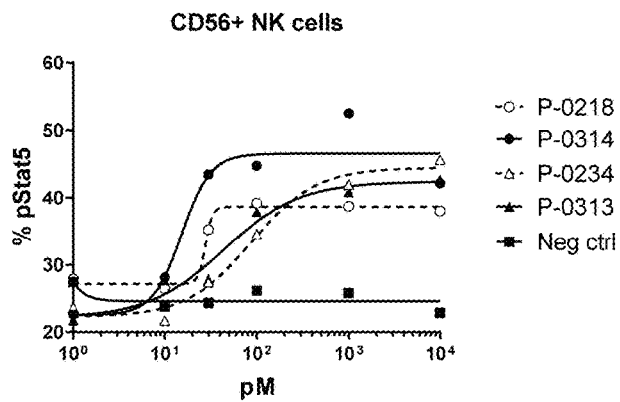

The S58D mutation was introduced into two formats of the Fc fusion proteins: the bivalent IL-15 (non-covalent)/IL-15Rα Fc fusion and the IL-15/IL-15Rα (non-covalent) Fc fusion proteins. P-0218 and P-0314 are the C-terminal dimeric IL-15 (non-covalent)/IL-15Rα Fc fusion proteins containing wild type and S58D variant IL-15, respectively. P-0234 and P-0313 are C-terminal dimeric IL-15/IL-15Rα (non-covalent) Fc fusion proteins containing wild type and S58D variant IL-15, respectively. Regardless of the fusion configurations, the IL-15(S58D) variant fusion proteins (P-0314 and P-0313) demonstrated about 2-fold increase in potency to stimulate STAT5 phosphorylation as compared to their respective wide-type fusion proteins (P-0218 and P-0234) in CD8 (FIG. 10A), CD4 (FIG. 10B) T cells, as well as NK cells (FIG. 10C). Data confirmed the S58D substitution in the IL-15 peptide leads to a super-agonist activity of various IL-15 proteins.

EXAMPLE 11

The Cell Proliferation Activity of IL-15(S58D)/IL-15-Rα Fc Fusion Proteins

Following observed increases in the ability to bind to IL-15Rβ, stimulate STAT5 phosphorylation and induce CD69 expression, the IL-15(S58D) variant Fc fusion proteins were tested for their ability to stimulate cell proliferation in comparison with the wild type fusion proteins by measuring Ki67 expression in NK and CD8 T cells. Human PBMC were treated with increasing doses of IL-15 fusion molecules and Ki67 expression was determined by intracellular FACS analysis gated on CD56+ NK and CD8+ T cell populations as previously described.

Figure 11A:
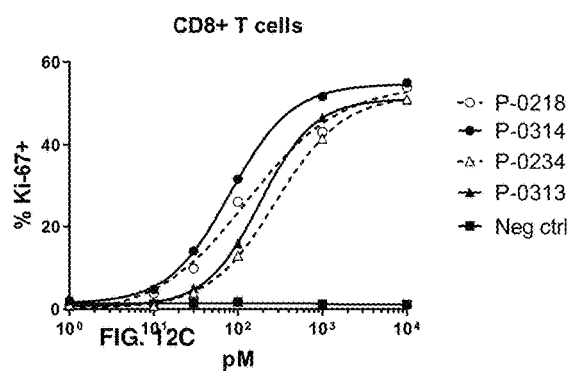
FIG. 11 depicts that the IL-15 (S58D) variant-containing fusion proteins exhibited enhanced ability to induce Ki67 expression on CD8+ T cells (A), CD4+ T cells (B) and NK cells (C). P-0218 (open circle) and P-0314 (closed circle) are bivalent IL-15 (non-covalent)/IL-15Rα Fc fusion proteins, comprising IL-15 wild type and S58D variant, respectively. P-0234 (open triangular) and P-0313 (closed triangular) are bivalent IL-15/IL-15Rα (non-covalent) Fc fusion proteins, comprising IL-15 wild type and S58D variant, respectively.
Figure 11B:
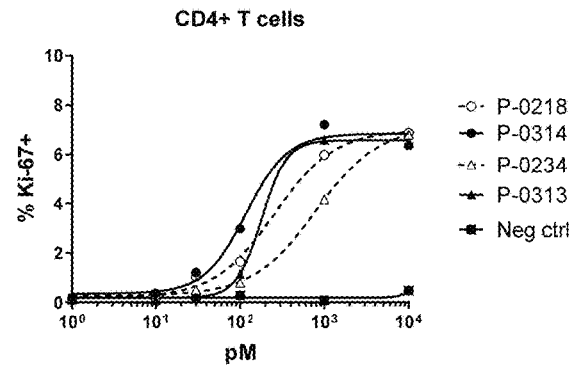
Figure 11C:
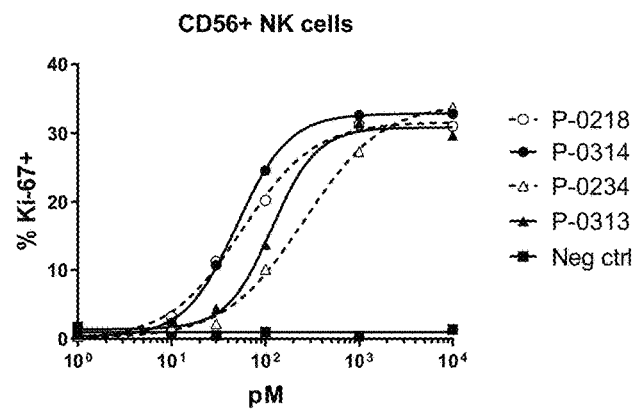

Similar to what were observed for STAT5 phosphorylation as shown in (FIG. 11), the fusion proteins of the IL-15(S58D) variant also demonstrated 2-fold increase in potency to stimulate Ki67 expression as compared to the wild types in CD8+(FIG. 11A) and CD4+(FIG. 11B) T cells, as well as CD56+NK cells (FIG. 11C). These data strengthened that the introduction of S58D mutation in the IL-15 domain provides enhancement in a range of biological activities, including receptor binding, intracellular signaling, activation of cell surface marker and cell proliferation.

EXAMPLE 12

A 4-Day Repeated Dosing Study with P-0234 in Comparison with rhIL-15 and Benchmark in Mice The IL-15/IL-15Rα Fc fusion proteins demonstrated strong abilities to bind to IL-15Rβ, induce intracellular signaling cascade and stimulate proliferation of NK and CD8 T lymphocytes in vitro and ex vivo. Here we examined the serum exposure and the effect of various IL-15 compounds on NK cell proliferation and expansion in mice. The tested proteins include recombinant human native IL-15 (rhIL-15), P-0234 (a C-terminal bivalent IL-15/IL-15Rα (non-covalent) Fc fusion protein), and the benchmark compound (a N-terminal bivalent IL-15(non-covalent)/IL-15Rα Fc fusion protein comprising N72D mutation in IL-15).

7-week old female Balb/c mice were received from Charles River Laboratory and acclimated in house for at least 7 days before the study. Mice were given daily i.p. injections with equivalent molar doses of IL-15 compounds for 4 days. The treatments include vehicle, 0.03 mg/kg rhIL-15 (40 pmol/kg), 0.1 and 0.5 mg/kg benchmark (40 and 200 pmol/kg), and 0.1 and 0.5 mg/kg P-0234 (40 and 200 pmol/kg). Each group had 5 mice. Body weight was recorded daily prior to and during the treatment. Mice were sacrificed one hour after the last injection and terminal blood was collected via cardiac puncture.

Heparinized whole blood and spleen were collected for NK cell phenotyping and Ki67 intracellular staining. After lysing red blood cells and blocking Fc-receptors with purified anti-mouse CD16/CD32 (1:50 dilution), mononuclear blood and splenic cells in a single-cell suspension were stained with NK cell surface markers, including anti-mouse CD3-FITC and anti-mouse CD49b-APC (1:50 dilution), for 30 minutes at room temperature in dark. For intracellular Ki67 staining, cell pellets were fully resuspended by 200 ul/well of 1×Foxp3 fixation/permeabilization working solution and incubated for 30-minutes at room temperature in dark. Cells were the washed with 200 µl of 1× permeabilization buffer and Fc-receptors were blocked with purified anti-mouse CD16/CD32 (1:50 dilution). Cells were then stained with Ki67-PE in addition to anti-mouse CD3-FITC and anti-mouse CD49b-APC for NK cell population (1:50 dilution). After 30-minutes incubation, cells were collected and washed, resuspended in FACS buffer and ready for the flow cytometric analysis. Statistical analysis was conducted by one-way ANOVA with Tukey's post-hoc multiple comparison in GraphPad prism software.

Figure 12:
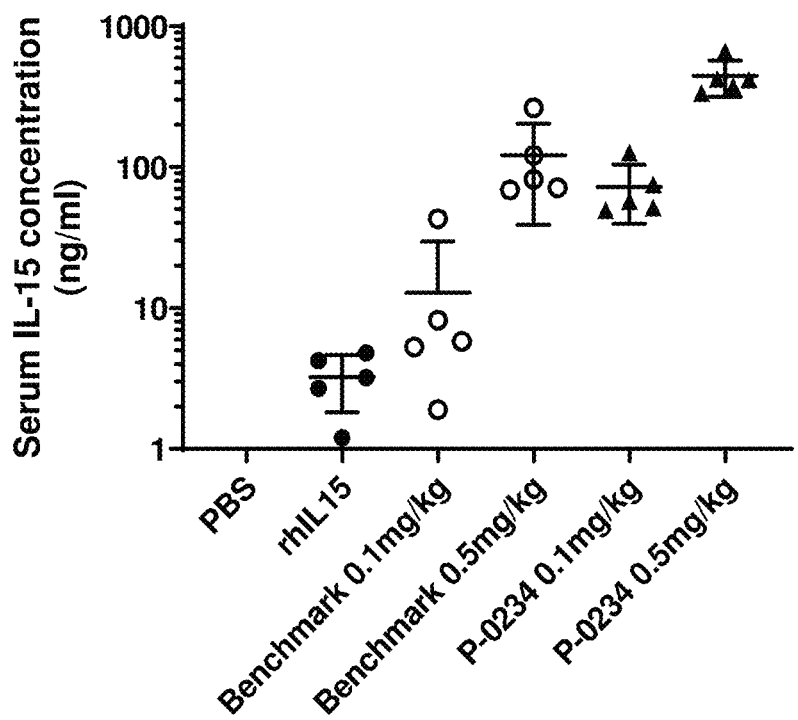
FIG. 12 depicts serum concentrations of IL-15 in mice treated with rhIL-15, the benchmark and P-0234 in a 4-day repeated dosing study. Female B Balb/C mice were i.p. injected daily with vehicle, rhIL-15 (0.03 mg/kg), the benchmark (0.1 and 0.5 mg/kg), or P-0234 (0.1 and 0.5 mg/kg). Terminal blood was collected one hour after the last injection on day 4 and serum IL-15 levels were measured using an ELISA assay.

FIG. 12 shows serum concentrations of IL-15 at 1 hour post the last injection of the IL-15 compounds. The IL-15 was measured by a commercial ELISA kit detecting IL-15 following the manufacturer's instruction (R&D systems; Cat #DY247). After 4 daily dosing of the compounds, the cumulative serum concentrations of IL-15 were the highest in mice treated with P-0234, intermediate in mice treated with the benchmark and the lowest in mice treated with rhIL-15 given at the equivalent molar doses (FIG. 12). Comparing the benchmark and P-0234 administered at 0.1 and 0.5 mg/kg, P-0234 consistently demonstrated 6-fold and 4-fold higher serum concentrations than the benchmark. The mean serum concentrations of IL-15 were 3.2±0.6 (ng/ml) for rhIL-15 (0.03 mg/kg dosing), 13±8 and 121±36 (ng/ml) for the benchmark compound (0.1 and 0.5 mg/kg dosing, respectively), and 72±14 and 443±57 (ng/ml) for P-0234 (0.1 and 0.5 mg/kg dosing, respectively). The superior serum exposure suggests that P-0234 may exhibit a longer in vivo half-life and serum retention compared with the benchmark and rhIL-15.

Figure 13A:
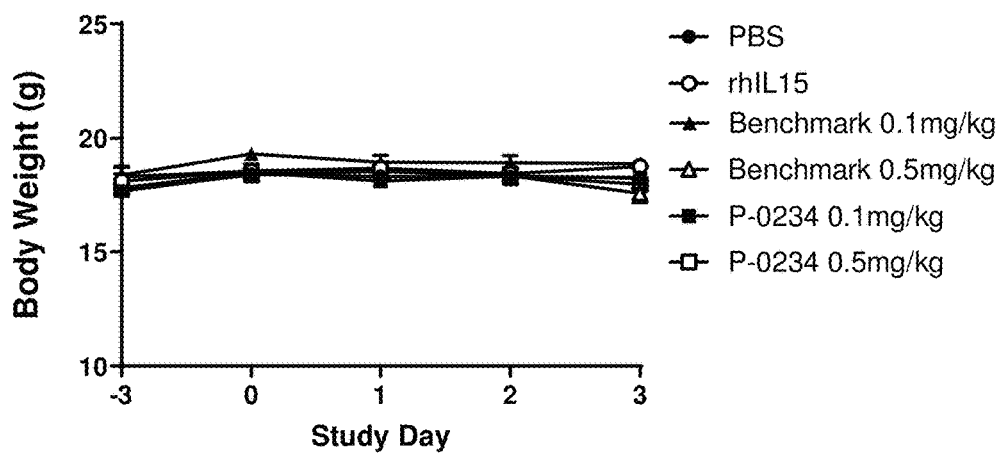
FIG. 13 depicts body weight (A) and % change in body weight from Day 0 (B) in Balb/C mice treated with rhIL-15, the benchmark and P-0234 during a 4-day repeated dosing study. Data are expressed as mean±SEM. Statistical analysis was performed by one-way anova followed by Tukey's post hoc test. *** $p<0.001$ compared to Day 0; #$p<0.05$ compared to PBS group.
Figure 13B:
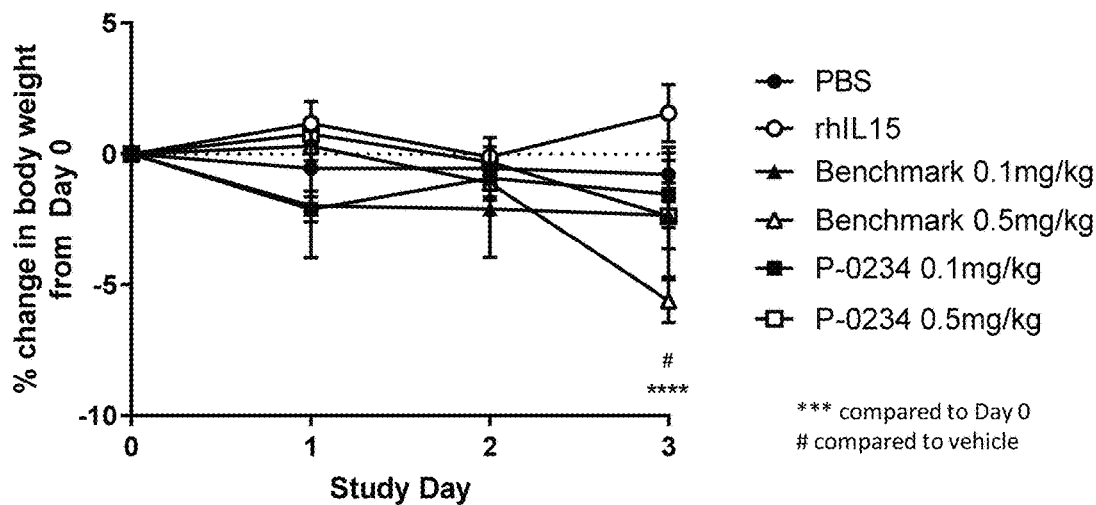

Although there is no difference in gross body weights among the treatment groups, mice treated with the higher dose of the benchmark lost nearly 6% body weight within 4 days of treatment (FIG. 13A & 13B). The effect was statistically significant compared to baseline values at day 0 and to the vehicle group, suggesting a potential dose-limiting toxicity observed with the benchmark compound but not P-0234.

Figure 14A:
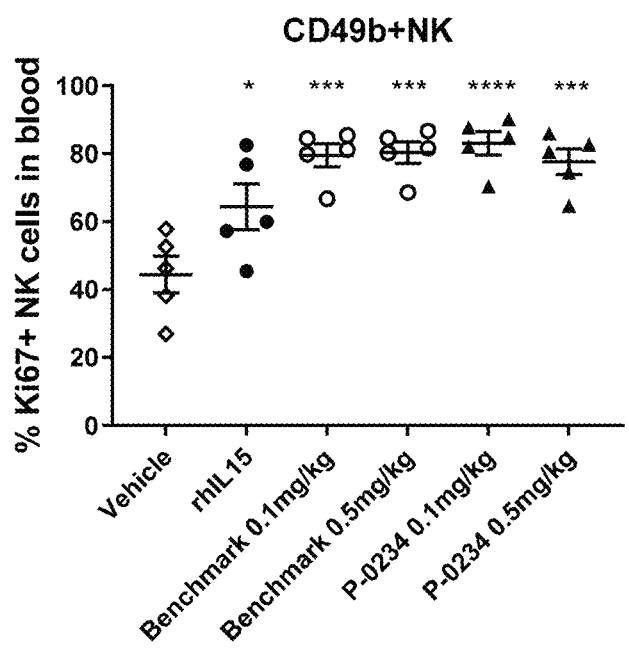
FIG. 14 depicts the effect of IL-15 compounds on the NK cell proliferation and expansion in the peripheral blood of Balb/C mice in a 4-day repeated dosing study. After 4 daily doses, blood was collected for Ki67 measurement and NK cell phenotyping by FACS. (A) Percentage of the proliferation marker Ki67 positive NK cells; (B) Percentage of NK cells in CD3 negative lymphocyte population. Data were expressed as mean±SEM. Statistical analysis was performed by one-way anova followed by Tukey's post hoc test. **** $p<0.0001$ compared to vehicle group, #$p<0.001$ & ##$p<0.01$ compared to equivalent dose of the Benchmark.
Figure 14B:
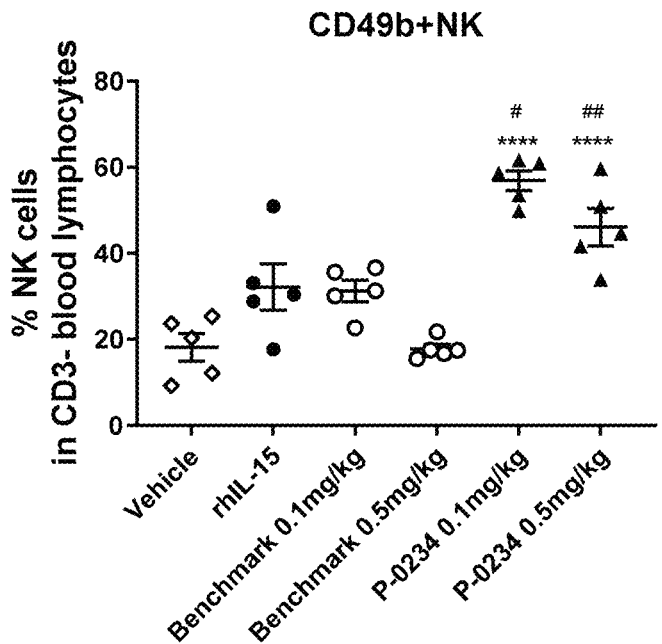

All tested IL-15 compounds increased the percentage of Ki67 positive NK cells in peripheral blood (FIG. 14A), suggesting an enhanced NK cell proliferation. However, a significant increase in the percentage of NK cell numbers in CD3 negative peripheral blood lymphocytes was only observed in mice treated with P-0234 at both tested dose levels (FIG. 14B). Although an increase in the percentage of NK cells was also observed in mice treated with rhIL-15 and the lower dose of benchmark, the effect didn't reach statistical significance (FIG. 14B). Interestingly, a decline in the NK cell numbers in peripheral blood was observed in mice treated with the higher dose benchmark (FIG. 14B). Such a reversed pharmacodynamic dose-response is suggestive of toxicity in agreement with the observed loss of body weight in this group.

Figure 15A:
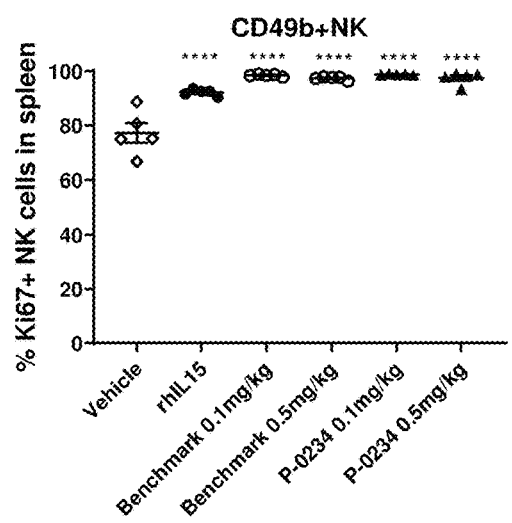
FIG. 15 depicts the effect of IL-15 compounds on the proliferation, expansion and activation of splenic NK cells of Balb/C mice in a 4-day repeated dosing study. (A) Percentage of the proliferation marker Ki67 positive splenic NK cells; (B) Total NK cells in the spleen; (C) Percentage of CD69 positive splenic NK cells. Data were expressed as mean±SEM. Statistical analysis was performed by one-way anova followed by Tukey's post hoc test. ** $p<0.0001$,  $p<0.01$, * $p<0.05$ compared to vehicle group.
Figure 15B:
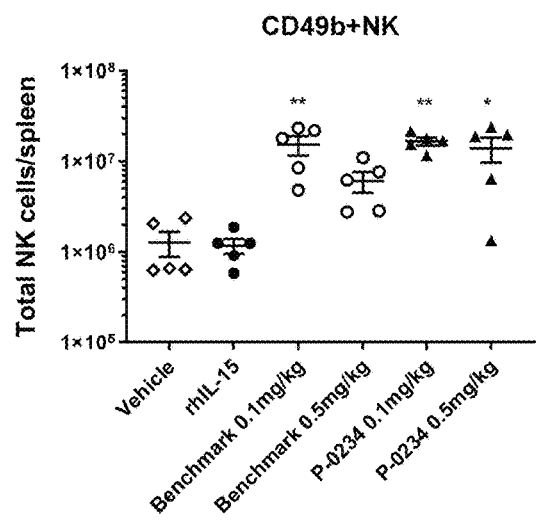
Figure 15C:
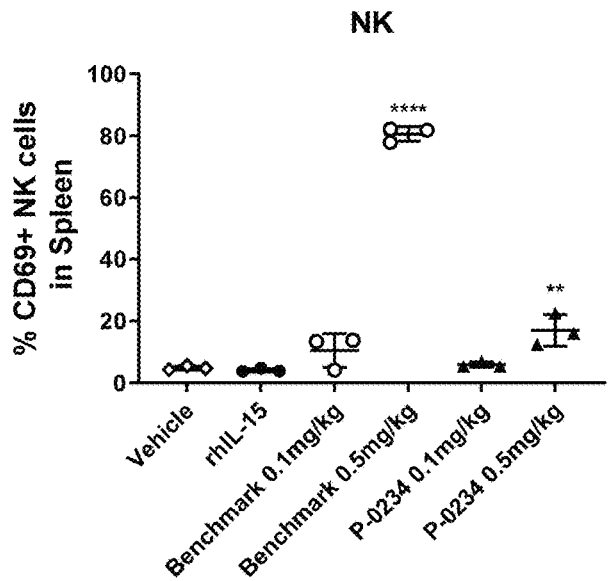

The effect of IL-15 compounds on lymphocyte proliferation and expansion was also examined in the lymphoid organ the spleen. Similar to what was observed in peripheral blood, all IL-15 compounds increased the splenic Ki67 positive NK cells compared to vehicle (FIG. 15A). Only the low dose benchmark and P-0234 significantly increased the total number of NK cells in the spleen (FIG. 15B). Likewise, a reversed dose-response on splenic NK cell expansion was observed for the benchmark (FIG. 15B), and this was associated with high and persistent CD69 expression on splenic NK cells measured 4 days post termination (FIG. 15C). Data suggest that the benchmark compound may overstimulate NK cells and lead to cell exhaustion. With the IL-15 non-covalently bound to the IL-15Rα Fc fusion protein, the IL-15 may dissociate from the fusion complex and lead to lymphocyte overstimulation, cell exhaustion, toxicity and weight loss.

EXAMPLE 13

Pharmacokinetic and Pharmacodynamic Effects of IL-15/IL-15Rα Fc Fusion Proteins in Mice Following a Single Injection A dose-response study with P-0313, a C-terminal divalent IL-15(S58D)/IL-15Rα (noncovalent) Fc fusion protein, was conducted in Balb/C mice following a single injection. The effect on peripheral blood lymphocyte proliferation and expansion was monitored over time. In addition, the pharmacokinetics and pharmacodynamics (PK/PD) of P-0313 were compared with those of the Benchmark, a N-terminal divalent IL-15(noncovalent)/IL-15Rα Fc fusion protein comprising N72D mutation in IL-15, following a single injection.

7-week old female balb/c mice were received from Charles River Laboratory and acclimated in house for at least 7 days before the study. Vehicle, benchmark (0.3 mg/kg) or P-0313 (0.01, 0.03, 0.1 and 0.3 mg/kg) was administered i.p. to mice at time 0. Blood samples were withdrawn at −24 hr. (pre-dose), and 1, 4, 24, 72, 120, and 192 hours post injection. Body weight was recorded daily prior to and during the treatment. Each group included 5 mice.

Heparin-treated whole blood was used for immune phenotyping and the volume was recorded. After red blood cell lysis using BD pharm lysis buffer, total viable mononuclear blood cells were counted by trypan blue dead cells exclusion and proceeded to Ki67 intracellular staining. Cell pellets were fully resuspended by 200 ul/well of 1×Foxp3 fixation/permeabilization working solution and incubated for 30 minutes at room temperature in the dark. After centrifugation, 200 ul of 1× permeabilization buffer was added to each well for another wash. After blocking Fc-receptors with purified anti-mouse CD16/CD32 (1:50 dilution), cells were stained with anti-mouse CD3-FITC, Ki67-PE, anti-mouse CD49b-APC and anti-mouse CD8-Percpcy5.5 (1:50 dilution). After a 30-minute incubation, cells were collected and washed, resuspended in FACS buffer and analyzed by flow cytometry. Statistical analysis was conducted by one-way ANOVA with Tukey's multiple comparison test in GraphPad prism software.

Serum concentrations of the compounds were measured using two different ELISA assays. An in-house ELISA assay was developed to measure the IL-15 and Fc complex, and the commercial ELISA assay measures IL-15 alone with both capture and detection antibodies reactive to human IL-15. For the in-house ELISA assay, maxisorp plates were coated with anti-IL-15 antibody (R&D systems MAB647) overnight at 4° C. Plates were blocked with SuperBlock. Standard and samples at various dilutions were applied to the plates and incubated one hour at room temperature. Active compound was detected with anti-human IgG Fc-HRP and signal was detected using Ultra TMB Substrate Solution. Values were calculated using GraphPad Prism interpolation from non-linear regression curve fit.

Figure 16A:
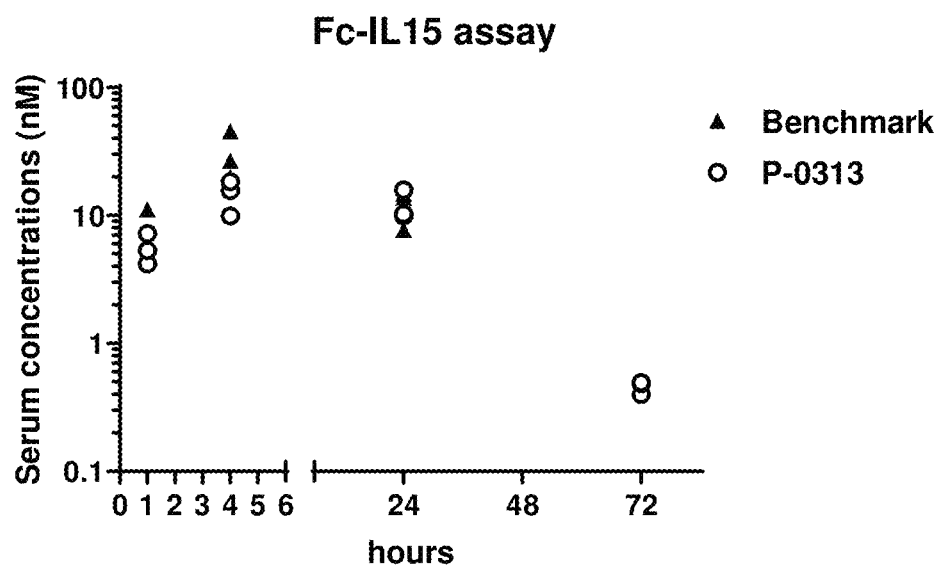
FIG. 16 depicts serum concentrations of P-0313 and the benchmark following a single intraperitoneal injection in Balb/C mice. Blood was collected from mice treated with 0.3 mg/kg P-0313 or the Benchmark at −24 (pre-dose) and 1, 4, 24, 72, 144 and 192 hours after dose. (A) an in-house ELISA assay detecting human Fc-IL-15 complex; (B) A commercial ELISA assay detecting human IL-15.
Figure 16B:
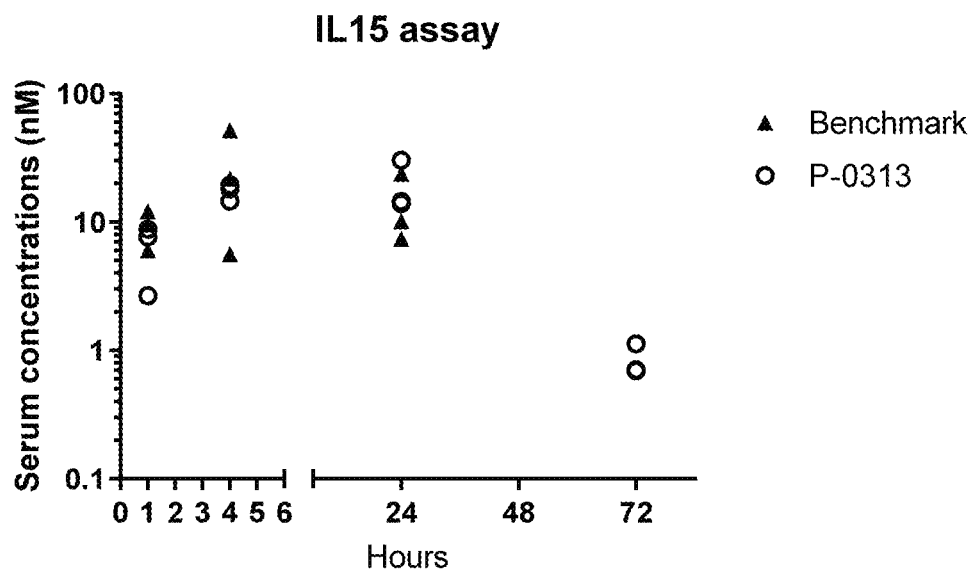

Both compounds were detectable in the serum at the first 24 hours with comparable serum concentrations. The peak concentrations were observed 4 hours after i.p. administration. At 72 hours, only P-0313 remained measurable and the benchmark became undetectable in all three mice (FIGS. 16A-16B). Similar results were obtained using two different ELISA assays, confirming P-0313 has a superior pharmacokinetic profile than the benchmark. The result corroborated with the previous observation shown in Example 12 that P-0234, an IL-15/IL-15Rα (noncovalent) Fc fusion protein, also demonstrated higher serum exposure than the benchmark. These data strongly support that the IL-15/IL-15Rα (noncovalent) Fc fusion configuration is superior to that of IL-15 (noncovalent)/IL-15Rα Fc fusion protein in prolongation of IL-15 in vivo half-life.

Figure 17:
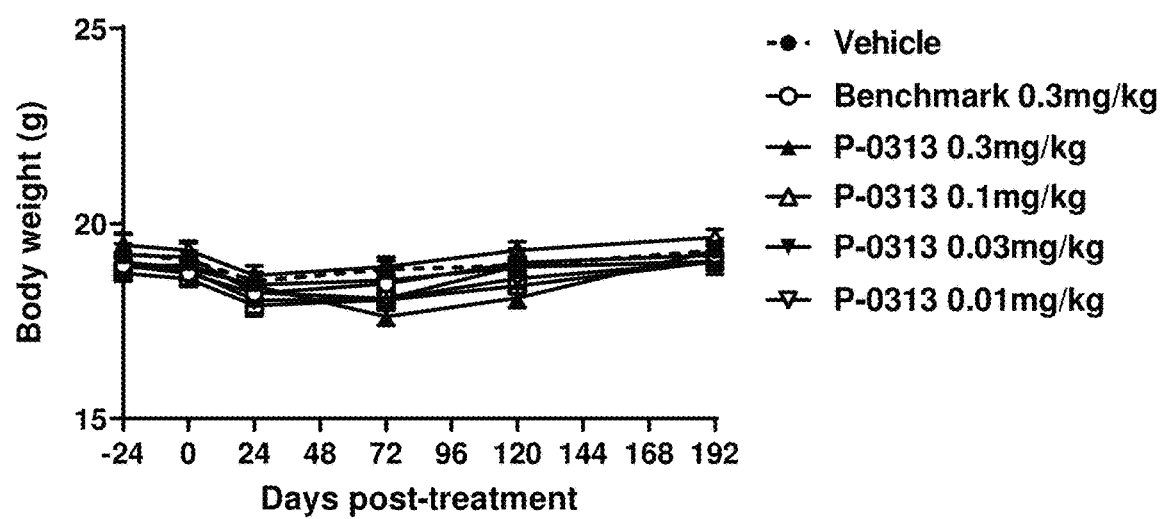
FIG. 17 depicts body weight in Balb/C mice following a single injection of P-0313 and the benchmark in a period of 8 days.

No significant changes in body weight were observed in any treatment groups (FIG. 17).

Figure 18A:
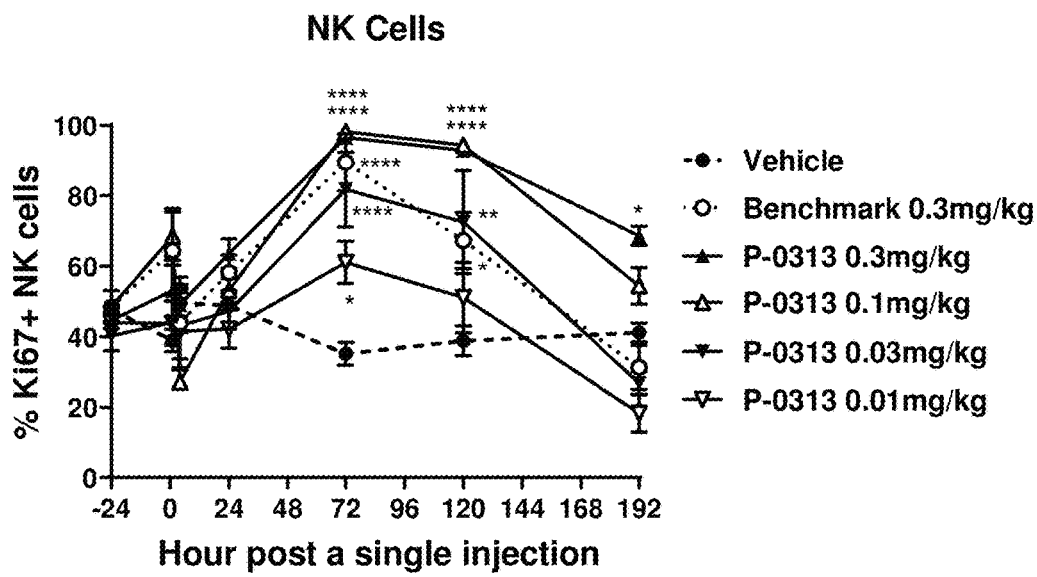
FIG. 18 depicts dose- and time-dependent effects of IL-15/IL-15Rα Fc fusion proteins on Ki67 expression on NK (A) and CD8+ T cells (B) following a single injection in Balb/C mice. Blood was collected at −24 (pre-dose), and 1, 4, 24, 72, 144 and 192 hours for lymphocyte phenotyping and Ki67 measurement by FACS analysis. Data are expressed as mean±SEM. Statistical analysis was performed by two-way anova followed by Tukey's post hoc test. ** $p<0.0001$,  $p<0.01$, * $p<0.05$ compared to PBS group at respective time point.
Figure 18B:
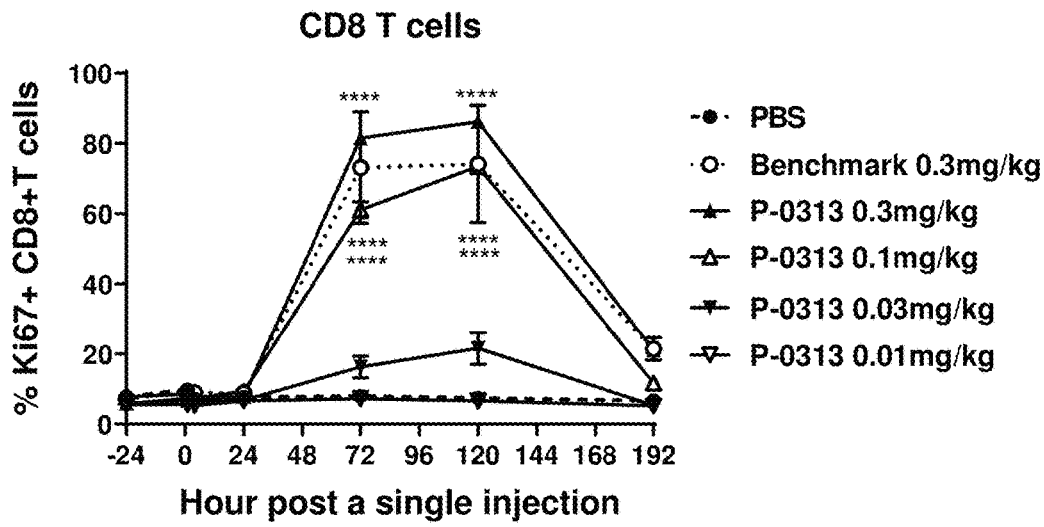

Dose-dependent increases in Ki67 expression were observed in NK and CD8 T cells in mice treated with P-0313 (FIG. 18A & 18B). Effects peaked at 72 hours and persisted to 120 hours for the benchmark and further extended to 192 hours for P-0313 (FIG. 18A), suggesting P-0313 is longer-acting than the benchmark. In addition, P-0313 revealed a similar Ki67 induction at a dose 3-10 folds lower than that of the benchmark, suggesting P-0313 is more efficacious than the benchmark (FIG. 18A & 18B). A significant response on NK cells was observed at 10-fold lower dose than on CD8 T cells, suggesting NK cell is more sensitive than CD8 T cells to P-0313 treatment.

Figure 19A:
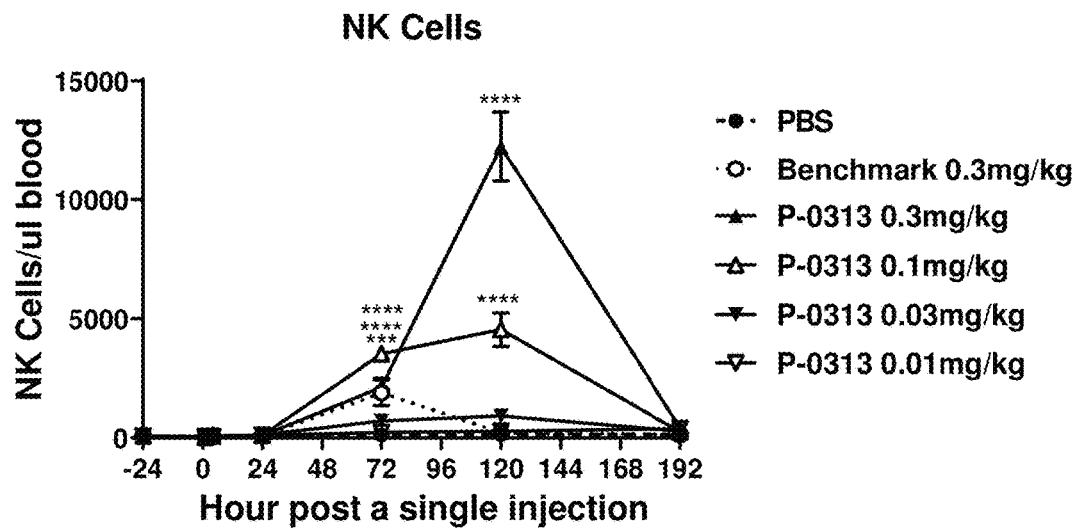
FIG. 19 depicts dose- and time-dependent effects of IL-15/IL-15Rα Fc fusion proteins on the expansion of NK (A) and CD8+ T cells (B) in peripheral blood following a single injection in Balb/C mice. Blood was collected at −24 (pre-dose), and 1, 4, 24, 72, 144 and 192 hours for lymphocyte phenotyping by FACS analysis. Data are expressed as mean±SEM. Statistical analysis was performed by two-way anova followed by Tukey's post hoc test. ** $p<0.0001$, * $p<0.001$, * $p<0.05$ compared to PBS group at respective time point.
Figure 19B:
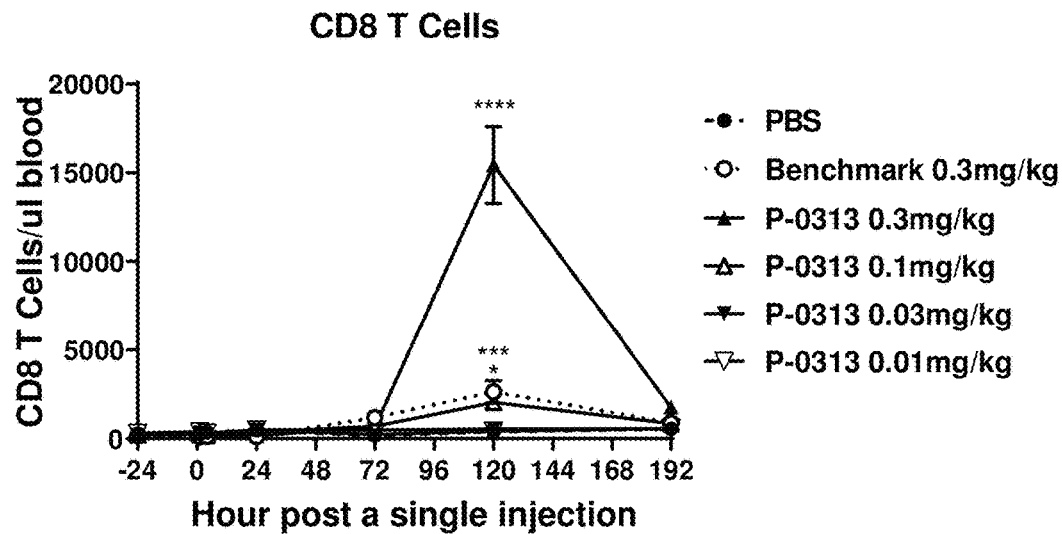

Consistent with the observed increase in cell proliferation marker Ki67, a dose-dependent expansion of NK and CD8+ T cells in blood was observed in P-0313 treated groups (FIG. 19A & 19B). The cell expansion was observed at 72 hours and peaked at 120 hours. P-0313 increased NK cells by 4-, 15-, 50- and 163-fold from the baselines at 0.01, 0.03, 0.1 and 0.3 mg/kg doses, respectively (FIG. 19B), and also increased CD8 T cells by 10- and 50-fold from the baselines at 0.1 and 0.3 mg/kg doses (FIG. 19B). In contrast, the benchmark at 0.3 mg/kg dose only expanded peripheral NK cells by 28 folds and CD8 T cells by 12 folds (FIG. 19A & 19B).

In summary, P-0313 demonstrated a superior pharmacokinetic and pharmacodynamic on NK and CD8 T cell proliferation and expansion to the benchmark compound.

EXAMPLE 14

Effect of IL-15/IL-15Rα Fc Fusion Proteins on Inhibition of Lung Metastasis of Mouse Colon Cancer To investigate anti-metastatic efficacy and immunological responses of IL-15/IL-15Rα-Fc fusion proteins in tumor model, $1 \times 10^5$ mouse colon carcinoma cells, CT26-WT (ATCC CRL-2638), were intravenously injected into female balb/C mice (10-12 weeks-old). On the next day, 0.03 or 0.1 mg/kg of P-0313 or 0.3 mg/kg of the Benchmark compound were given every five days by i.v. injection (Day 1, 6, 11 post-cell transplantation). Vehicle (PBS) was included as a negative control and every group contained 8 mice. On day 15, blood samples were collected for lymphocyte phenotyping and liver enzyme measurements. On day 16, all mice were sacrificed for tissue harvesting. Lungs were inflated by 15% india ink and de-stained in Fekete's solution (10% formaldehyde, 5% glacial acetic acid and 60% ethanol). Lung tumor nodules were counted for the entire lung under light microscope, and anti-metastatic effect were represented by different numbers of tumor nodules between treatment groups and vehicle control.

To study immunological response, mouse peripheral blood was collected on day 15 in heparin-treated tubes and the volume of blood used for the assay per mouse was recorded. After red blood cells were lysed by BD pharm lysis buffer, total viable mononuclear blood cells were counted by trypan blue dead cell exclusion and used for intracellular staining as described previously for immune cell phenotyping, and Ki67 proliferation analyses. After cell fixation, permeabilization and antibody staining, cells were collected and washed, resuspended in FACS buffer and analyzed by flow cytometry.

Figure 20A:
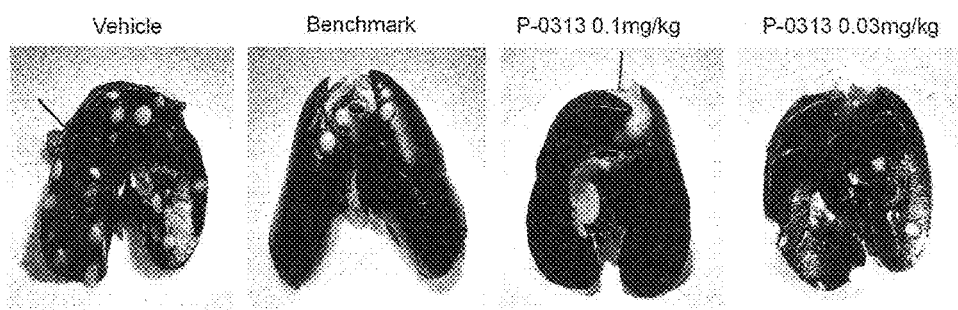
FIG. 20 depicts inhibition of lung metastasis by P-0313 and the benchmark in a mouse CT26 pulmonary metastasis model. Vehicle, the Benchmark (0.3 mg/kg) or P-0313 (0.03 and 0.1 mg/kg) were given 3×Q5D doses initiated one day after the injection of CT26 cells. Mice were sacrificed on day 16 for microscopic counting of the lung metastatic nodules. (A) Representative lung photographs illustrating metastatic nodules from each treatment group. (B) Lung nodule counts obtained under light microscope. Data are expressed as mean±SEM. Statistical analysis was performed by one-way anova followed by Tukey's post hoc test. **** $p<0.0001$, * $p<0.05$ compared to PBS group.
Figure 20B:
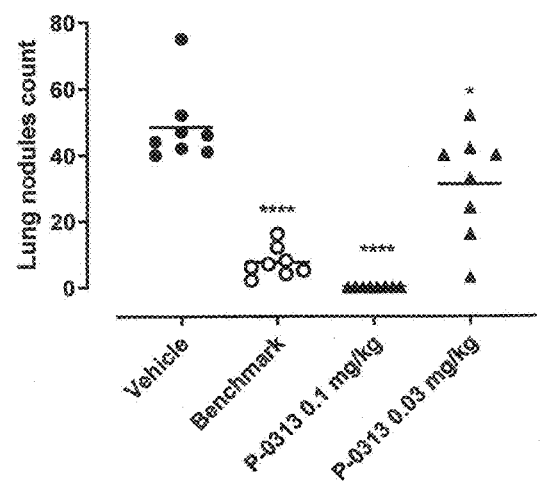

FIG. 20A shows representative photographs of lung from each group to illustrate lung nodules. Lung metastatic lesions were microscopically counted and quantified (FIG. 20B). As shown in FIG. 20, the Benchmark molecule given at 0.3 mg/kg inhibited lung metastasis with 84% reduction in lung nodule counts, confirming that activating IL-15 pathway is effective to prevent the formation and growth of lung metastases. Strikingly, administration of IL-15/IL-15Rα-Fc complex P-0313 at a 3-fold lower dose (0.1 mg/kg) resulted in complete inhibition of the development of lung metastasis with zero nodule observed in all 8 mice treated (FIG. 20A & 20B). The superiority of P-0313 to the Benchmark in suppressing the formation and growth of lung metastases is consistent with the enhanced pharmacokinetic and pharmacodynamic effects demonstrated previously (Example 12 & 13). With its IL-15 moiety covalently linked to the Fc domain, P-0313 demonstrated a marked improvement of IL-15 serum half-life over the Benchmark, which contains an IL-15 that is non-covalently linked to Fc chain via IL-15RαSushi domain (Example 13). P-0313 at 0.03 mg/kg dosing also reduced lung metastasis with an inhibitory effect of −35% (FIGS. 20A & 20B). This observation further emphasized P-0313 is efficacious at much lower doses than the Benchmark and underscores the importance of biodistribution and bioavailability of the IL-15/IL-15Rα-Fc complex on its anti-cancer effect in vivo.

Figure 21A:
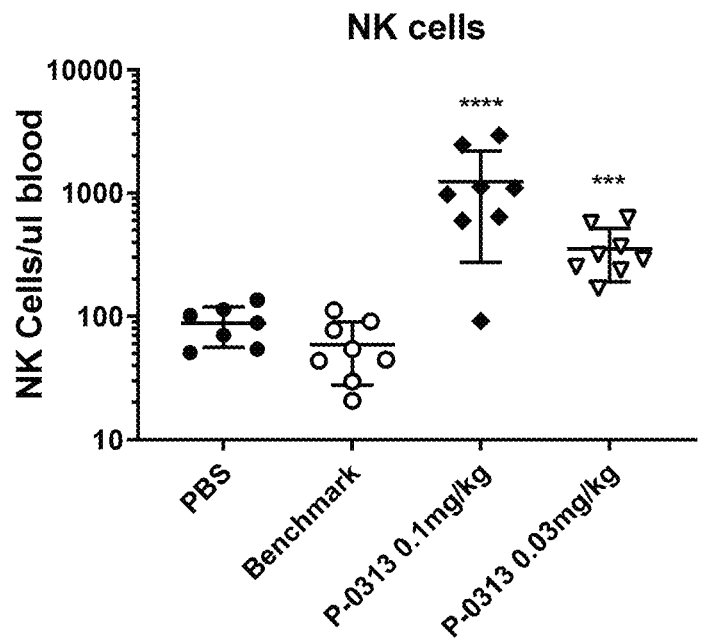
FIG. 21 depicts the immuno-pharmacodynamic profiling in CT26 pulmonary metastasis model following treatment with P-0313 or the Benchmark. Increases in the number of circulating A) NK cells, and B) CD8+ T cells per µl whole blood in CT26 metastasis mice were determined by flow cytometry 3 days after three Q5D i.p. injections of P-0313, Benchmark, or PBS. Data are expressed as mean±SEM. Statistical analysis was performed by one-way anova followed by Tukey's post hoc test. ** $p<0.0001$, * $p<0.001$, ** $p<0.01$ compared to PBS group.
Figure 21B:
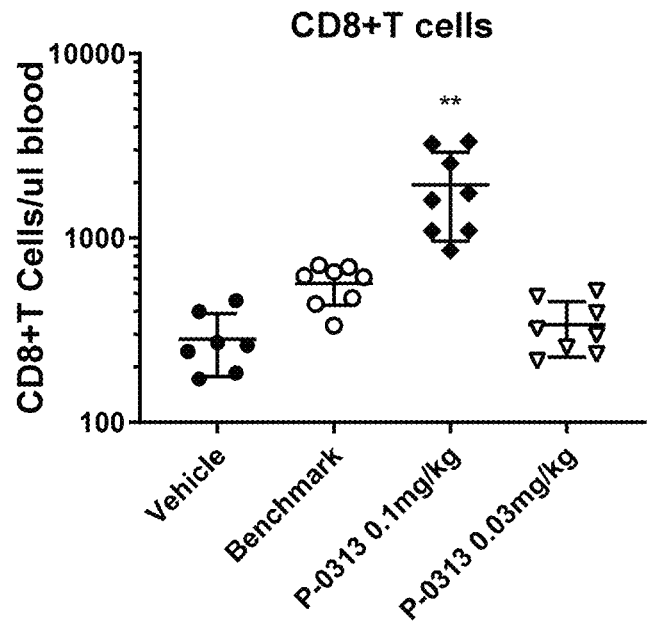
Figure 22:
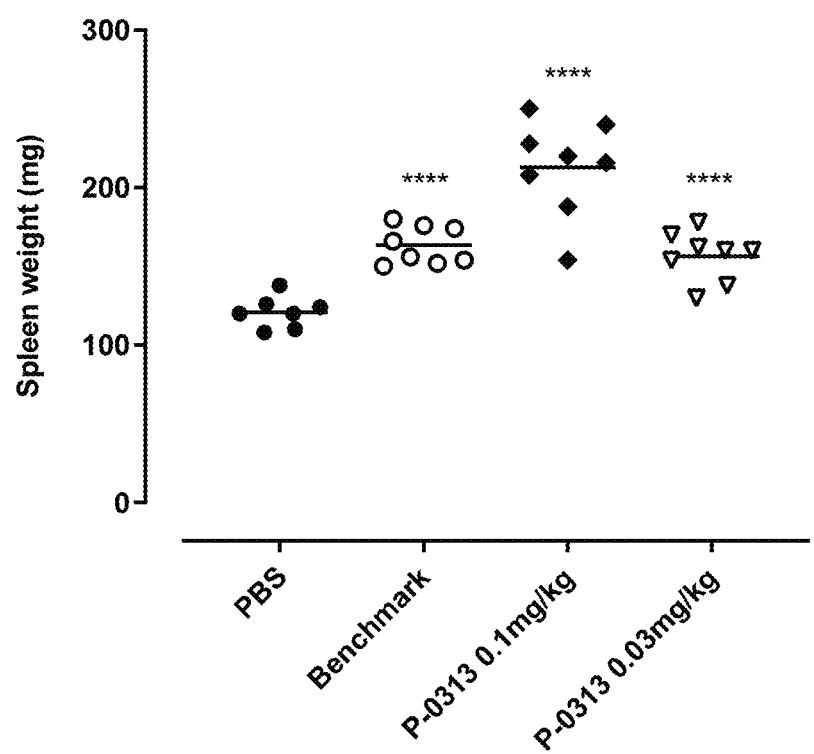
FIG. 22 depicts spleen weights in mice treated with P-0313 or the Benchmark in CT26 pulmonary metastasis model. Spleen were collected 3 days after three Q5D i.p. injections of IL-15/IL-15Rα Fc fusion proteins. Data are expressed as mean±SEM. Statistical analysis was performed by one-way anova followed by Tukey's post hoc test. **** $p<0.0001$ compared to PBS group.

After three repeated Q5D dosing, the expansion of both NK and CD8+ T cells in peripheral blood remained significantly elevated in P-0313 treated mice (FIGS. 21A & 21B), which correlated with the significant increases in spleen weights of this treating groups (FIG. 22). In contrast, for the group treated with 0.3 mg/kg Benchmark, only very modest expansion of CD8+ T cells was observed; no increase in the circulating NK cell numbers observed versus the control group (FIGS. 21A & 21B). However, the spleen weights were significantly increased in the Benchmark treated group (FIG. 22). Data suggest after repeated dosing, the expanded lymphocytes may migrate to the lymphatic tissues for storage or cell exhaustion may also occur. As all the three treating groups showed anti-tumor effect, the data suggested that either CD8+ T cells or NK cells can be the effector subset involved in the antitumoral effects. However, complete eradication of lung metastasis seen in the group treated with 0.1 mg/kg of P-0313 suggested that an action engaging both NK cells and CD8+ T cells induced the strongest inhibition of tumor growth.

Figure 23A:
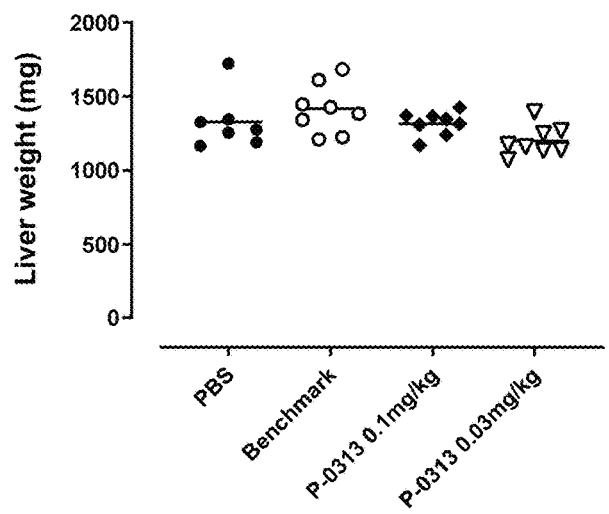
FIG. 23 depicts hepatotoxicity assessment in CT26 pulmonary metastasis mice treated with P-0313 or the Benchmark. Liver were collected three days after three Q5D treatments. A) Liver weight; B) serum ALT level; and C) serum AST level. ALT and AST levels in serum were determined using commercial ELISA kit. Data are expressed as mean±SEM.
Figure 23B:
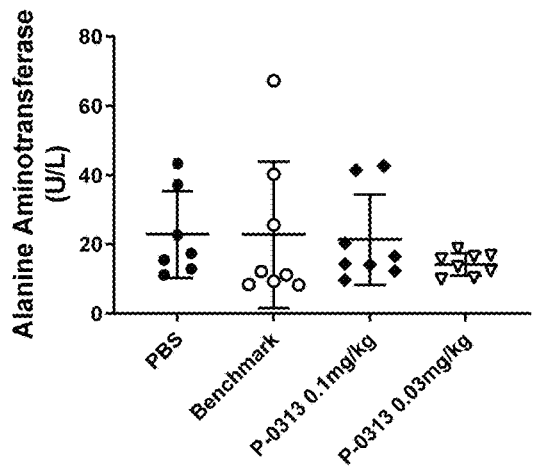
Figure 23C:
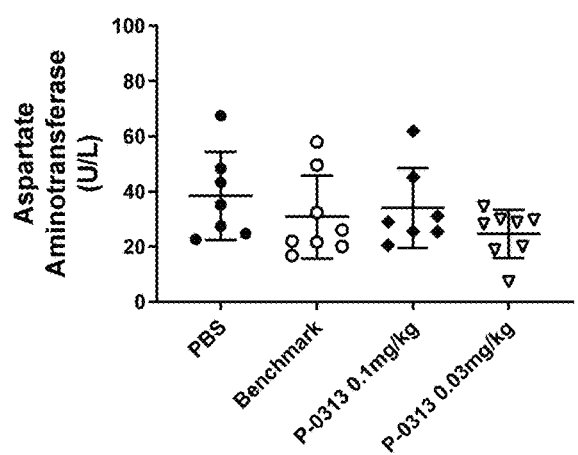

Liver weight and serum concentrations of alanine aminotransferase (ALT) & aspartate aminotransferase (AST) were measured to assess hepatotoxicity associated with the treatment. As depicted in FIGS. 23A-23C, there was no increase in either liver weights, ALT or AST levels for any treatment groups in comparison to the vehicle group. The data suggested that the strong antitumor effect of IL-15/IL-15Rα Fc fusion proteins was not associated with hepatotoxicity.

EXAMPLE 15

Effect of an IL-15/IL-15Rα Fc Fusion Protein on Established CT26 Solid Tumor Growth in Mice To further investigate anti-tumor efficacy and immunological responses of IL-15/IL-15Rα Fc fusion protein in established tumor model, female Balb/C Mice (10-12 weeks old) were injected with 1×10⁵ CT26 cells subcutaneously in the right flank. On day 11, when the average tumor volume was ~70 mm³, mice were randomized into three groups (n=10/group) and received intraperitoneal injection of vehicle (PBS), or P-0313 (0.1 mg/kg or 0.05 mg/kg) on the same day of randomization. One additional intraperitoneal injections of the respective testing agents were performed on day 16 (a total of 2 doses). Tumors were measured three times weekly using calipers, and the tumor volume was calculated as: volume=0.5×(width)²×(length). To study immunological response, non-terminal peripheral blood was collected in heparin-treated tubes on day 19. On day 21, all mice were sacrificed for tissue harvesting.

Figure 24A:
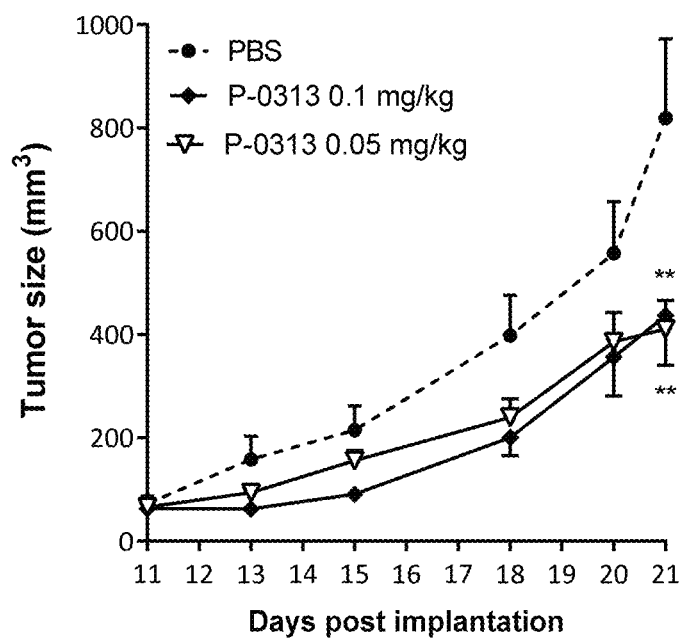
FIG. 24 depicts the antitumor efficacy of P-0313 in subcutaneously established CT26 murine colorectal tumor model. $1 \times 10^5$ CT26 cells were subcutaneously injected on day 0. Vehicle (PBS) or P-0313 (0.1 or 0.05 mg/kg) were giving Q5D for two injections initiated when the average tumor volume was ~70 mm³ (day 11). (A) Growth curve of CT26 s. c. tumors. (B) Change of body weight from baseline. Data are expressed as mean±SEM. Statistical analysis was performed by two-way anova followed by Tukey's post hoc test. ** $p<0.0001$ compared to PBS group.
Figure 25A:
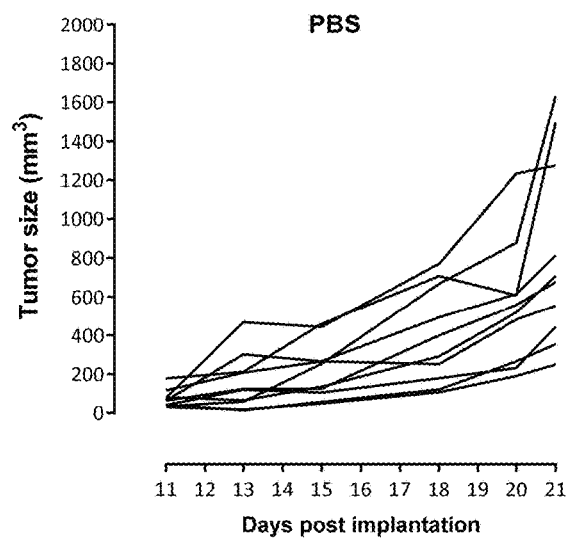
FIG. 25 depicts subcutaneous CT26 tumor growth curve in individual mouse receiving (A) vehicle PBS, (B) 0.05 mg/kg P-0313, or (C) 0.01 mg/kg P-0313. n=10/group.
Figure 25B:
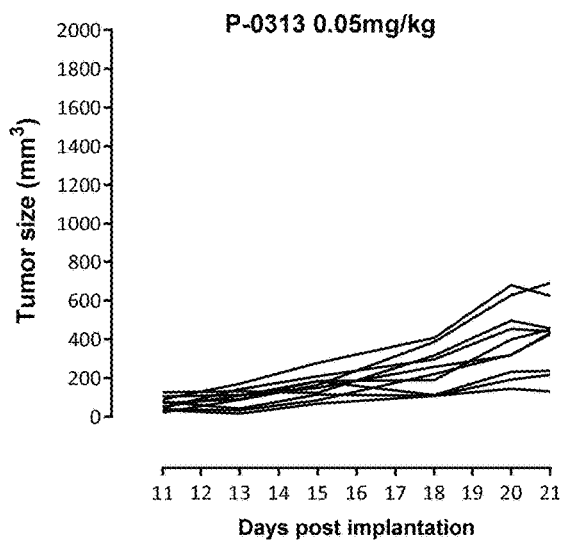
Figure 25C:
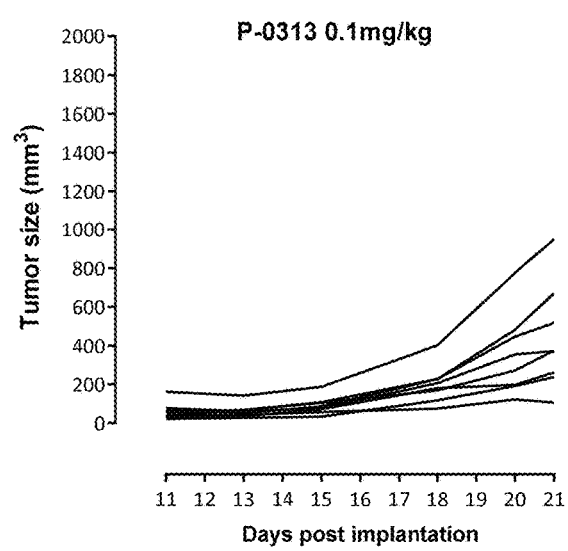

As shown in FIG. 24A, the PBS-treated mice rapidly developed large subcutaneous tumors. Treatment of mice with P-0313 at either 0.1 mg/kg or 0.05 mg/kg were approximately equipotent in delaying tumor growth (FIG. 24A). The tumor growth curve for each individual mouse was plotted for all three treatment groups (FIGS. 25A-25C). It is apparent that mice responded well to the treatment of P-0313 and showed delayed and synchronized inhibition in tumor growth particularly at the initial phase for two tested dose groups (FIGS. 25A-25C). On day 21 post-tumor inoculation, the mean tumor volume in the PBS-treated mice was 820 mm³ versus 410 mm³ in mice treated with P-0313 at both doses (FIG. 25A ** P<0.01; 1-way ANOVA with Tukey's post-test). It is worth noting that P-0313 at the higher dose (0.1 mg/kg) showed a greater decrease of tumor load than the lower-dosing group initially, but the difference tapered off as the treatment proceeded.

Figure 24B:
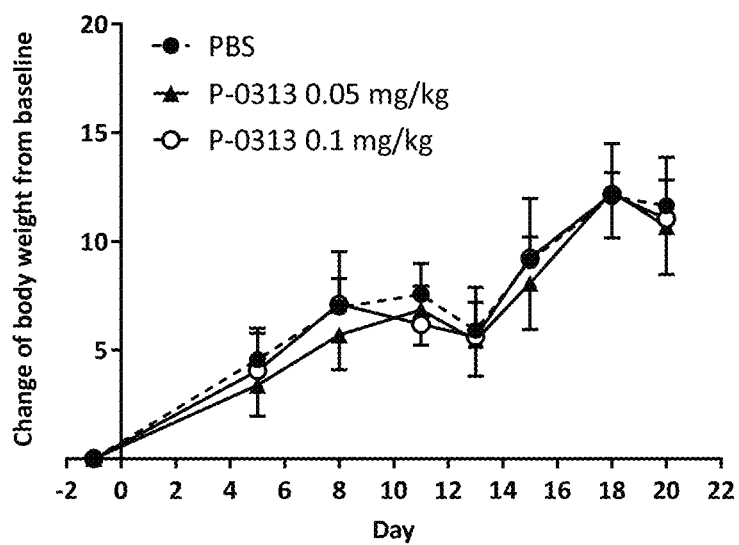

P-0313-treated mice demonstrated similar body weight gain as the PBS-treated mice over the course of 21 days study (FIG. 24B), suggesting P-0313 is well tolerated and not associated with significant toxicity at the two tested doses.

Figure 26A:
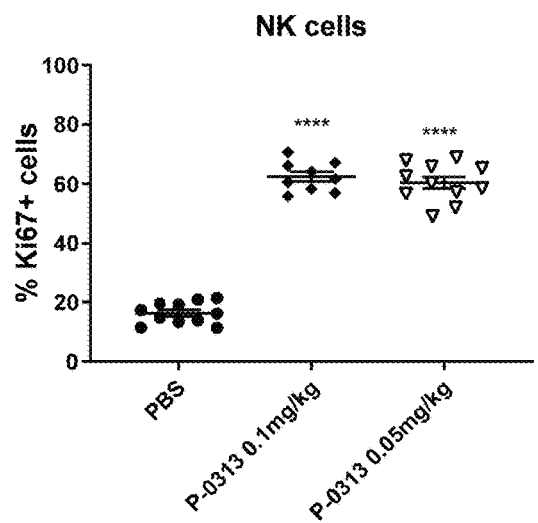
FIG. 26 depicts the NK and CD8 T cell proliferation and expansion in mice treated with P-0313 in CT26 murine colorectal carcinoma tumor model. Following two Q5D treatments initiated 11 days after tumor implantation, increases in Ki67 expression (A-B) and the number of circulating cells (per μl whole blood) (C-D) for NK cells and CD8+ T cells were determined on day 19 by flow cytometry. Data are expressed as mean±SEM; Statistical analysis was performed by one-way anova followed by Tukey's post hoc test. **** p<0.0001, * P<0.05, compared to PBS group.
Figure 26B:
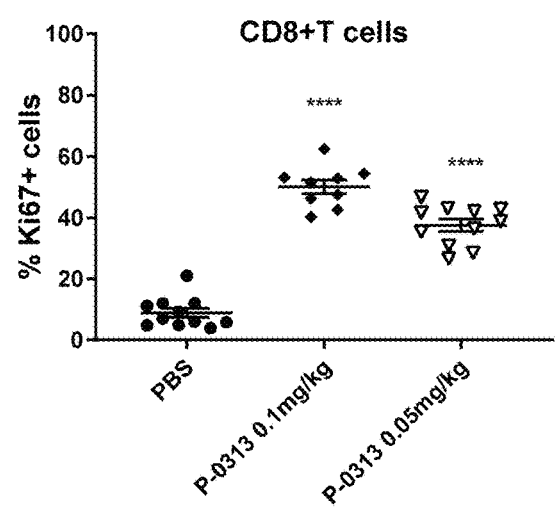
Figure 26C:
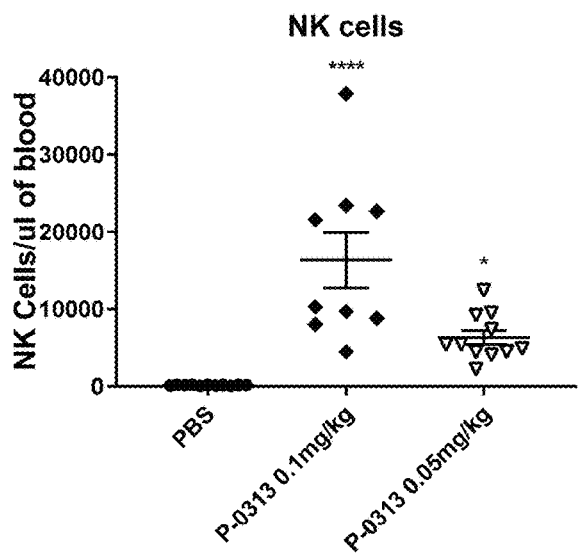
Figure 26D:
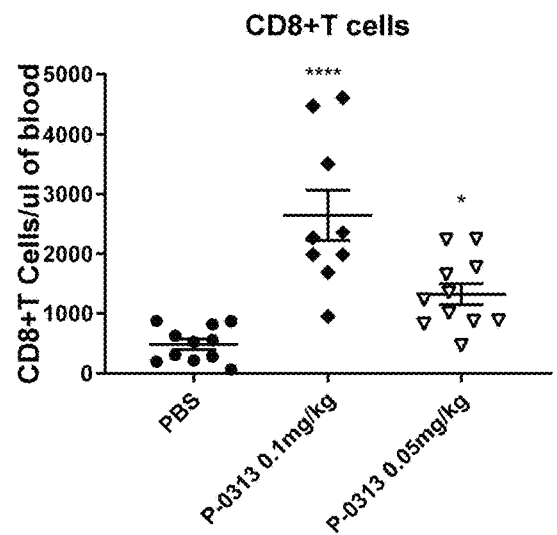

Next, we examined the effect of P-0313 on CD8 T cell and NK cell populations in the peripheral blood and spleen. Administration of P-0313 to tumor-bearing mice induced strong NK cell and CD8 T cell proliferation (FIGS. 26A & 26B) and dose-dependent expansion of NK and CD8 T cells (FIGS. 26C and 26D), a similar degree of immune cell responses as observed in non-tumor-bearing mice (Example 13). Among these two lymphocyte populations, the higher fold change was observed in NK cells (~100 fold for 0.1 mg/kg dosing group, and ~38 fold for 0.05 mg/kg dosing group). CD8+ T cells expanded by ~5.4 fold at 0.1 mg/kg dose, and ~2.7 fold for the 0.05 mg/kg dosing group.

Figure 27A:
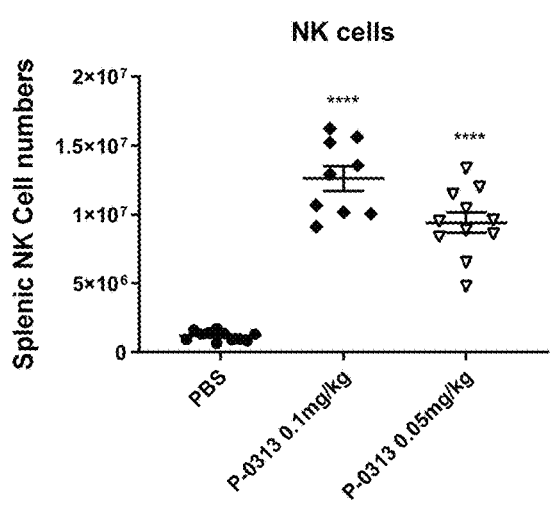
FIG. 27 depicts the immuno-phenotyping of splenic NK and CD8 T cells in the CT26 colorectal tumor-bearing mice treated with P-0313. Following two Q5D treatments initiated 11 days after tumor implantation, increases in the number of splenic NK cells (A) and CD8+ T cells (B) one day 21 were determined by flow cytometry. Data are expressed as mean±SEM; Statistical analysis was performed by one-way anova followed by Tukey's post hoc test. **** p<0.0001 compared to PBS group.
Figure 27B:
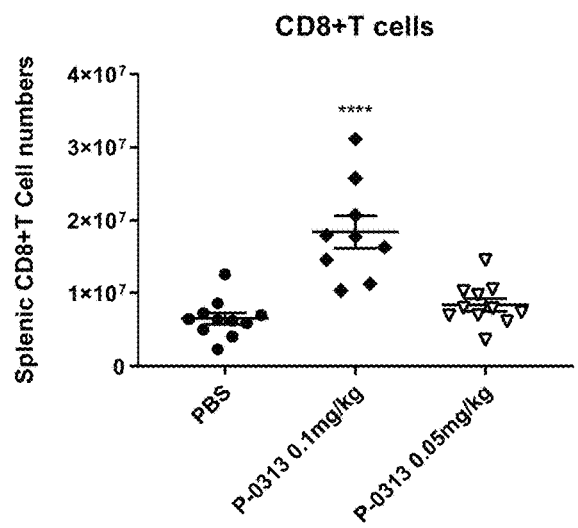

P-0313 also enhanced the expansion of both NK and CD8+ T cells in the spleens as those in peripheral blood (FIGS. 27A and 27B), but the magnitude/fold changes in the spleens were less profound. The higher fold change was observed in NK cells (~10 fold for 0.1 mg/kg dosing group, and ~8 fold for 0.05 mg/kg dosing group). CD8+ T cells expanded by ~2.7 fold at 0.1 mg/kg dose, and only marginally expanded for the 0.05 mg/kg dosing group.

Taken together, these data demonstrated that P-0313 treatment was capable of significantly delaying and inhibiting solid tumor growth and this anti-tumor effect was correlated with the proliferation and expansion of cytotoxic NK and CD8 T cells in tumor-bearing mice, which are consistent with the overall immunomodulatory property of IL-15. Since P-0313 bears an Fc region devoid of effector functions, the anti-tumor activity of P-0313 in vivo is not due to direct killing of tumor cells, but rather due to the robust activation of cytotoxic CD8+ T cells and NK cells for potent immune responses against tumor cells.

EXAMPLE 16

Figure 28A:
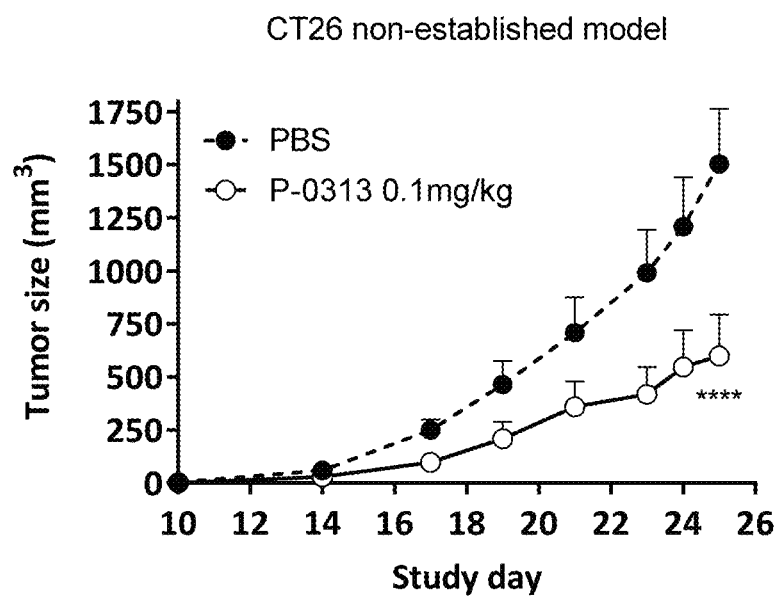
FIG. 28 depicts the antitumor efficacy of P-0313 in non-established CT26 colorectal tumor model. Three days after subcutaneous implantation of $1 \times 10^5$ CT26 cells, mice were given vehicle (PBS) or P-0313 (0.1 mg/kg) Q5D for five injections. (A) Growth curve of CT26 s. c. tumors after tumor cell implantation on day 0. (B) Tumor weight on Day 25. Data are expressed as mean±SEM. Statistical analysis was performed by one-way anova followed by Tukey's post hoc test. *** p<0.001, * p<0.05, compared to PBS group
Figure 28B:
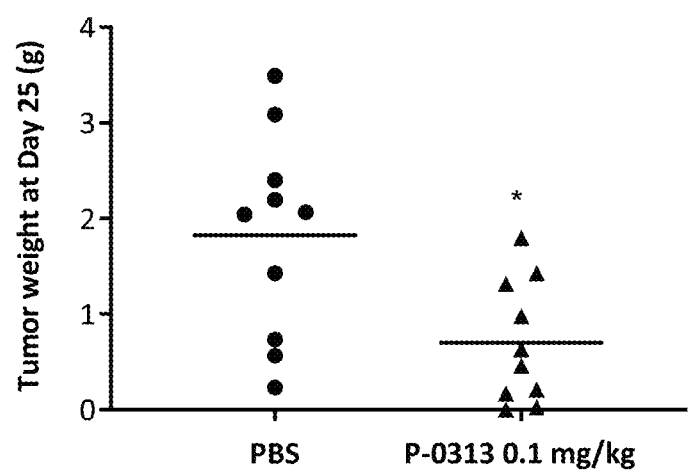
Figure 29A:
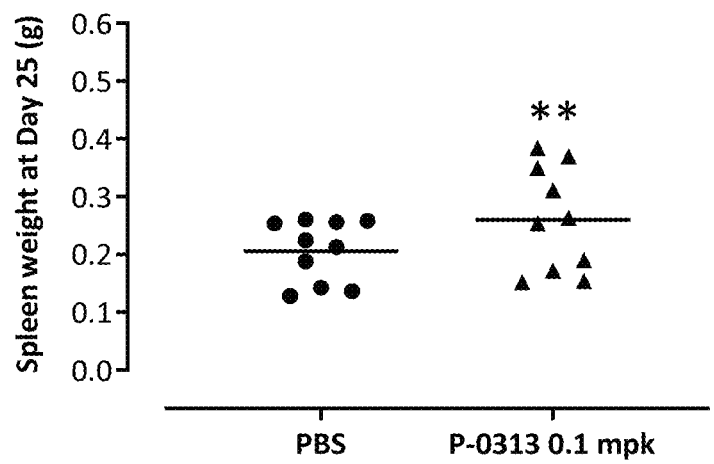
FIG. 29 depicts the spleen weights and the percent change of body weights in CT26 tumor-bearing mice treated with P-0313. Mice were given vehicle (PBS) or P-0313 (0.1 mg/kg) Q5D for five injections three days after CT26 tumor cell implantation. (A) Spleen weighs on day 25. (B) Percent change of body weights over 25 days. Data are expressed as mean±SEM. Statistical analysis was performed by one-way anova followed by Tukey's post hoc test. ** p<0.01, compared to PBS group.
Figure 29B:
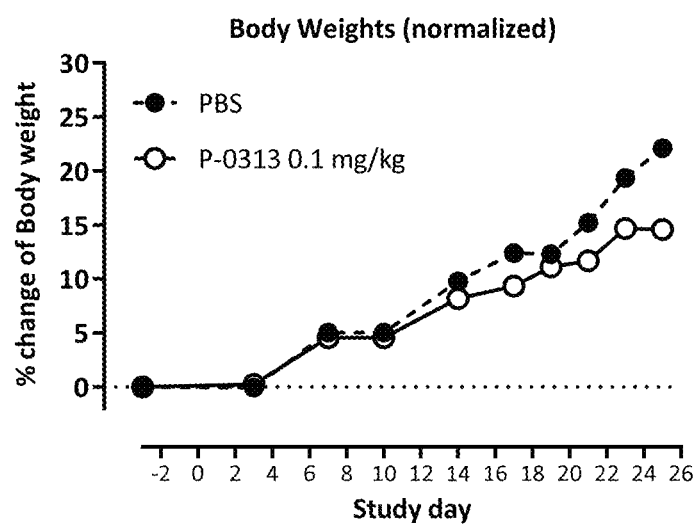

Effect of an IL-15/IL-15Rα Fc Fusion Protein on Non-Established CT26 Solid Tumor Growth in Balb/C Mice A similar study was conducted in non-established CT26 tumor model to confirm anti-tumor efficacy of P-0313. Three days after tumor cell subcutaneous engraftment with 1×10$^5$ CT26 cells, mice received intraperitoneal injection of vehicle (PBS) or P-0313 (0.1 mg/kg) every 5 days for a total of 5 injections. Mice were terminated at Day 25 and tumors were measured two-three times a week Similar as seen in established CT26 tumor model (Example 14), P-0313 demonstrated marked inhibition of tumor growth (FIG. 28A) and significant reduction in solid tumor mass (FIG. 28B). With 5 repeated doses, mice treated with P-0313 showed moderate increase in spleen weight (FIG. 29A) and no significant reduction in body weight gain (FIG. 29B), suggesting P-0313 is well tolerated.

Overall, these data corroborated that P-0313 is an effective immunotherapeutic against solid and liquid tumor as well as tumor cell metastasis with a well-tolerated safety profile.

All of the articles and methods disclosed and claimed herein can be made and executed without undue experimentation in light of the present disclosure. While the articles and methods of this disclosure have been described in terms of preferred embodiments, it will be apparent to those of skill in the art that variations may be applied to the articles and methods without departing from the spirit and scope of the disclosure. All such variations and equivalents apparent to those skilled in the art, whether now existing or later developed, are deemed to be within the spirit and scope of the disclosure as defined by the appended claims. All patents, patent applications, and publications mentioned in the specification are indicative of the levels of those of ordinary skill in the art to which the disclosure pertains. All patents, patent applications, and publications are herein incorporated by reference in their entirety for all purposes and to the same extent as if each individual publication was specifically and individually indicated to be incorporated by reference in its entirety for any and all purposes. The disclosure illustratively described herein suitably may be practiced in the absence of any element(s) not specifically disclosed herein. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

Sequence Listings

The nucleic and amino acid sequences listed in the accompanying sequence listing are shown using standard letter abbreviations for nucleotide bases and three letter code for amino acids, as defined in 37 C.F.R. 1.822.

SEQ ID NO: 1 is a human IL-15 precursor amino acid sequence.
SEQ ID NO: 2 is a human IL-15 mature form amino acid sequence.
SEQ ID NO: 3 is a human IL-15Rα amino acid sequence.
SEQ ID NO: 4 is a human IL-15Rα, extracellular domain amino acid sequence.
SEQ ID NO: 5 is a human IL-15Rα, sushi domain+amino acid sequence.
SEQ ID NO: 6 is a human IgG1-Fc amino acid sequence.
SEQ ID NO: 7 is a Knob-Fc amino acid sequence.
SEQ ID NO: 8 is a Hole-Fc amino acid sequence.
SEQ ID NOS: 9-12 are the amino acid sequences of various peptide linkers.
SEQ ID NO: 13 is the amino acid sequence of a Hole-Fc-Linker 1-IL-15 chain.
SEQ ID NO: 14 is the amino acid sequence of a Knob-Fc-Linker 1-IL-15Rα-Sushi+chain.
SEQ ID NO: 15 is the amino acid sequence of an IL-15-Linker 4-Hole-Fc chain.
SEQ ID NO: 16 is the amino acid sequence of an IL-15Rα-Sushi+-Linker 4-Knob-Fc chain.
SEQ ID NO: 17 is the amino acid sequence of a Knob-Fc-linker 2-IL-15Rα-Sushi+chain.
SEQ ID NO: 18 is the amino acid sequence of a Hole-Fc-Linker 2-IL-15 chain.
SEQ ID NO: 19 is the amino acid sequence of an IL-15-Linker 3-Hole-Fc chain.
SEQ ID NO: 20 is the amino acid sequence of a Fc-Linker 3-IL-15 chain.
SEQ ID NO: 21 is the amino acid sequence of an IL-15-Linker 3-Fc chain.
SEQ ID NO: 22 is the amino acid sequence of a Knob-Fc-Linker 2-IL-15Rα-Sushi+chain.
SEQ ID NO: 23 is the amino acid sequence of a Fc-Linker 2-IL-15Rα-Sushi+chain.
SEQ ID NOS: 24-45 are the amino acid sequences of various IL-15 variant polypeptides.
SEQ ID NO: 46 is the amino acid sequence of a Fc-Linker 3-IL-15 S58D chain.
SEQ ID NO: 47 is the amino acid sequence of a peptide linker.
SEQ ID NO: 48 is the amino acid sequence of a Hole-Fc-Linker 3-IL-15-S58D chain
SEQ ID NO: 49 is the amino acid sequence of an IL-15-S58D-Linker 3-Hole-Fc chain.
SEQ ID NO: 50 is the amino acid sequence of an IL-15-S58D-Linker 3-Fc chain.
SEQ ID NO: 51 is the amino acid sequence of an IL-15Rα-Sushi+Linker 2-Knob-Fc chain.
SEQ ID NO: 52 is the amino acid sequence of an IL-15Rα-Sushi+Linker 2-Fc chain.
SEQ ID NO: 53 is the amino acid sequence of a Hole-Fc-Linker 1-IL-15-S58D chain.
SEQ ID NO: 54 is the amino acid sequence of a Hole-Fc-Linker 3-IL-15 chain
SEQ ID NO: 55 is the amino acid sequence of a Knob-Fc-Linker 1-IL-15 chain.
SEQ ID NOS: 56-63 are nucleotide sequences encoding various IL-15/IL-15Rα-Fc fusion chains.
SEQ ID NOS 64 and 65 are the amino acid sequences of the two polypeptide chains of the Benchmark.

SEQUENCE LISTINGS

Human IL-15 precursor sequence
MRISKPHLRSISIQCYLCLLLNSHFLTEAGIHVFILGCFSAGLPKTEANWVNVISDLKKIEDLIQSM
HIDATLYTESDVHPSCKVTAMKCFLLELQVISLESGDASIHDTVENLIILANNSLSSNGNVTESGC
KECEELEEKNIKEFLQSFVHIVQMFINTS (SEQ ID NO: 1)

Human IL-15 mature form sequence
NWVNVISDLKKIEDLIQSMHIDATLYTESDVHPSCKVTAMKCFLLELQVISLESGDASIHDTVENLI
ILANNSLSSNGNVTESGCKECEELEEKNIKEFLQSFVHIVQMFINTS (SEQ ID NO: 2)

Human IL-15Rα sequence
MAPRRARGCRTLGLPALLLLLLLRPPATRGITCPPPMSVEHADIWVKSYSLYSRERYICNSGFK
RKAGTSSLTECVLNKATNVAHWTTPSLKCIRDPALVHQRPAPPSTVTTAGVTPQPESLSPSGK
EPAASSPSSNNTAATTAAIVPGSQLMPSKSPSTGTTEISSHESSHGTPSQTTAKNWELTASASH
QPPGVYPQGHSDTTVAISTSTVLLCGLSAVSLLACYLKSRQTPPLASVE
MEAMEALPVTWGTSSRDEDLENCSHHL (SEQ ID NO: 3)

Human IL-15Rα, extracellular domain
ITCPPPMSVEHADIWVKSYSLYSRERYICNSGFKRKAGTSSLTECVLNKATNVAHWTTPSLKCI
RDPALVHQRPAPPSTVTTAGVTPQPESLSPSGKEPAASSPSSNNTAATTAAIVPGSQLMPSKS
PSTGTTEISSHESSHGTPSQTTAKNWELTASASHQPPGVYPQGHSDTT (SEQ ID NO: 4)

Human IL-15Rα, sushi domain+
ITCPPPMSVEHADIWVKSYSLYSRERYICNSGFKRKAGTSSLTECVLNKATNVAHWTTPSLKCI
RDPALVHQRPAPP(SEQ ID NO: 5)

Human IgG1-Fc
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPG (SEQ ID NO: 6)

Knob-Fc
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVCTLPPSREEMTKNQVSLWCLVKGFYPSDIAVEWESNGQPENNYKTTPPVLDSDGSFFLYS
KLTVDKSRWQQGNVFSCSVMHEALHNHYTQKSLSLSPG (SEQ ID NO: 7)

Hole-Fc
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPCREEMTKNQVSLSCAVKGFYPSDIAVEWESNGQPENNYKTTPPVLDSDGSFFLVSK
LTVDKSRWQQGNVFSCSVMHEALHNHYTQKSLSLSPG (SEQ ID NO: 8)

Peptide Linker Sequence
EPKSSDKTHTSPPSP (SEQ ID NO: 9)

Peptide Linker Sequence
GGGGSGGGGS (SEQ ID NO: 10)

Peptide Linker Sequence
GGGGSGGGGSGGGGS (SEQ ID NO: 11)

Peptide Linker Sequence
G (SEQ ID NO: 12)

Hole-Fc-Linker 1-IL-15 chain
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPCREEMTKNQVSLSCAVKGFYPSDIAVEWESNGQPENNYKTTPPVLDSDGSFFLVSK
LTVDKSRWQQGNVFSCSVMHEALHNHYTQKSLSLSPGEPKSSDKTHTSPPSPNWVNVISDLK
KIEDLIQSMHIDATLYTESDVHPSCKVTAMKCFLLELQVISLESGDASIHDTVENLIILANNSLSSN
GNVTESGCKECEELEEKNIKEFLQSFVHIVQMFINTS (SEQ ID NO: 13)

Knob-Fc-IL-Linker1-1L-15Rα-Sushi+ chain
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVCTLPPSREEMTKNQVSLWCLVKGFYPSDIAVEWESNGQPENNYKTTPPVLDSDGSFFLYS
KLTVDKSRWQQGNVFSCSVMHEALHNHYTQKSLSLSPGEPKSSDKTHTSPPSPITCPPPMSV
EHADIWVKSYSLYSRERYICNSGFKRKAGTSSLTECVLNKATNVAHWTTPSLKCIRDPALVHQR
PAPP (SEQ ID NO: 14)

IL-15-Linker 4-Hole-Fc chain
NWVNVISDLKKIEDLIQSMHIDATLYTESDVHPSCKVTAMKCFLLELQVISLESGDASIHDTVENLI
ILANNSLSSNGNVTESGCKECEELEEKNIKEFLQSFVHIVQMFINTSGCPPCPAPEAAGAPSVFL
FPPKPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPCREEMTKNQVSLSCA
VKGFYPSDIAVEWESNGQPENNYKTTPPVLDSDGSFFLVSKLTVDKSRWQQGNVFSCSVMHE
ALHNHYTQKSLSLSPG (SEQ ID NO: 15)

SEQUENCE LISTINGS

IL-15Ra-Sushi+-Linker 4-Knob-Fc chain
ITCPPPMSVEHADIWVKSYSLYSRERYICNSGFKRKAGTSSLTECVLNKATNVAHWTTPSLKCI
RDPALVHQRPAPPGCPPCPAPEAAGAPSVFLFPPKPKDTLMISRTPEVTCVVVDVSHEDPEVK
FNWYVDGVEVHNAKTKPREEQYNSTYRVVSVLTVLHQDW LNGKEYKCKVSNKALPAPIEKTIS
KAKGQPREPQVCTLPPSREEMTKNQVSLWCLVKGFYPSDIAVEWESNGQPENNYKTTPPVLD
SDGSFFLYSKLTVDKSRWQQGNVFSCSVMHEALHNHYTQKSLSLSPG (SEQ ID NO: 16)

Knob-Fc-linker 2-IL-i5Rα-+ chain
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVCTLPPSREEMTKNQVSLWCLVKGFYPSDIAVEWESNGQPENNYKTTPPVLDSDGSFFLYS
KLTVDKSRWQQGNVFSCSVMHEALHNHYTQKSLSLSPGGGGGSGGGGSITCPPPMSVEHAD
IWVKSYSLYSRERYICNSGFKRKAGTSSLTECVLNKATNVAHWTTPSLKCIRDPALVHQRPAPP
(SEQ ID NO: 17)

Hole-Fc-Linker 2-IL-15 chain
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPCREEMTKNQVSLSCAVKGFYPSDIAVEWESNGQPENNYKTTPPVLDSDGSFFLVSK
LTVDKSRWQQGNVFSCSVMHEALHNHYTQKSLSLSPGGGGGSGGGGSNWVNVISDLKKIED
LIQSMHIDATLYTESDVHPSCKVTAMKCFLLELQVISLESGDASIHDTVENLIILANNSLSSNGNV
TESGCKECEELEEKNIKEFLQSFVHIVQMFINTS (SEQ ID NO: 18)

IL-15-Linker 3-Hole-Fc chain
NWVNVISDLKKIEDLIQSMHIDATLYTESDVHPSCKVTAMKCFLLELQVISLESGDASIHDTVENLI
ILANNSLSSNGNVTESGCKECEELEEKNIKEFLQSFVHIVQMFINTSGGGGSGGGGSGGGGSC
PPCPAPEAAGAPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREPQVYTLP
PCREEMTKNQVSLSCAVKGFYPSDIAVEWESNGQPENNYKTTPPVLDSDGSFFLVSKLTVDKS
RWQQGNVFSCSVMHEALHNHYTQKSLSLSPG (SEQ ID NO: 19)

Fc-Linker 3-IL-15 chain
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGGSGGGGSGGGGSNWVNVISD
LKKIEDLIQSMHIDATLYTESDVHPSCKVTAMKCFLLELQVISLESGDASIHDTVENLIILANNSLS
SNGNVTESGCKECEELEEKNIKEFLQSFVHIVQMFINTS (SEQ ID NO: 20)

IL-15-Linker 3-Fc chain
NWVNVISDLKKIEDLIQSMHIDATLYTESDVHPSCKVTAMKCFLLELQVISLESGDASIHDTVENLI
ILANNSLSSNGNVTESGCKECEELEEKNIKEFLQSFVHIVQMFINTSGGGGSGGGGSGGGGSC
PPCPAPEAAGAPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREPQVYTLP
PSRDELTKNQVSLTCAVKGFYPSDIAVEWESNGQPENNYKTTPPVLDSDGSFFLVSKLTVDKS
RWQQGNVFSCSVMHEALHNHYTQKSLSLSPG (SEQ ID NO: 21)

Knob-Fc-Linker 2-IL-15Rα-Sushi+ chain
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVCTLPPSREEMTKNQVSLWCLVKGFYPSDIAVEWESNGQPENNYKTTPPVLDSDGSFFLYS
KLTVDKSRWQQGNVFSCSVMHEALHNHYTQKSLSLSPGGGGGSGGGGSITCPPPMSVEHAD
IWVKSYSLYSRERYICNSGFKRKAGTSSLTECVLNKATNVAHWTTPSLKCIRDPALVHQRPAPP
(SEQ ID NO: 22)

Fc-Linker 2-IL-i5Rα-Sushi+chain
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGGSGGGGSITCPPPMSVEHADI
WVKSYSLYSRERYICNSGFKRKAGTSSLTECVLNKATNVAHWTTPSLKCIRDPALVHQRPAPP
(SEQ ID NO: 23)

Human IL-15 S58D Variant Polypeptide
NWVNVISDLKKIEDLIQSMHIDATLYTESDVHPSCKVTAMKCFLLELQVISLESGDADIHDTVENL
IILANNSLSSNGNVTESGCKECEELEEKNIKEFLQSFVHIVQMFINTS (SEQ ID NO: 24)

Human IL-15 I62D Variant Polypeptide
NWVNVISDLKKIEDLIQSMHIDATLYTESDVHPSCKVTAMKCFLLELQVISLESGDASIHDDVENL
IILANNSLSSNGNVTESGCKECEELEEKNIKEFLQSFVHIVQMFINTS (SEQ ID NO: 25)

Human IL-15 V63F Variant Polypeptide
NWVNVISDLKKIEDLIQSMHIDATLYTESDVHPSCKVTAMKCFLLELQVISLESGDASIHDTFENLI
ILANNSLSSNGNVTESGCKECEELEEKNIKEFLQSFVHIVQMFINTS (SEQ ID NO: 26)

SEQUENCE LISTINGS

Human IL-15 I67V Variant Polypeptide
NWVNVISDLKKIEDLIQSMHIDATLYTESDVHPSCKVTAMKCFLLELQVISLESGDASIHDTVENL
VILANNSLSSNGNVTESGCKECEELEEKNIKEFLQSFVHIVQMFINTS (SEQ ID NO: 27)

Human IL-15 I68F Variant Polypeptide
NWVNVISDLKKIEDLIQSMHIDATLYTESDVHPSCKVTAMKCFLLELQVISLESGDASIHDTVENLI
FLANNSLSSNGNVTESGCKECEELEEKNIKEFLQSFVHIVQMFINTS (SEQ ID NO: 28)

Human IL-15 I68K Variant Polypeptide
NWVNVISDLKKIEDLIQSMHIDATLYTESDVHPSCKVTAMKCFLLELQVISLESGDASIHDTVENLI
KLANNSLSSNGNVTESGCKECEELEEKNIKEFLQSFVHIVQMFINTS (SEQ ID NO: 29)

Human IL-15 I68D Variant Polypeptide
NWVNVISDLKKIEDLIQSMHIDATLYTESDVHPSCKVTAMKCFLLELQVISLESGDASIHDTVENLI
DLANNSLSSNGNVTESGCKECEELEEKNIKEFLQSFVHIVQMFINTS (SEQ ID NO: 30)

Human IL-15 I68H Variant Polypeptide
NWVNVISDLKKIEDLIQSMHIDATLYTESDVHPSCKVTAMKCFLLELQVISLESGDASIHDTVENLI
HLANNSLSSNGNVTESGCKECEELEEKNIKEFLQSFVHIVQMFINTS (SEQ ID NO: 31)

Human IL-15 Q108A Variant Polypeptide
NWVNVISDLKKIEDLIQSMHIDATLYTESDVHPSCKVTAMKCFLLELQVISLESGDASIHDTVENLI
ILANNSLSSNGNVTESGCKECEELEEKNIKEFLQSFVHIVAMFINTS (SEQ ID NO: 32)

Human IL-15 Q108M Variant Polypeptide
NWVNVISDLKKIEDLIQSMHIDATLYTESDVHPSCKVTAMKCFLLELQVISLESGDASIHDTVENLI
ILANNSLSSNGNVTESGCKECEELEEKNIKEFLQSFVHIVMMFINTS (SEQ ID NO: 33)

Human IL-15 Q108S Variant Polypeptide
NWVNVISDLKKIEDLIQSMHIDATLYTESDVHPSCKVTAMKCFLLELQVISLESGDASIHDTVENLI
ILANNSLSSNGNVTESGCKECEELEEKNIKEFLQSFVHIVSMFINTS (SEQ ID NO: 34)

Human IL-15 Qi085/D301 Variant Polypeptide
NWVNVISDLKKIEDLIQSMHIDATLYTESTVHPSCKVTAMKCFLLELQVISLESGDASIHDTVENLI
ILANNSLSSNGNVTESGCKECEELEEKNIKEFLQSFVHIVSMFINTS (SEQ ID NO: 35)

Human IL-15 Q108S/V31Y Variant Polypeptide
NWVNVISDLKKIEDLIQSMHIDATLYTESDYHPSCKVTAMKCFLLELQVISLESGDASIHDTVENLI
ILANNSLSSNGNVTESGCKECEELEEKNIKEFLQSFVHIVSMFINTS (SEQ ID NO: 36)

Human IL-15 Q108S/H32E Variant Polypeptide
NWVNVISDLKKIEDLIQSMHIDATLYTESDVEPSCKVTAMKCFLLELQVISLESGDASIHDTVENLI
ILANNSLSSNGNVTESGCKECEELEEKNIKEFLQSFVHIVSMFINTS (SEQ ID NO: 37)

Human IL-15 Q108S/D30T/V31Y/H32E Variant Polypeptide
NWVNVISDLKKIEDLIQSMHIDATLYTESTYEPSCKVTAMKCFLLELQVISLESGDASIHDTVENLI
ILANNSLSSNGNVTESGCKECEELEEKNIKEFLQSFVHIVSMFINTS (SEQ ID NO: 38)

Human IL-15 deletion 111-114 Variant Polypeptide
NWVNVISDLKKIEDLIQSMHIDATLYTESDVHPSCKVTAMKCFLLELQVISLESGDASIHDTVENLI
ILANNSLSSNGNVTESGCKECEELEEKNIKEFLQSFVHIVQMF (SEQ ID NO: 39)

Human IL-15 deletion 109-114 Variant Polypeptide
NWVNVISDLKKIEDLIQSMHIDATLYTESDVHPSCKVTAMKCFLLELQVISLESGDASIHDTVENLI
ILANNSLSSNGNVTESGCKECEELEEKNIKEFLQSFVHIVQ (SEQ ID NO: 40)

Human IL-15 deletion 108-114 Variant Polypeptide
NWVNVISDLKKIEDLIQSMHIDATLYTESDVHPSCKVTAMKCFLLELQVISLESGDASIHDTVENLI
ILANNSLSSNGNVTESGCKECEELEEKNIKEFLQSFVHIV (SEQ ID NO: 41)

Human IL-15 deletion 105-114 Variant Polypeptide
NWVNVISDLKKIEDLIQSMHIDATLYTESDVHPSCKVTAMKCFLLELQVISLESGDASIHDTVENLI
ILANNSLSSNGNVTESGCKECEELEEKNIKEFLQSFV (SEQ ID NO: 42)

Human IL-15 Insertion 'GS' after N95 Variant Polypeptide
NWVNVISDLKKIEDLIQSMHIDATLYTESDVHPSCKVTAMKCFLLELQVISLESGDASIHDTVENLI
ILANNSLSSNGNVTESGCKECEELEEKNGSIKEFLQSFVHIVQMFINTS (SEQ ID NO: 43)

Human IL-15 Insertion 'GGSGG' after N95 Variant Polypeptide
NWVNVISDLKKIEDLIQSMHIDATLYTESDVHPSCKVTAMKCFLLELQVISLESGDASIHDTVENLI
ILANNSLSSNGNVTESGCKECEELEEKNGGSGGIKEFLQSFVHIVQMFINTS (SEQ ID NO: 44)

Human IL-15 Insertion 'GSSGGSGGS' after N95 Variant Polypeptide
NWVNVISDLKKIEDLIQSMHIDATLYTESDVHPSCKVTAMKCFLLELQVISLESGDASIHDTVENLI
ILANNSLSSNGNVTESGCKECEELEEKNGSSGSSGGSIKEFLQSFVHIVQMFINTS (SEQ ID NO: 45)

SEQUENCE LISTINGS

Fc-Linker 3-IL-15 558D chain
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGGSGGGGSNWVNVISD
LKKIEDLIQSMHIDATLYTESDVHPSCKVTAMKCFLLELQVISLESGDADIHDTVENLIILANNSLS
SNGNVTESGCKECEELEEKNIKEFLQSFVHIVQMFINTS (SEQ ID NO: 46)

Peptide Linker Sequence
GGGGSGGGG (SEQ ID NO: 47)

Hole-Fc-Linker 3-IL-15 558D chain
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPCREEMTKNQVSLSCAVKGFYPSDIAVEWESNGQPENNYKTTPPVLDSDGSFFLVSK
LTVDKSRWQQGNVFSCSVMHEALHNHYTQKSLSLSPGGGGSGGGGSGGGGSNWVNVISD
LKKIEDLIQSMHIDATLYTESDVHPSCKVTAMKCFLLELQVISLESGDADIHDTVENLIILANNSLS
SNGNVTESGCKECEELEEKNIKEFLQSFVHIVQMFINTS (SEQ ID NO: 48)

IL-15 558D-Linker 3-Hole-Fc chain
NWVNVISDLKKIEDLIQSMHIDATLYTESDVHPSCKVTAMKCFLLELQVISLESGDADIHDTVENL
IILANNSLSSNGNVTESGCKECEELEEKNIKEFLQSFVHIVQMFINTSGGGGSGGGGSGGGGSC
PPCPAPEAAGAPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREPQVYTLP
PCREEMTKNQVSLSCAVKGFYPSDIAVEWESNGQPENNYKTTPPVLDSDGSFFLVSKLTVDKS
RWQQGNVFSCSVMHEALHNHYTQKSLSLSPG (SEQ ID NO: 49)

IL-15 558D-Linker 3-Fc chain
NWVNVISDLKKIEDLIQSMHIDATLYTESDVHPSCKVTAMKCFLLELQVISLESGDADIHDTVENL
IILANNSLSSNGNVTESGCKECEELEEKNIKEFLQSFVHIVQMFINTSGGGGSGGGGSGGGGSC
PPCPAPEAAGAPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREPQVYTLP
PSRDELTKNQVSLTCAVKGFYPSDIAVEWESNGQPENNYKTTPPVLDSDGSFFLVSKLTVDKS
RWQQGNVFSCSVMHEALHNHYTQKSLSLSPG (SEQ ID NO: 50)

IL-15Ra-Sushi+Linker 2-Knob-Fc chain
ITCPPPMSVEHADIWVKSYSLYSRERYICNSGFKRKAGTSSLTECVLNKATNVAHWTTPSLKCI
RDPALVHQRPAPPGGGGSGGGGSCPPCPAPEAAGAPSVFLFPPKPKDTLMISRTPEVTCVVV
DVSHEDPEVKFNWYVDGVEVHNAKTKPREEQYNSTYRVVSVLTVLHQDWLNGKEYKCKVSN
KALPAPIEKTISKAKGQPREPQVCTLPPSREEMTKNQVSLWCLVKGFYPSDIAVEWESNGQPE
NNYKTTPPVLDSDGSFFLYSKLTVDKSRWQQGNVFSCSVMHEALHNHYTQKSLSLSPG
(SEQ ID NO: 51)

IL-15Ra-Sushi+Linker 2-Fc chain
ITCPPPMSVEHADIWVKSYSLYSRERYICNSGFKRKAGTSSLTECVLNKATNVAHWTTPSLKCI
RDPALVHQRPAPPGGGGSGGGGSCPPCPAPEAAGAPSVFLFPPKPKDTLMISRTPEVTCVVV
DVSHEDPEVKFNWYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQKSLSLSPG
(SEQ ID NO: 52)

Hole-Fc-Linker 1-IL-15-558D chain
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPCREEMTKNQVSLSCAVKGFYPSDIAVEWESNGQPENNYKTTPPVLDSDGSFFLVSK
LTVDKSRWQQGNVFSCSVMHEALHNHYTQKSLSLSPGEPKSSDKTHTSPPSPNWVNVISDLK
KIEDLIQSMHIDATLYTESDVHPSCKVTAMKCFLLELQVISLESGDADIHDTVENLIILANNSLSSN
GNVTESGCKECEELEEKNIKEFLQSFVHIVQMFINTS (SEQ ID NO: 53)

Hole-Fc-Linker 3-IL-15 chain
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPCREEMTKNQVSLSCAVKGFYPSDIAVEWESNGQPENNYKTTPPVLDSDGSFFLVSK
LTVDKSRWQQGNVFSCSVMHEALHNHYTQKSLSLSPGGGGGSGGGGSGGGGSNWVNVISD
LKKIEDLIQSMHIDATLYTESDVHPSCKVTAMKCFLLELQVISLESGDASIHDTVENLIILANNSLS
SNGNVTESGCKECEELEEKNIKEFLQSFVHIVQMFINTS (SEQ ID NO: 54)

Knob-Fc-Linker 1-IL-15 chain
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVCTLPPSREEMTKNQVSLWCLVKGFYPSDIAVEWESNGQPENNYKTTPPVLDSDGSFFLYS
KLTVDKSRWQQGNVFSCSVMHEALHNHYTQKSLSLSPGEPKSSDKTHTSPPSPNWVNVISDL
KKIEDLIQSMHIDATLYTESDVHPSCKVTAMKCFLLELQVISLESGDASIHDTVENLIILANNSLSS
NGNVTESGCKECEELEEKNIKEFLQSFVHIVQMFINTS (SEQ ID NO: 55)

SEQUENCE LISTINGS

Nucleotide sequence of P-0313 Chain 1
<u>atggatatgcgggtgcctgctcagctgctgggcctgctgctgctgtggctgcgaggggctagatgtgataaaactcatacttgtcctccat
gcccagcacctgaggcagcaggcgcccatccgtgttcctgtttcccccctaagcccaaggacacactgatgatctcccgtacgccag
aggtgacatgcgtggtggtggacgtgagccacgaggaccccgaggtgaagtttaactggtacgtggacggcgtggaggtgcacaat
gccaagacaaagcctagggaggagcagtacaattctacctatcgcgtggtgagcgtgctgacagtgctgcaccaggattggctgaa
cggcaaggagtataagtgcaaggtgtccaataaggccctgcctgccccaatcgagaagaccatctctaaggccaagggccagccc
agagagcctcaggtgtacacactgcctccaagcagagacgagctgaccaagaaccaggtgtccctgacatgtctggtgaagggctt
ctatccctctgatatcgccgtggagtgggagagcaatggccagcctgagaacaattacaagaccacaccccctgtgctggacagcg
atggctccttctttctgtattccaagctgaccgtggataagtctcggtggcagcagggcaacgtgttttcctgctctgtgatgcacgaagca
ctgcataaccactacacccagaagagcctgagcctgtcccccggggaggcggaggatctggtggcggaggaagcggaggcgg
cggctccaactgggtgaatgtgatcagcgacctgaagaagatcgaggatctgatccagtccatgcacatcgacgccaccctgtatac
agagtctgatgtgcaccccagctgcaaggtgaccgccatgaagtgttttctgctggagctgcaggtcatcagcctggagtccggcgac
gcagacatccacgataccgtggagaatctgatcatcctggccaacaattccctgtctagcaacggcaatgtgacagagtctggctgca
aggagtgtgaggagctggaggagaagaatatcaaagagttcctgcagagtttcgtccacatcgtccagatgtttatcaatacctca</u>
(SEQ ID NO: 56)

Nucleotide sequence of IL-15RαSushi+ domain (Chain 2 of fusion proteins P-0313, P-0234, P-0666, and P-0668)
atggctccacggcgggctcgggctgtcgcaccctgggctgcctgctctgctgctgctgctgctgagaccacctgctacacgcg
gatcacctgcccacctccaatgagcgtggagcacgcagacatctgggtgaagtcttacagcctgtatagccgggagagatacatct
gcaactccggcttcaagcggaaggccggcaccagctccctgacagagtgcgtgctgaacaaggccacaaatgtggcccactgga
ccacaccttccctgaagtgcatccgggaccccgccctggtgcaccagcgcccagcccccccct (SEQ ID NO: 57)

Nucleotide sequence of P-0234 Chain 1
<u>atggatatgcgggtgcctgctcagctgctgggcctgctgctgctgtggctgcgaggggctagatgtgataaaactcatacttgtcctccat
gcccagcacctgaggcagcaggcgcccatccgtgttcctgtttcccccctaagcccaaggacacactgatgatctcccgtacgccag
aggtgacatgcgtggtggtggacgtgagccacgaggaccccgaggtgaagtttaactggtacgtggacggcgtggaggtgcacaat
gccaagacaaagcctagggaggagcagtacaattctacctatcgcgtggtgagcgtgctgacagtgctgcaccaggattggctgaa
cggcaaggagtataagtgcaaggtgtccaataaggccctgcctgccccaatcgagaagaccatctctaaggccaagggccagccc
agagagcctcaggtgtacacactgcctccaagcagagacgagctgaccaagaaccaggtgtccctgacatgtctggtgaagggctt
ctatccctctgatatcgccgtggagtgggagagcaatggccagcctgagaacaattacaagaccacaccccctgtgctggacagcg
atggctccttctttctgtattccaagctgaccgtggataagtctcggtggcagcagggcaacgtgttttcctgctctgtgatgcacgaagca
ctgcataaccactacacccagaagagcctgagcctgtcccccggggaggcggaggatctggtggcggaggaagcggaggcgg
cggctccaactgggtgaatgtgatcagcgacctgaagaagatcgaggatctgatccagtccatgcacatcgacgccaccctgtatac
agagtctgatgtgcaccccagctgcaaggtgaccgccatgaagtgttttctgctggagctgcaggtcatcagcctggagtccggcgac
gcaagcatccacgataccgtggagaatctgatcatcctggccaacaattccctgtctagcaacggcaatgtgacagagtctggctgca
aggagtgtgaggagctggaggagaagaatatcaaagagttcctgcagagtttcgtccacatcgtccagatgtttatcaatacctca</u>
(SEQ ID NO: 58)

Nucleotide sequence of P-0666 Chain 1
<u>atggatatgcgagtgcctgctcagctgctgggcctgctgctgctgtggctgcggggggctagatgcgataaaactcatacctgtcctcc
atgcccagcacctgaggcagcaggcgcccatccgtgttcctgtttcccccctaagcccaaggacaccctgatgatctctcgtacgccc
gaggtgacatgcgtggtggtggacgtgagccacgaggaccccgaggtgaagttcaactggtacgtggatggcgtggaggtgcaca
atgccaagacaaagcctcgggaggagcagtacaactccacctatagagtggtgtctgtgctgacagtgctgcaccaggactgctg
aacggcaaggagtacaagtgcaaggtgtccaataaggccctgccagcccccatcgagaagaccatcagcaaggccaaggggca
gcctagggagccacaggtgtataccctgccacctgccgcgaggagatgacaaagaaccaggtgtccctgtcttgtgccgtgaagg
gcttctaccccttctgacatcgccgtggagtgggagagcaatggccagccagagaacaattataagaccacacctccagtgctggact
ctgatggcagcttctttctggtgagcaagctgaccgtggataagtccaggtggcagcagggcaacgtgtttagctgtttccgtgatgcacg
aggccctgcacaatcactacacacagaagtctctgagcctgtcccccggggaggcggaggatctggtggcggaggaagcggag
gcggcggctccaactgggtgaatgtgatcagcgacctgaagaagatcgaggatctgatccagtccatgcacatcgacgcgcaccctgt
atacagagtctgatgtgcaccccagctgcaaggtgaccgccatgaagtgttttctgctggagctgcaggtcatcagcctggagtccgg
cgacgcagacatccacgataccgtggagaatctgatcatcctggccaacaattccctgtctagcaacggcaatgtgacagagtctgg
ctgcaaggagtgtgaggagctggaggagaagaatatcaaagagttcctgcagagtttcgtccacatcgtccagatgtttatcaatacct
ca</u> (SEQ ID NO: 59)

Nucleotide sequence of P-0666 Chain 3
<u>atggatatgcgggtgcctgctcagctgctgggcctgctgctgctgtggctgcgaggggctagatgtgataaaactcatacttgtcctccat
gcccagcacctgaggcagcaggcgcccatccgtgttcctgtttcccccctaagcccaaggacacactgatgatctcccgtacgccag
aggtgacatgcgtggtggtggacgtgtctcacgaggaccccgaggtgaagttcaactggtacgtggatgcgtggaggtgcacaatg
ccaagaccaagcccaggagaggcagtacaacagcacctatcgcgtggtgtccgtgctgacagtgctgcaccaggactggctgaa
cggcaaggagtataagtgcaaggtgtccaataaggccctgccagccccatcgagaagaccatcagcaaggcaaaggggcagc
ctcgggagccacaggtgtgcaccctgccaccctctagagaggagatgacaaagaaccaggtgagcctgtggtgtctggtgaaggg
cttctaccttccgacatcgccgtggagtgggagtctaatggccagccagagaacaattacaagaccacacctccagtgctggactct
gatggcagcttctttctgtattctaagctgaccgtggataagagcaggtggcagcagggcaacgtgttttcctgctctgtgatgcacgag
gccctgcacaatcactacacacagaagagcctgtccctgtctcccggg</u> (SEQ ID NO: 60)

Nucleotide sequence of P-0668 Chain 1
<u>atgtatcggatgcagctgctgtcttgtatcgctctgtcactggctctggtcactaat-
tctaactgggtcaatgtcatttctgatctgaagaagat</u>
cgaggacctgatccagagcatgcacatcgatgccaccctgtacacagagtccgacgtgcacccatcttgcaaggtgaccgcaatga
agtgttttcctgctggagctgcaggtcatcagcctggagagcggcgacgcagatatccacgataccgtggagaacctgatcatcctgg
caaacaattccctgagctccaacggaaatgtgacagagtctggatgcaaggagtgtgaggagctggaggagaagaacatcaagg
agttcctgcagtcttttgtgcacatcgtgcagatgttcattaatacatccggcggcggcggctccggcggcggcggctccggcggcgc
ggcagctgccccccttgtccagcccccgaggccgctggggcaccaagcgttcctgttcctccaaaaccaaaagatactctgatg
attagccgtacgccagaggtgacatgcgtggtggtggacgtgagccacgaggaccccgaggtgaagtttaactggtacgtggacgg
cgtggaggtgcacaatgccaagacaaagcctagggaggagcagtacaattctacctatcgcgtggtgagcgtgctgacagtgctgc
accaggattggctgaacggcaaggagtataagtgcaaggtgtccaataaggccctgcctgccccaatcgagaagaccatctctaag

SEQUENCE LISTINGS

```
gccaagggccagcccagagagcctcaggtgtacacactgcctccaagcagagacgagctgaccaagaaccaggtgtccctgac
atgtctggtgaaggcttctatccctctgatatcgccgtggagtgggagagcaatggccagcctgagaacaattacaagaccacacc
ccctgtgctggacagcgatggctccttctttctgtattccaagctgaccgtggataagtctcggtggcagcagggcaacgtgttttcctgct
ctgtgatgcacgaagcactgcataaccactacacccagaagagcctgagcctgtcccccggg (SEQ ID NO: 61)
```

Nucleotide sequence of P-0314 Chain 1
```
atggatatgcgggtgcctgctcagctgctgggcctgctgctgctgtggctgcgagggggctagatgtgataaaactcatacttgtcctccat
gccagcacctgaggcagcaggcgccccatccgtgttcctgtttccccctaagccaaggacacactgatgatctcccgtacgccag
aggtgacatgcgtggtggtggacgtgagccacgaggaccccgaggtgaagtttaactggtacgtggacggcgtggaggtgcacaat
gccaagacaaagcctagggaggagcagtacaattctacctatcgcgtggtgagcgtgctgacagtgctgcaccaggattggctgaa
cggcaaggagtataagtgcaaggtgtccaataaggccctgcctgccccaatcgagaagaccatctctaaggccaagggccagccc
agagagcctcaggtgtacacactgcctccaagcagagacgagctgaccaagaaccaggtgtccctgacatgtctggtgaagggctt
ctatccctctgatatcgccgtggagtgggagagcaatggccagcctgagaacaattacaagaccacacccctgtgctggacagcg
atggctccttctttctgtattccaagctgaccgtggataagtctcggtggcagcagggcaacgtgttttcctgctctgtgatgcacgaagca
ctgcataaccactacacccagaagagcctgagcctgtcccccggggcggcggcggcagcggaggcggcggctccatcacctgt
ccaccccctatgagcgtgagcacgccgatatctgggtgaagagctactccctgtatagccgggagagatatatctgcaattccggctt
taagcgcaaggccggcacctctagcctgacagagtgcgtgctgaacaaggccaccaatgtggcccactggacaaccccaagcct
gaagtgtattagagaccctgccctggtgcatcagcggcctgctccccca (SEQ ID NO: 62)
```

Nucleotide sequence of P-0314 Chain 2
```
atgtaccggatgcagctgctgtcctgcatcgccctgtctctggccctggtgaccaactctaattgggtgaacgtgatcagcgacctgaag
aagatcgaggatctgatccagtctatgcacatcgacgccaccctgtatacagagagcgatgtgcaccctcctgcaaggtgacagcc
atgaagtgtttcctgctggagctgcaggtcatcagcctggagagcggcgacgcagacatccacgataccgtggagaacctgatcatc
ctggccaataactccctgagctccaacggcaatgtgacagagtctggctgcaaggagtgtgaggagctggaggagaagaacatca
aggagttcctgcagagctttgtgcacatcgtgcagatgtttatcaatacctcc (SEQ ID NO: 63)
```

Benchmark Chain1
```
ITCPPPMSVEHADIWVKSYSLYSRERYICNSGFKRKAGTSSLTECVLNKATNVAHWTTPSLKCI
REPKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAK
GQPREPQVYTLPPSRDELTKNQVSLTCLVKGFYPSDIAVEWESNGQPENNYKTTPPVLDSDGS
FFLYSKLTVDKSRWQQGNVFSCSVMHEALHNHYTQKSLSLSPG (SEQ ID NO: 64)
```

Benchmark Chain 2
```
NWVNVISDLKKIEDLIQSMHIDATLYTESDVHPSCKVTAMKCFLLELQVISLESGDASIHDTVENLI
ILANDSLSSNGNVTESGCKECEELEEKNIKEFLQSFVHIVQMFINTS (SEQ ID NO: 65)
```

What is claimed is:

1. An isolated Interleukin-15 (IL-15) fusion protein complex comprising: (1) an IL-15 polypeptide (or variant thereof) linked to an Fc domain; and (2) an IL-15 Receptor alpha ("IL-15Rα") domain noncovalently linked to the IL-15 polypeptide to form an IL-15/IL-15Rα-Fc fusion protein complex; wherein the IL-15 polypeptide is an IL-15 variant polypeptide comprising a substitution of S to D at position 58 of SEQ ID NO: 2; wherein the fusion protein complex is selected from the group consisting of a fusion protein complex wherein the IL-15 polypeptide is linked to the C-terminus of the Fc domain and a fusion protein complex wherein the IL-15 polypeptide is linked to the N-terminus of the Fc domain.

2. The IL-15/IL-15Rα-Fc fusion protein complex according to claim 1, wherein the IL-15Rα domain is an IL-15 Receptor alpha Sushi ("IL-15RαSushi") domain and comprises an amino acid sequence that is at least 90% homologous to the sequence set forth in SEQ ID NO: 5.

3. The IL-15/IL-15Rα-Fc fusion protein complex according to claim 1, wherein the Fc domain is an Fc domain having an amino acid sequence selected from the group consisting of the amino acid sequences set forth in SEQ ID NO: 6, SEQ ID NO: 7 and SEQ ID NO: 8; and wherein the IL-15 polypeptide is covalently attached to an Fc domain by a peptide linker.

4. A pharmaceutical composition comprising an IL-15/IL-15Rα-Fc fusion protein according to claim 1 in admixture with a pharmaceutically acceptable carrier.

5. An isolated IL-15 fusion protein complex comprising: (1) an IL-15Rα domain linked to an Fc domain; and (2) an IL-15 polypeptide (or variant thereof) noncovalently linked to the IL-15Rα domain to form an IL-15/IL-15Rα-Fc fusion protein complex, wherein the IL-15 polypeptide is an IL-15 variant polypeptide comprising a substitution of S to D at position 58 of SEQ ID NO: 2; and wherein the fusion protein complex is selected from the group consisting of a fusion protein complex wherein the IL-15Rα domain is linked to the C-terminus of the Fc domain and a fusion protein complex wherein the IL-15Rα domain is linked to the N-terminus of the Fc domain.

6. The IL-15/IL-15Rα-Fc fusion protein complex according to claim 5, wherein the IL-15Rα domain is an IL-15 Receptor alpha Sushi ("IL-15RαSushi") domain and comprises an amino acid sequence that is at least 90% homologous to the sequence set forth in SEQ ID NO: 5.

7. The IL-15/IL-15Rα-Fc fusion protein complex according to claim 5, wherein the Fc domain is an Fc domain having an amino acid sequence selected from the group consisting of the amino acid sequences set forth in SEQ ID NO: 6, SEQ ID NO: 7 and SEQ ID NO: 8; and wherein the IL-15 polypeptide is covalently attached to an Fc domain by a peptide linker.

8. A pharmaceutical composition comprising an IL-15/IL-15Rα-Fc fusion protein according to claim 5 in admixture with a pharmaceutically acceptable carrier.

9. An isolated IL-15 fusion protein complex comprising: (1) two IL-15 polypeptides (or variants thereof) linked to two Fc domains; and (2) two IL-15Rα domains noncovalently linked to each IL-15 polypeptide to form a dimeric IL-15/IL-15Rα-Fc fusion protein complex; wherein the IL-15 polypeptide is an IL-15 variant polypeptide comprising a substitution of S to D at position 58 of SEQ ID NO: 2; wherein the dimeric fusion protein complex is selected from the group consisting of a dimeric fusion protein complex wherein the two IL-15 polypeptides are linked to the C-terminus of the two Fc domains and a dimeric fusion protein complex wherein the two IL-15 polypeptides are linked to the N-terminus of the two Fc domains.

10. A pharmaceutical composition comprising an IL-15/IL-15Rα-Fc fusion protein according to claim 9 in admixture with a pharmaceutically acceptable carrier.

11. An isolated IL-15 fusion protein complex comprising: (1) two IL-15Rα domains linked to two Fc domains; and (2) two IL-15 polypeptides (or variants thereof) noncovalently linked to the IL-15Rα domain to form a dimeric IL-15/IL-15Rα-Fc fusion protein complex, wherein at least one of the IL-15 polypeptides is an IL-15 variant polypeptide comprising an amino acid substitution of S to D at position 58 of SEQ ID NO: 2; and wherein the dimeric fusion protein complex is selected from the group consisting of a dimeric fusion protein complex wherein the two IL-15Rα domains are linked to the C-terminus of the two Fc domains and a dimeric fusion protein complex wherein the two IL-15Rα domains are linked to the N-terminus of the two Fc domains.

12. A pharmaceutical composition comprising an IL-15/IL-15Rα-Fc fusion protein according to claim 11 in admixture with a pharmaceutically acceptable carrier.

* * * * *

SEQUENCE LISTING

<160> NUMBER OF SEQ ID NOS: 65

<210> SEQ ID NO 1
<211> LENGTH: 162
<212> TYPE: PRT
<213> ORGANISM: Homo sapiens

<400> SEQUENCE: 1

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
        50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
                100                 105                 110

Asn Leu Ile Ile Leu Ala Asn Asn Ser Leu Ser Ser Asn Gly Asn Val
            115                 120                 125

Thr Glu Ser Gly Cys Lys Glu Cys Glu Glu Leu Glu Glu Lys Asn Ile
```

-continued

```
                130                 135                 140
Lys Glu Phe Leu Gln Ser Phe Val His Ile Val Gln Met Phe Ile Asn
145                 150                 155                 160

Thr Ser

<210> SEQ ID NO 2
<211> LENGTH: 114
<212> TYPE: PRT
<213> ORGANISM: Homo sapiens

<400> SEQUENCE: 2

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
                35                  40                  45

Val Ile Ser Leu Glu Ser Gly Asp Ala Ser Ile His Asp Thr Val Glu
            50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 3
<211> LENGTH: 267
<212> TYPE: PRT
<213> ORGANISM: Homo sapiens

<400> SEQUENCE: 3

Met Ala Pro Arg Arg Ala Arg Gly Cys Arg Thr Leu Gly Leu Pro Ala
1               5                   10                  15

Leu Leu Leu Leu Leu Leu Leu Arg Pro Ala Thr Arg Gly Ile Thr
                20                  25                  30

Cys Pro Pro Pro Met Ser Val Glu His Ala Asp Ile Trp Val Lys Ser
                35                  40                  45

Tyr Ser Leu Tyr Ser Arg Glu Arg Tyr Ile Cys Asn Ser Gly Phe Lys
            50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
                100                 105                 110

Ala Gly Val Thr Pro Gln Pro Glu Ser Leu Ser Pro Ser Gly Lys Glu
            115                 120                 125

Pro Ala Ala Ser Ser Pro Ser Ser Asn Asn Thr Ala Ala Thr Thr Ala
        130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175
```

```
Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Val Ala Ile
            195                 200                 205

Ser Thr Ser Thr Val Leu Leu Cys Gly Leu Ser Ala Val Ser Leu Leu
210                 215                 220

Ala Cys Tyr Leu Lys Ser Arg Gln Thr Pro Leu Ala Ser Val Glu
225                 230                 235                 240

Met Glu Ala Met Glu Ala Leu Pro Val Thr Trp Gly Thr Ser Ser Arg
            245                 250                 255

Asp Glu Asp Leu Glu Asn Cys Ser His His Leu
            260                 265

<210> SEQ ID NO 4
<211> LENGTH: 175
<212> TYPE: PRT
<213> ORGANISM: Homo sapiens

<400> SEQUENCE: 4

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
            115                 120                 125

Ser Thr Gly Thr Thr Glu Ile Ser Ser His Glu Ser Ser His Gly Thr
130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr
                165                 170                 175

<210> SEQ ID NO 5
<211> LENGTH: 77
<212> TYPE: PRT
<213> ORGANISM: Homo sapiens

<400> SEQUENCE: 5

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60
```

```
Arg Asp Pro Ala Leu Val His Gln Arg Pro Ala Pro Pro
65                  70                  75
```

<210> SEQ ID NO 6
<211> LENGTH: 226
<212> TYPE: PRT
<213> ORGANISM: Homo sapiens

<400> SEQUENCE: 6

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225
```

<210> SEQ ID NO 7
<211> LENGTH: 226
<212> TYPE: PRT
<213> ORGANISM: Artificial
<220> FEATURE:
<223> OTHER INFORMATION: Knob-Fc

<400> SEQUENCE: 7

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
```

```
                65                   70                  75                  80
Arg Val Val Ser Val Leu Thr Val Leu His Gln Asp Trp Leu Asn Gly
                    85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Cys Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
    210                 215                 220

Pro Gly
225

<210> SEQ ID NO 8
<211> LENGTH: 226
<212> TYPE: PRT
<213> ORGANISM: Artificial
<220> FEATURE:
<223> OTHER INFORMATION: Hole-Fc

<400> SEQUENCE: 8

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                    85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Cys Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190

Asp Lys Ser Arg Trp Gln Gln Gly Asn Val Phe Ser Cys Ser Val Met
```

-continued

```
                 195                 200                 205
His Glu Ala Leu His Asn His Tyr Thr Gln Lys Ser Leu Ser Leu Ser
        210                 215                 220

Pro Gly
225

<210> SEQ ID NO 9
<211> LENGTH: 15
<212> TYPE: PRT
<213> ORGANISM: Artificial
<220> FEATURE:
<223> OTHER INFORMATION: Peptide Linker Sequence

<400> SEQUENCE: 9

Glu Pro Lys Ser Ser Asp Lys Thr His Thr Ser Pro Pro Ser Pro
1               5                   10                  15

<210> SEQ ID NO 10
<211> LENGTH: 10
<212> TYPE: PRT
<213> ORGANISM: Artificial
<220> FEATURE:
<223> OTHER INFORMATION: Peptide Linker Sequence

<400> SEQUENCE: 10

Gly Gly Gly Gly Ser Gly Gly Gly Gly Ser
1               5                   10

<210> SEQ ID NO 11
<211> LENGTH: 15
<212> TYPE: PRT
<213> ORGANISM: Artificial
<220> FEATURE:
<223> OTHER INFORMATION: Peptide Linker Sequence

<400> SEQUENCE: 11

Gly Gly Gly Gly Ser Gly Gly Gly Gly Ser Gly Gly Gly Gly Ser
1               5                   10                  15

<210> SEQ ID NO 12
<211> LENGTH: 1
<212> TYPE: PRT
<213> ORGANISM: Artificial
<220> FEATURE:
<223> OTHER INFORMATION: Peptide Linker Sequence

<400> SEQUENCE: 12

Gly
1

<210> SEQ ID NO 13
<211> LENGTH: 355
<212> TYPE: PRT
<213> ORGANISM: Artificial
<220> FEATURE:
<223> OTHER INFORMATION: Hole-Fc-Linker 1-IL-15 chain

<400> SEQUENCE: 13

Asp Lys Thr His Thr Cys Pro Pro Cys Pro Ala Pro Glu Ala Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45
```

Glu Asp Pro Glu Val Lys Phe Asn Trp Tyr Val Asp Gly Val Glu Val
        50                  55                  60

His Asn Ala Lys Thr Lys Pro Arg Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Glu Pro Lys Ser Ser Asp Lys Thr His Thr Ser Pro Pro Ser
225                 230                 235                 240

Pro Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Glu Leu
            275                 280                 285

Gln Val Ile Ser Leu Glu Ser Gly Asp Ala Ser Ile His Asp Thr Val
290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser
355

<210> SEQ ID NO 14
<211> LENGTH: 318
<212> TYPE: PRT
<213> ORGANISM: Artificial
<220> FEATURE:
<223> OTHER INFORMATION: Knob-Fc-IL-Linker1-IL-15R??-Sushi+ chain

<400> SEQUENCE: 14

Asp Lys Thr His Thr Cys Pro Pro Cys Pro Ala Pro Glu Ala Ala Gly
 1               5                  10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

```
Glu Asp Pro Glu Val Lys Phe Asn Trp Tyr Val Asp Gly Val Glu Val
 50                  55                  60

His Asn Ala Lys Thr Lys Pro Arg Glu Gln Tyr Asn Ser Thr Tyr
 65                  70                  75                  80

Arg Val Val Ser Val Leu Thr Val Leu His Gln Asp Trp Leu Asn Gly
                     85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Cys Thr Leu Pro Pro Ser Arg Glu Glu Met Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                    165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
210                 215                 220

Pro Gly Glu Pro Lys Ser Ser Asp Lys Thr His Thr Ser Pro Pro Ser
225                 230                 235                 240

Pro Ile Thr Cys Pro Pro Met Ser Val Glu His Ala Asp Ile Trp
                245                 250                 255

Val Lys Ser Tyr Ser Leu Tyr Ser Arg Glu Arg Tyr Ile Cys Asn Ser
                260                 265                 270

Gly Phe Lys Arg Lys Ala Gly Thr Ser Ser Leu Thr Glu Cys Val Leu
                275                 280                 285

Asn Lys Ala Thr Asn Val Ala His Trp Thr Thr Pro Ser Leu Lys Cys
                290                 295                 300

Ile Arg Asp Pro Ala Leu Val His Gln Arg Pro Ala Pro Pro
305                 310                 315

<210> SEQ ID NO 15
<211> LENGTH: 336
<212> TYPE: PRT
<213> ORGANISM: Artificial
<220> FEATURE:
<223> OTHER INFORMATION: IL-15-Linker 4-Hole-Fc chain

<400> SEQUENCE: 15

Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
                35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                85                  90                  95
```

```
Lys Glu Phe Leu Gln Ser Phe Val His Ile Val Gln Met Phe Ile Asn
                100                 105                 110

Thr Ser Gly Cys Pro Pro Cys Pro Ala Pro Glu Ala Ala Gly Ala Pro
            115                 120                 125

Ser Val Phe Leu Phe Pro Pro Lys Pro Lys Asp Thr Leu Met Ile Ser
        130                 135                 140

Arg Thr Pro Glu Val Thr Cys Val Val Val Asp Val Ser His Glu Asp
145                 150                 155                 160

Pro Glu Val Lys Phe Asn Trp Tyr Val Asp Gly Val Glu Val His Asn
                165                 170                 175

Ala Lys Thr Lys Pro Arg Glu Glu Gln Tyr Asn Ser Thr Tyr Arg Val
            180                 185                 190

Val Ser Val Leu Thr Val Leu His Gln Asp Trp Leu Asn Gly Lys Glu
        195                 200                 205

Tyr Lys Cys Lys Val Ser Asn Lys Ala Leu Pro Ala Pro Ile Glu Lys
        210                 215                 220

Thr Ile Ser Lys Ala Lys Gly Gln Pro Arg Glu Pro Gln Val Tyr Thr
225                 230                 235                 240

Leu Pro Pro Cys Arg Glu Glu Met Thr Lys Asn Gln Val Ser Leu Ser
                245                 250                 255

Cys Ala Val Lys Gly Phe Tyr Pro Ser Asp Ile Ala Val Glu Trp Glu
            260                 265                 270

Ser Asn Gly Gln Pro Glu Asn Asn Tyr Lys Thr Thr Pro Pro Val Leu
        275                 280                 285

Asp Ser Asp Gly Ser Phe Phe Leu Val Ser Lys Leu Thr Val Asp Lys
        290                 295                 300

Ser Arg Trp Gln Gln Gly Asn Val Phe Ser Cys Ser Val Met His Glu
305                 310                 315                 320

Ala Leu His Asn His Tyr Thr Gln Lys Ser Leu Ser Leu Ser Pro Gly
                325                 330                 335

<210> SEQ ID NO 16
<211> LENGTH: 299
<212> TYPE: PRT
<213> ORGANISM: Artificial
<220> FEATURE:
<223> OTHER INFORMATION: IL-15R??-Sushi+-Linker 4-Knob-Fc chain

<400> SEQUENCE: 16

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Asp Pro Ala Leu Val His Gln Arg Pro Ala Pro Gly Cys Pro
65                  70                  75                  80

Pro Cys Pro Ala Pro Glu Ala Ala Gly Ala Pro Ser Val Phe Leu Phe
                85                  90                  95

Pro Pro Lys Pro Lys Asp Thr Leu Met Ile Ser Arg Thr Pro Glu Val
            100                 105                 110

Thr Cys Val Val Val Asp Val Ser His Glu Asp Pro Glu Val Lys Phe
        115                 120                 125
```

Asn Trp Tyr Val Asp Gly Val Glu Val His Asn Ala Lys Thr Lys Pro
    130                 135                 140

Arg Glu Glu Gln Tyr Asn Ser Thr Tyr Arg Val Val Ser Val Leu Thr
145                 150                 155                 160

Val Leu His Gln Asp Trp Leu Asn Gly Lys Glu Tyr Lys Cys Lys Val
                165                 170                 175

Ser Asn Lys Ala Leu Pro Ala Pro Ile Glu Lys Thr Ile Ser Lys Ala
            180                 185                 190

Lys Gly Gln Pro Arg Glu Pro Gln Val Cys Thr Leu Pro Pro Ser Arg
        195                 200                 205

Glu Glu Met Thr Lys Asn Gln Val Ser Leu Trp Cys Leu Val Lys Gly
    210                 215                 220

Phe Tyr Pro Ser Asp Ile Ala Val Glu Trp Glu Ser Asn Gly Gln Pro
225                 230                 235                 240

Glu Asn Asn Tyr Lys Thr Thr Pro Pro Val Leu Asp Ser Asp Gly Ser
                245                 250                 255

Phe Phe Leu Tyr Ser Lys Leu Thr Val Asp Lys Ser Arg Trp Gln Gln
            260                 265                 270

Gly Asn Val Phe Ser Cys Ser Val Met His Glu Ala Leu His Asn His
        275                 280                 285

Tyr Thr Gln Lys Ser Leu Ser Leu Ser Pro Gly
    290                 295

<210> SEQ ID NO 17
<211> LENGTH: 313
<212> TYPE: PRT
<213> ORGANISM: Artificial
<220> FEATURE:
<223> OTHER INFORMATION: Knob-Fc-linker 2-IL-15R??-+ chain

<400> SEQUENCE: 17

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Ser Ile Thr Cys Pro
225                 230                 235                 240

Pro Pro Met Ser Val Glu His Ala Asp Ile Trp Val Lys Ser Tyr Ser
            245                 250                 255

Leu Tyr Ser Arg Glu Arg Tyr Ile Cys Asn Ser Gly Phe Lys Arg Lys
                260                 265                 270

Ala Gly Thr Ser Ser Leu Thr Glu Cys Val Leu Asn Lys Ala Thr Asn
            275                 280                 285

Val Ala His Trp Thr Thr Pro Ser Leu Lys Cys Ile Arg Asp Pro Ala
            290                 295                 300

Leu Val His Gln Arg Pro Ala Pro Pro
305                 310

<210> SEQ ID NO 18
<211> LENGTH: 350
<212> TYPE: PRT
<213> ORGANISM: Artificial
<220> FEATURE:
<223> OTHER INFORMATION: Hole-Fc-Linker 2-IL-15 chain

<400> SEQUENCE: 18

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Ser Asn Trp Val Asn
225                 230                 235                 240

Val Ile Ser Asp Leu Lys Lys Ile Glu Asp Leu Ile Gln Ser Met His
            245                 250                 255

Ile Asp Ala Thr Leu Tyr Thr Glu Ser Asp Val His Pro Ser Cys Lys
        260                 265                 270

Val Thr Ala Met Lys Cys Phe Leu Leu Glu Leu Gln Val Ile Ser Leu
    275                 280                 285

Glu Ser Gly Asp Ala Ser Ile His Asp Thr Val Glu Asn Leu Ile Ile
290                 295                 300

Leu Ala Asn Asn Ser Leu Ser Ser Asn Gly Asn Val Thr Glu Ser Gly
305                 310                 315                 320

Cys Lys Glu Cys Glu Glu Leu Glu Glu Lys Asn Ile Lys Glu Phe Leu
                325                 330                 335

Gln Ser Phe Val His Ile Val Gln Met Phe Ile Asn Thr Ser
            340                 345                 350

<210> SEQ ID NO 19
<211> LENGTH: 350
<212> TYPE: PRT
<213> ORGANISM: Artificial
<220> FEATURE:
<223> OTHER INFORMATION: IL-15-Linker 3-Hole-Fc chain

<400> SEQUENCE: 19

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Gly Ser Gly Gly Gly Gly Ser Gly Gly Gly Gly
        115                 120                 125

Ser Cys Pro Pro Cys Pro Ala Pro Glu Ala Ala Gly Ala Pro Ser Val
130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser His Glu Asp Pro Glu
                165                 170                 175

Val Lys Phe Asn Trp Tyr Val Asp Gly Val Glu Val His Asn Ala Lys
            180                 185                 190

Thr Lys Pro Arg Glu Glu Gln Tyr Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Ala Leu Pro Ala Pro Ile Glu Lys Thr Ile
225                 230                 235                 240

Ser Lys Ala Lys Gly Gln Pro Arg Glu Pro Gln Val Tyr Thr Leu Pro
                245                 250                 255

```
Pro Cys Arg Glu Glu Met Thr Lys Asn Gln Val Ser Leu Ser Cys Ala
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Val Ser Lys Leu Thr Val Asp Lys Ser Arg
305                 310                 315                 320

Trp Gln Gln Gly Asn Val Phe Ser Cys Ser Val Met His Glu Ala Leu
                325                 330                 335

His Asn His Tyr Thr Gln Lys Ser Leu Ser Leu Ser Pro Gly
            340                 345                 350

<210> SEQ ID NO 20
<211> LENGTH: 355
<212> TYPE: PRT
<213> ORGANISM: Artificial
<220> FEATURE:
<223> OTHER INFORMATION: Fc-Linker 3-IL-15 chain

<400> SEQUENCE: 20

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Gly Ser Gly Gly Gly Gly
225                 230                 235                 240

Ser Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270
```

```
His Pro Ser Cys Lys Val Thr Ala Met Lys Cys Phe Leu Glu Leu
            275                 280                 285

Gln Val Ile Ser Leu Glu Ser Gly Asp Ala Ser Ile His Asp Thr Val
        290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
                340                 345                 350

Asn Thr Ser
        355

<210> SEQ ID NO 21
<211> LENGTH: 350
<212> TYPE: PRT
<213> ORGANISM: Artificial
<220> FEATURE:
<223> OTHER INFORMATION: IL-15-Linker 3-Fc chain

<400> SEQUENCE: 21

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser Gly Gly Gly Gly Ser Gly Gly Gly Ser Gly Gly Gly Gly
                115                 120                 125

Ser Cys Pro Pro Cys Pro Ala Pro Glu Ala Ala Gly Ala Pro Ser Val
130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser His Glu Asp Pro Glu
                165                 170                 175

Val Lys Phe Asn Trp Tyr Val Asp Gly Val Glu Val His Asn Ala Lys
                180                 185                 190

Thr Lys Pro Arg Glu Glu Gln Tyr Asn Ser Thr Tyr Arg Val Val Ser
            195                 200                 205

Val Leu Thr Val Leu His Gln Asp Trp Leu Asn Gly Lys Glu Tyr Lys
        210                 215                 220

Cys Lys Val Ser Asn Lys Ala Leu Pro Ala Pro Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Arg Asp Glu Leu Thr Lys Asn Gln Val Ser Leu Thr Cys Ala
                260                 265                 270
```

```
Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
290                 295                 300

Asp Gly Ser Phe Phe Leu Val Ser Lys Leu Thr Val Asp Lys Ser Arg
305                 310                 315                 320

Trp Gln Gln Gly Asn Val Phe Ser Cys Ser Val Met His Glu Ala Leu
                325                 330                 335

His Asn His Tyr Thr Gln Lys Ser Leu Ser Leu Ser Pro Gly
        340                 345                 350

<210> SEQ ID NO 22
<211> LENGTH: 313
<212> TYPE: PRT
<213> ORGANISM: Artificial
<220> FEATURE:
<223> OTHER INFORMATION: Knob-Fc-Linker 2-IL-15R??-Sushi+ chain

<400> SEQUENCE: 22

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Ser Ile Thr Cys Pro
225                 230                 235                 240

Pro Pro Met Ser Val Glu His Ala Asp Ile Trp Val Lys Ser Tyr Ser
                245                 250                 255

Leu Tyr Ser Arg Glu Arg Tyr Ile Cys Asn Ser Gly Phe Lys Arg Lys
            260                 265                 270

Ala Gly Thr Ser Ser Leu Thr Glu Cys Val Leu Asn Lys Ala Thr Asn
        275                 280                 285
```

```
Val Ala His Trp Thr Thr Pro Ser Leu Lys Cys Ile Arg Asp Pro Ala
            290                 295                 300

Leu Val His Gln Arg Pro Ala Pro Pro
305                 310

<210> SEQ ID NO 23
<211> LENGTH: 313
<212> TYPE: PRT
<213> ORGANISM: Artificial
<220> FEATURE:
<223> OTHER INFORMATION: Fc-Linker 2-IL-15R??-Sushi+ chain

<400> SEQUENCE: 23

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Gly Gly Gly Ser Gly Gly Gly Ser Ile Thr Cys Pro
225                 230                 235                 240

Pro Pro Met Ser Val Glu His Ala Asp Ile Trp Val Lys Ser Tyr Ser
                245                 250                 255

Leu Tyr Ser Arg Glu Arg Tyr Ile Cys Asn Ser Gly Phe Lys Arg Lys
            260                 265                 270

Ala Gly Thr Ser Ser Leu Thr Glu Cys Val Leu Asn Lys Ala Thr Asn
        275                 280                 285

Val Ala His Trp Thr Thr Pro Ser Leu Lys Cys Ile Arg Asp Pro Ala
            290                 295                 300

Leu Val His Gln Arg Pro Ala Pro Pro
305                 310

<210> SEQ ID NO 24
<211> LENGTH: 114
```

```
<212> TYPE: PRT
<213> ORGANISM: Artificial
<220> FEATURE:
<223> OTHER INFORMATION: IL-15 S58D Variant Polypeptide

<400> SEQUENCE: 24

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Asp Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 25
<211> LENGTH: 114
<212> TYPE: PRT
<213> ORGANISM: Artificial
<220> FEATURE:
<223> OTHER INFORMATION: IL-15 T62D Variant Polypeptide

<400> SEQUENCE: 25

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Asp Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 26
<211> LENGTH: 114
<212> TYPE: PRT
<213> ORGANISM: Artificial
<220> FEATURE:
<223> OTHER INFORMATION: IL-15 V63F Variant Polypeptide

<400> SEQUENCE: 26

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30
```

```
Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Phe Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 27
<211> LENGTH: 114
<212> TYPE: PRT
<213> ORGANISM: Artificial
<220> FEATURE:
<223> OTHER INFORMATION: IL-15 I67V Variant Polypeptide

<400> SEQUENCE: 27

```
Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
             20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
 50                  55                  60

Asn Leu Val Ile Leu Ala Asn Asn Ser Leu Ser Ser Asn Gly Asn Val
 65                  70                  75                  80

Thr Glu Ser Gly Cys Lys Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 28
<211> LENGTH: 114
<212> TYPE: PRT
<213> ORGANISM: Artificial
<220> FEATURE:
<223> OTHER INFORMATION: IL-15 I68F Variant Polypeptide

<400> SEQUENCE: 28

```
Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
             20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
 50                  55                  60

Asn Leu Ile Phe Leu Ala Asn Asn Ser Leu Ser Ser Asn Gly Asn Val
 65                  70                  75                  80

Thr Glu Ser Gly Cys Lys Cys Glu Glu Leu Glu Glu Lys Asn Ile
                85                  90                  95

Lys Glu Phe Leu Gln Ser Phe Val His Ile Val Gln Met Phe Ile Asn
```

<210> SEQ ID NO 29
<211> LENGTH: 114
<212> TYPE: PRT
<213> ORGANISM: Artificial
<220> FEATURE:
<223> OTHER INFORMATION: IL-15 I68K Variant Polypeptide

<400> SEQUENCE: 29

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Lys Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 30
<211> LENGTH: 114
<212> TYPE: PRT
<213> ORGANISM: Artificial
<220> FEATURE:
<223> OTHER INFORMATION: IL-15 I68D Variant Polypeptide

<400> SEQUENCE: 30

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Asp Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 31
<211> LENGTH: 114
<212> TYPE: PRT
<213> ORGANISM: Artificial
<220> FEATURE:
<223> OTHER INFORMATION: IL-15 I68H Variant Polypeptide

<400> SEQUENCE: 31

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile His Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 32
<211> LENGTH: 114
<212> TYPE: PRT
<213> ORGANISM: Artificial
<220> FEATURE:
<223> OTHER INFORMATION: IL-15 Q108A Variant Polypeptide

<400> SEQUENCE: 32

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Ala Met Phe Ile Asn
            100                 105                 110

Thr Ser

<210> SEQ ID NO 33
<211> LENGTH: 114
<212> TYPE: PRT
<213> ORGANISM: Artificial
<220> FEATURE:
<223> OTHER INFORMATION: IL-15 Q108M Variant Polypeptide

<400> SEQUENCE: 33

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Met Met Phe Ile Asn
            100                 105                 110

Thr Ser

<210> SEQ ID NO 34
<211> LENGTH: 114
<212> TYPE: PRT
<213> ORGANISM: Artificial
<220> FEATURE:
<223> OTHER INFORMATION: IL-15 Q108S Variant Polypeptide

<400> SEQUENCE: 34

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Ser Met Phe Ile Asn
            100                 105                 110

Thr Ser

<210> SEQ ID NO 35
<211> LENGTH: 114
<212> TYPE: PRT
<213> ORGANISM: Artificial
<220> FEATURE:
<223> OTHER INFORMATION: IL-15 Q108S/D30T Variant Polypeptide

<400> SEQUENCE: 35

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Thr Val His
            20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Ser Met Phe Ile Asn
            100                 105                 110

Thr Ser

<210> SEQ ID NO 36

```
<211> LENGTH: 114
<212> TYPE: PRT
<213> ORGANISM: Artificial
<220> FEATURE:
<223> OTHER INFORMATION: IL-15 Q108S/V31Y Variant Polypeptide

<400> SEQUENCE: 36

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Tyr His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Ser Met Phe Ile Asn
            100                 105                 110

Thr Ser

<210> SEQ ID NO 37
<211> LENGTH: 114
<212> TYPE: PRT
<213> ORGANISM: Artificial
<220> FEATURE:
<223> OTHER INFORMATION: IL-15 Q108S/H32E Variant Polypeptide

<400> SEQUENCE: 37

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val Glu
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Ser Met Phe Ile Asn
            100                 105                 110

Thr Ser

<210> SEQ ID NO 38
<211> LENGTH: 114
<212> TYPE: PRT
<213> ORGANISM: Artificial
<220> FEATURE:
<223> OTHER INFORMATION: IL-15 Q108S/D30T/V31Y/H32E Variant Polypeptide

<400> SEQUENCE: 38

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Thr Tyr Glu
                20                  25                  30
```

```
Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Ser Met Phe Ile Asn
            100                 105                 110

Thr Ser

<210> SEQ ID NO 39
<211> LENGTH: 110
<212> TYPE: PRT
<213> ORGANISM: Artificial
<220> FEATURE:
<223> OTHER INFORMATION: IL-15 deletion 111-114 Variant Polypeptide

<400> SEQUENCE: 39

Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe
            100                 105                 110

<210> SEQ ID NO 40
<211> LENGTH: 108
<212> TYPE: PRT
<213> ORGANISM: Artificial
<220> FEATURE:
<223> OTHER INFORMATION: IL-15 deletion 109-114 Variant Polypeptide

<400> SEQUENCE: 40

Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln
            100                 105
```

<210> SEQ ID NO 41
<211> LENGTH: 107
<212> TYPE: PRT
<213> ORGANISM: Artificial
<220> FEATURE:
<223> OTHER INFORMATION: IL-15 deletion 108-114 Variant Polypeptide

<400> SEQUENCE: 41

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val
            100                 105

<210> SEQ ID NO 42
<211> LENGTH: 104
<212> TYPE: PRT
<213> ORGANISM: Artificial
<220> FEATURE:
<223> OTHER INFORMATION: IL-15 deletion 105-114 Variant Polypeptide

<400> SEQUENCE: 42

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val
            100

<210> SEQ ID NO 43
<211> LENGTH: 116
<212> TYPE: PRT
<213> ORGANISM: Artificial
<220> FEATURE:
<223> OTHER INFORMATION: IL-15 Insertion 'GS' after N95 Variant
      Polypeptide

<400> SEQUENCE: 43

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
         35                  40                  45

Val Ile Ser Leu Glu Ser Gly Asp Ala Ser Ile His Asp Thr Val Glu
     50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Gly
             85                  90                  95

Ser Ile Lys Glu Phe Leu Gln Ser Phe Val His Ile Val Gln Met Phe
                100                 105                 110

Ile Asn Thr Ser
        115

<210> SEQ ID NO 44
<211> LENGTH: 119
<212> TYPE: PRT
<213> ORGANISM: Artificial
<220> FEATURE:
<223> OTHER INFORMATION: IL-15 Insertion 'GGSGG' after N95 Variant
      Polypeptide

<400> SEQUENCE: 44

```
Thr Glu Ser Gly Cys Lys Glu Cys Glu Glu Leu Glu Glu Lys Asn Gly
                85                  90                  95

Ser Ser Gly Ser Gly Gly Ser Ile Lys Glu Phe Leu Gln Ser Phe
            100                 105                 110

Val His Ile Val Gln Met Phe Ile Asn Thr Ser
        115                 120

<210> SEQ ID NO 46
<211> LENGTH: 355
<212> TYPE: PRT
<213> ORGANISM: Artificial
<220> FEATURE:
<223> OTHER INFORMATION: Fc-Linker 3-IL-15 S58D chain

<400> SEQUENCE: 46

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Ser Gly Gly Gly Gly
225                 230                 235                 240

Ser Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Glu Leu
        275                 280                 285

Gln Val Ile Ser Leu Glu Ser Gly Asp Ala Asp Ile His Asp Thr Val
    290                 295                 300

Glu Asn Leu Ile Ile Leu Ala Asn Asn Ser Leu Ser Ser Asn Gly Asn
305                 310                 315                 320
```

```
Val Thr Glu Ser Gly Cys Lys Glu Cys Glu Glu Leu Glu Lys Asn
                325                 330                 335

Ile Lys Glu Phe Leu Gln Ser Phe Val His Ile Val Gln Met Phe Ile
            340                 345                 350

Asn Thr Ser
        355

<210> SEQ ID NO 47
<211> LENGTH: 9
<212> TYPE: PRT
<213> ORGANISM: Artificial
<220> FEATURE:
<223> OTHER INFORMATION: Peptide Linker Sequence

<400> SEQUENCE: 47

Gly Gly Gly Gly Ser Gly Gly Gly Gly
1               5

<210> SEQ ID NO 48
<211> LENGTH: 355
<212> TYPE: PRT
<213> ORGANISM: Artificial
<220> FEATURE:
<223> OTHER INFORMATION: Hole-Fc-Linker 3-IL-15 S58D chain

<400> SEQUENCE: 48

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Gly Ser Gly Gly Gly Gly
225                 230                 235                 240

Ser Asn Trp Val Asn Val Ile Ser Asp Leu Lys Lys Ile Glu Asp Leu
```

```
                    245                 250                 255
Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Glu Leu
            275                 280                 285

Gln Val Ile Ser Leu Glu Ser Gly Asp Ala Asp Ile His Asp Thr Val
            290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser
        355

<210> SEQ ID NO 49
<211> LENGTH: 350
<212> TYPE: PRT
<213> ORGANISM: Artificial
<220> FEATURE:
<223> OTHER INFORMATION: IL-15 S58D-Linker 3-Hole-Fc chain

<400> SEQUENCE: 49

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Asp Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Ser Gly Gly Gly Ser Gly Gly Gly Gly
            115                 120                 125

Ser Cys Pro Pro Cys Pro Ala Pro Glu Ala Ala Gly Ala Pro Ser Val
        130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser His Glu Asp Pro Glu
                165                 170                 175

Val Lys Phe Asn Trp Tyr Val Asp Gly Val Glu Val His Asn Ala Lys
            180                 185                 190

Thr Lys Pro Arg Glu Glu Gln Tyr Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Ala Leu Pro Ala Pro Ile Glu Lys Thr Ile
225                 230                 235                 240

Ser Lys Ala Lys Gly Gln Pro Arg Glu Pro Gln Val Tyr Thr Leu Pro
```

```
                    245                 250                 255

Pro Cys Arg Glu Glu Met Thr Lys Asn Gln Val Ser Leu Ser Cys Ala
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Val Ser Lys Leu Thr Val Asp Lys Ser Arg
305                 310                 315                 320

Trp Gln Gln Gly Asn Val Phe Ser Cys Ser Val Met His Glu Ala Leu
                325                 330                 335

His Asn His Tyr Thr Gln Lys Ser Leu Ser Leu Ser Pro Gly
            340                 345                 350

<210> SEQ ID NO 50
<211> LENGTH: 350
<212> TYPE: PRT
<213> ORGANISM: Artificial
<220> FEATURE:
<223> OTHER INFORMATION: IL-15 S58D-Linker 3-Fc chain

<400> SEQUENCE: 50

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Asp Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Gly Ser Gly Gly Gly Gly Ser Gly Gly Gly Gly
        115                 120                 125

Ser Cys Pro Pro Cys Pro Ala Pro Glu Ala Ala Gly Ala Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser His Glu Asp Pro Glu
                165                 170                 175

Val Lys Phe Asn Trp Tyr Val Asp Gly Val Glu Val His Asn Ala Lys
            180                 185                 190

Thr Lys Pro Arg Glu Glu Gln Tyr Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Ala Leu Pro Ala Pro Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Arg Asp Glu Leu Thr Lys Asn Gln Val Ser Leu Thr Cys Ala
```

```
            260             265             270
Val Lys Gly Phe Tyr Pro Ser Asp Ile Ala Val Glu Trp Glu Ser Asn
        275                 280                 285
Gly Gln Pro Glu Asn Asn Tyr Lys Thr Thr Pro Pro Val Leu Asp Ser
            290                 295                 300
Asp Gly Ser Phe Phe Leu Val Ser Lys Leu Thr Val Asp Lys Ser Arg
305                 310                 315                 320
Trp Gln Gln Gly Asn Val Phe Ser Cys Ser Val Met His Glu Ala Leu
                325                 330                 335
His Asn His Tyr Thr Gln Lys Ser Leu Ser Leu Ser Pro Gly
            340                 345                 350

<210> SEQ ID NO 51
<211> LENGTH: 308
<212> TYPE: PRT
<213> ORGANISM: Artificial
<220> FEATURE:
<223> OTHER INFORMATION: IL-15R??-Sushi+Linker 2-Knob-Fc chain

<400> SEQUENCE: 51

Ile Thr Cys Pro Pro Pro Met Ser Val Glu His Ala Asp Ile Trp Val
1               5                   10                  15
Lys Ser Tyr Ser Leu Tyr Ser Arg Glu Arg Tyr Ile Cys Asn Ser Gly
            20                  25                  30
Phe Lys Arg Lys Ala Gly Thr Ser Ser Leu Thr Glu Cys Val Leu Asn
        35                  40                  45
Lys Ala Thr Asn Val Ala His Trp Thr Thr Pro Ser Leu Lys Cys Ile
50                  55                  60
Arg Asp Pro Ala Leu Val His Gln Arg Pro Ala Pro Pro Gly Gly Gly
65                  70                  75                  80
Gly Ser Gly Gly Gly Ser Cys Pro Pro Cys Pro Ala Pro Glu Ala Ala
                85                  90                  95
Ala Gly Ala Pro Ser Val Phe Leu Phe Pro Pro Lys Pro Lys Asp Thr
            100                 105                 110
Leu Met Ile Ser Arg Thr Pro Glu Val Thr Cys Val Val Val Asp Val
        115                 120                 125
Ser His Glu Asp Pro Glu Val Lys Phe Asn Trp Tyr Val Asp Gly Val
    130                 135                 140
Glu Val His Asn Ala Lys Thr Lys Pro Arg Glu Gln Tyr Asn Ser
145                 150                 155                 160
Thr Tyr Arg Val Val Ser Val Leu Thr Val Leu His Gln Asp Trp Leu
                165                 170                 175
Asn Gly Lys Glu Tyr Lys Cys Lys Val Ser Asn Lys Ala Leu Pro Ala
            180                 185                 190
Pro Ile Glu Lys Thr Ile Ser Lys Ala Lys Gly Gln Pro Arg Glu Pro
        195                 200                 205
Gln Val Cys Thr Leu Pro Pro Ser Arg Glu Glu Met Thr Lys Asn Gln
    210                 215                 220
Val Ser Leu Trp Cys Leu Val Lys Gly Phe Tyr Pro Ser Asp Ile Ala
225                 230                 235                 240
Val Glu Trp Glu Ser Asn Gly Gln Pro Glu Asn Asn Tyr Lys Thr Thr
                245                 250                 255
Pro Pro Val Leu Asp Ser Asp Gly Ser Phe Phe Leu Tyr Ser Lys Leu
            260                 265                 270
Thr Val Asp Lys Ser Arg Trp Gln Gln Gly Asn Val Phe Ser Cys Ser
```

```
                275                 280                 285

Val Met His Glu Ala Leu His Asn His Tyr Thr Gln Lys Ser Leu Ser
    290                 295                 300

Leu Ser Pro Gly
305

<210> SEQ ID NO 52
<211> LENGTH: 308
<212> TYPE: PRT
<213> ORGANISM: Artificial
<220> FEATURE:
<223> OTHER INFORMATION: IL-15R??-Sushi+Linker 2-Fc chain

<400> SEQUENCE: 52

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Asp Pro Ala Leu Val His Gln Arg Pro Ala Pro Pro Gly Gly Gly
65                  70                  75                  80

Gly Ser Gly Gly Gly Gly Ser Cys Pro Pro Cys Pro Ala Pro Glu Ala
                85                  90                  95

Ala Gly Ala Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

Ser His Glu Asp Pro Glu Val Lys Phe Asn Trp Tyr Val Asp Gly Val
130                 135                 140

Glu Val His Asn Ala Lys Thr Lys Pro Arg Glu Glu Gln Tyr Asn Ser
145                 150                 155                 160

Thr Tyr Arg Val Val Ser Val Leu Thr Val Leu His Gln Asp Trp Leu
                165                 170                 175

Asn Gly Lys Glu Tyr Lys Cys Lys Val Ser Asn Lys Ala Leu Pro Ala
            180                 185                 190

Pro Ile Glu Lys Thr Ile Ser Lys Ala Lys Gly Gln Pro Arg Glu Pro
        195                 200                 205

Gln Val Tyr Thr Leu Pro Pro Ser Arg Asp Glu Leu Thr Lys Asn Gln
    210                 215                 220

Val Ser Leu Thr Cys Leu Val Lys Gly Phe Tyr Pro Ser Asp Ile Ala
225                 230                 235                 240

Val Glu Trp Glu Ser Asn Gly Gln Pro Glu Asn Asn Tyr Lys Thr Thr
                245                 250                 255

Pro Pro Val Leu Asp Ser Asp Gly Ser Phe Phe Leu Tyr Ser Lys Leu
            260                 265                 270

Thr Val Asp Lys Ser Arg Trp Gln Gln Gly Asn Val Phe Ser Cys Ser
        275                 280                 285

Val Met His Glu Ala Leu His Asn His Tyr Thr Gln Lys Ser Leu Ser
    290                 295                 300

Leu Ser Pro Gly
305
```

```
<210> SEQ ID NO 53
<211> LENGTH: 355
<212> TYPE: PRT
<213> ORGANISM: Artificial
<220> FEATURE:
<223> OTHER INFORMATION: Hole-Fc-Linker 1-IL-15-S58D chain

<400> SEQUENCE: 53

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Glu Pro Lys Ser Ser Asp Lys Thr His Thr Ser Pro Pro Ser
225                 230                 235                 240

Pro Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Glu Leu
        275                 280                 285

Gln Val Ile Ser Leu Glu Ser Gly Asp Ala Asp Ile His Asp Thr Val
    290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser
        355
```

```
<210> SEQ ID NO 54
<211> LENGTH: 355
<212> TYPE: PRT
<213> ORGANISM: Artificial
<220> FEATURE:
<223> OTHER INFORMATION: Hole-Fc-Linker 3-IL-15 chain

<400> SEQUENCE: 54

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Gly Ser Gly Gly Gly Gly
225                 230                 235                 240

Ser Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Glu Leu
        275                 280                 285

Gln Val Ile Ser Leu Glu Ser Gly Asp Ala Ser Ile His Asp Thr Val
    290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser
        355
```

-continued

```
<210> SEQ ID NO 55
<211> LENGTH: 355
<212> TYPE: PRT
<213> ORGANISM: Artificial
<220> FEATURE:
<223> OTHER INFORMATION: Knob-Fc-Linker 1-IL-15 chain

<400> SEQUENCE: 55

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Glu Pro Lys Ser Ser Asp Lys Thr His Thr Ser Pro Pro Ser
225                 230                 235                 240

Pro Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Glu Leu
        275                 280                 285

Gln Val Ile Ser Leu Glu Ser Gly Asp Ala Ser Ile His Asp Thr Val
    290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser
        355
```

<210> SEQ ID NO 56
<211> LENGTH: 1131
<212> TYPE: DNA
<213> ORGANISM: Artificial
<220> FEATURE:
<223> OTHER INFORMATION: P-0313 Chain 1

<400> SEQUENCE: 56

```
atggatatgc gggtgcctgc tcagctgctg ggcctgctgc tgctgtggct gcgagggget      60
agatgtgata aaactcatac ttgtcctcca tgcccagcac ctgaggcagc aggcgcccca     120
tccgtgttcc tgtttccccc taagcccaag acacactga tgatctcccg tacgccagag     180
gtgacatgcg tggtggtgga cgtgagccac gaggacccccg aggtgaagtt taactggtac     240
gtggacggcg tggaggtgca caatgccaag acaaagccta gggaggagca gtacaattct     300
acctatcgcg tggtgagcgt gctgacagtg ctgcaccagg attggctgaa cggcaaggag     360
tataagtgca aggtgtccaa taaggccctg cctgccccaa tcgagaagac catctctaag     420
gccaagggcc agcccagaga gcctcaggtg tacacactgc ctccaagcag agacgagctg     480
accaagaacc aggtgtccct gacatgtctg gtgaagggct ctatccctc tgatatcgcc     540
gtggagtggg agagcaatgg ccagcctgag aacaattaca agaccacacc cctgtgctg     600
gacagcgatg gctccttctt tctgtattcc aagctgaccg tggataagtc cggtggcag     660
cagggcaacg tgttttcctg ctctgtgatg cacgaagcac tgcataacca ctacacccag     720
aagagcctga gcctgtcccc cggggaggc ggaggatctg gtggcggagg aagcggaggc     780
ggcggctcca actgggtgaa tgtgatcagc gacctgaaga gatcgagga tctgatccag     840
tccatgcaca tcgacgccac cctgtataca gagtctgatg tgcaccccag ctgcaaggtg     900
accgccatga gtgttttct gctggagctg caggtcatca gcctggagtc cggcgacgca     960
gacatccacg ataccgtgga gaatctgatc atcctggcca acaattccct gtctagcaac    1020
ggcaatgtga cagagtctgg ctgcaaggag tgtgaggagc tggaggagaa gaatatcaaa    1080
gagttcctgc agagtttcgt ccacatcgtc cagatgttta tcaatacctc a             1131
```

<210> SEQ ID NO 57
<211> LENGTH: 321
<212> TYPE: DNA
<213> ORGANISM: Artificial
<220> FEATURE:
<223> OTHER INFORMATION: Chain 2 of fusion proteins P-0313, P-0234,
      P-0666, and P-0668

<400> SEQUENCE: 57

```
atggctccac ggcgggctcg gggctgtcgc accctggggc tgcctgctct gctgctgctg      60
ctgctgctga ccacctgc tacacgcggc atcacctgcc cacctccaat gagcgtggag     120
cacgcagaca tctgggtgaa gtcttacagc ctgtatagcc gggagagata catctgcaac     180
tccggcttca gcggaaggc cggcaccagc tccctgacag agtgcgtgct gaacaaggcc     240
acaaatgtgg cccactggac cacaccttcc ctgaagtgca tccgggaccc cgccctggtg     300
caccagcgcc cagccccccc t                                              321
```

<210> SEQ ID NO 58
<211> LENGTH: 1131
<212> TYPE: DNA
<213> ORGANISM: Artificial
<220> FEATURE:
<223> OTHER INFORMATION: P-0234 Chain 1

<400> SEQUENCE: 58

```
atggatatgc gggtgcctgc tcagctgctg ggcctgctgc tgctgtggct gcgaggggct      60
agatgtgata aaactcatac ttgtcctcca tgcccagcac ctgaggcagc aggcgcccca     120
tccgtgttcc tgtttccccc taagcccaag acacactga tgatctcccg tacgccagag     180
gtgacatgcg tggtggtgga cgtgagccac gaggaccccg aggtgaagtt taactggtac     240
gtggacggcg tggaggtgca caatgccaag acaaagccta gggaggagca gtacaattct     300
acctatcgcg tggtgagcgt gctgacagtg ctgcaccagg attggctgaa cggcaaggag     360
tataagtgca aggtgtccaa taaggccctg cctgccccaa tcgagaagac catctctaag     420
gccaagggca gcccagaga gcctcaggtg tacacactgc ctccaagcag agacgagctg     480
accaagaacc aggtgtccct gacatgtctg gtgaagggct ctatccctc tgatatcgcc     540 gtggagtggg agagcaatgg ccagcctgag aacaattaca agaccacacc ccctgtgctg     600
gacagcgatg gctccttctt tctgtattcc aagctgaccg tggataagtc tcggtggcag     660
cagggcaacg tgttttcctg ctctgtgatg cacgaagcac tgcataacca ctacacccag     720
aagagcctga gcctgtcccc cggggaggc ggaggatctg gtggcggagg aagcggaggc     780
ggcggctcca actgggtgaa tgtgatcagc gacctgaaga gatcgagga tctgatccag     840 tccatgcaca tcgacgccac cctgtataca gagtctgatg tgcaccccag ctgcaaggtg     900
accgccatga gtgttttct gctggagctg caggtcatca gcctggagtc cggcgacgca     960
agcatccacg ataccgtgga gaatctgatc atcctggcca acaattccct gtctagcaac    1020
ggcaatgtga cagagtctgg ctgcaaggag tgtgaggagc tggaggagaa gaatatcaaa    1080
gagttcctgc agagtttcgt ccacatcgtc cagatgttta tcaataccctc a            1131
```

<210> SEQ ID NO 59
<211> LENGTH: 1131
<212> TYPE: DNA
<213> ORGANISM: Artificial
<220> FEATURE:
<223> OTHER INFORMATION: P-0666 Chain 1

<400> SEQUENCE: 59

```
atggatatgc gagtgcctgc tcagctgctg ggcctgctgc tgctgtggct gcgggggggct     60 agatgcgata aaactcatac ctgtcctcca tgcccagcac ctgaggcagc aggcgcccca    120
tccgtgttcc tgtttccccc taagcccaag acaccctga tgatctctcg tacgcccgag    180
gtgacatgcg tggtggtgga cgtgagccac gaggaccccg aggtgaagtt caactggtac    240
gtggatggcg tggaggtgca caatgccaag acaaagcctc gggaggagca gtacaactcc    300
acctatagag tggtgtctgt gctgacagtg ctgcaccagg actggctgaa cggcaaggag    360
tacaagtgca aggtgtccaa taaggccctg ccagccccca tcgagaagac catcagcaag    420
gccaagggcc agcctaggga gccacaggtg tataccctgc caccctgccg cgaggagatg    480
acaaagaacc aggtgtccct gtcttgtgcc gtgaagggct ctaccccttc tgacatcgcc    540
gtggagtggg agagcaatgg ccagccagag aacaattata agaccacacc tccagtgctg    600
gactctgatg gcagcttctt tctggtgagc aagctgaccg tggataagtc caggtggcag    660
cagggcaacg tgtttagctg ttccgtgatg cacgaggccc tgcacaatca ctacacacag    720
aagtctctga gcctgtcccc cggggaggc ggaggatctg gtggcggagg aagcggaggc    780
ggcggctcca actgggtgaa tgtgatcagc gacctgaaga gatcgagga tctgatccag    840 tccatgcaca tcgacgccac cctgtataca gagtctgatg tgcaccccag ctgcaaggtg    900
```

| | |
|---|---|
| accgccatga agtgttttct gctggagctg caggtcatca gcctggagtc cggcgacgca | 960 |
| gacatccacg ataccgtgga gaatctgatc atcctggcca acaattccct gtctagcaac | 1020 |
| ggcaatgtga cagagtctgg ctgcaaggag tgtgaggagc tggaggagaa gaatatcaaa | 1080 |
| gagttcctgc agagtttcgt ccacatcgtc cagatgttta tcaataccctc a | 1131 |

```
<210> SEQ ID NO 60
<211> LENGTH: 744
<212> TYPE: DNA
<213> ORGANISM: Artificial
<220> FEATURE:
<223> OTHER INFORMATION: P-0666 Chain 3

<400> SEQUENCE: 60
```

| | |
|---|---|
| atggatatgc gggtgcctgc tcagctgctg ggcctgctgc tgctgtggct gcgaggggct | 60 |
| agatgtgata aaactcatac ttgtcctcca tgcccagcac ctgaggcagc aggcgcccca | 120 |
| tccgtgttcc tgtttccccc taagcccaag gacacactga tgatctcccg tacgccagag | 180 |
| gtgacatgcg tggtggtgga cgtgtctcac gaggacccccg aggtgaagtt caactggtac | 240 |
| gtggatggcg tggaggtgca caatgccaag accaagccca gggaggagca gtacaacagc | 300 |
| acctatcgcg tggtgtccgt gctgacagtg ctgcaccagg actggctgaa cggcaaggag | 360 |
| tataagtgca aggtgtccaa taaggccctg ccagccccca tcgagaagac catcagcaag | 420 |
| gcaaagggac agcctcggga gccacaggtg tgcaccctgc caccctctag agaggagatg | 480 |
| acaaagaacc aggtgagcct gtggtgtctg gtgaagggct tctacccttc gacatcgcc | 540 |
| gtggagtggg agtctaatgg ccagccagag aacaattaca agaccacacc tccagtgctg | 600 |
| gactctgatg gcagcttctt tctgtattct aagctgaccg tggataagag caggtggcag | 660 |
| cagggcaacg tgttttcctg ctctgtgatg cacgaggccc tgcacaatca ctacacacag | 720 |
| aagagcctgt ccctgtctcc cggg | 744 |

```
<210> SEQ ID NO 61
<211> LENGTH: 1110
<212> TYPE: DNA
<213> ORGANISM: Artificial
<220> FEATURE:
<223> OTHER INFORMATION: P-0668 Chain 1

<400> SEQUENCE: 61
```

| | |
|---|---|
| atgtatcgga tgcagctgct gtcttgtatc gctctgtcac tggctctggt cactaattct | 60 |
| aactgggtca atgtcatttc tgatctgaag aagatcgagg acctgatcca gagcatgcac | 120 |
| atcgatgcca ccctgtacac agagtccgac gtgcacccat cttgcaaggt gaccgcaatg | 180 |
| aagtgtttcc tgctggagct gcaggtcatc agcctggaga gcggcgacgc agatatccac | 240 |
| gataccgtgg agaacctgat catcctggca acaattccc tgagctccaa cggaaatgtg | 300 |
| acagagtctg gatgcaagga gtgtgaggag ctggaggaga gaacatcaa ggagttcctg | 360 |
| cagtcttttg tgcacatcgt gcagatgttc atcaatacat ccgcggcgg cggctccggc | 420 |
| ggcggcggct ctggcggcgg cggcagctgc ccccttgtc cagcccccga ggccgctggg | 480 |
| gcaccaagcg tgttcctgtt ccctccaaaa ccaaaagata tctctgatga tagccgtacg | 540 |
| ccagaggtga catgcgtggt ggtggacgtg agccacgagg accccgaggt gaagtttaac | 600 |
| tggtacgtgg acggcgtgga ggtgcacaat gccaagacaa agcctaggga ggagcagtac | 660 |
| aattctacct atcgcgtggt gagcgtgctg acagtgctgc accaggattg gctgaacggc | 720 |
| aaggagtata agtgcaaggt gtccaataag gccctgcctg ccccaatcga gaagaccatc | 780 |

```
tctaaggcca agggccagcc cagagagcct caggtgtaca cactgcctcc aagcagagac    840
gagctgacca agaaccaggt gtccctgaca tgtctggtga agggcttcta tccctctgat    900
atcgccgtgg agtgggagag caatggccag cctgagaaca attacaagac cacaccccct    960
gtgctggaca cgcatggctc cttctttctg tattccaagc tgaccgtgga taagtctcgg   1020
tggcagcagg gcaacgtgtt ttcctgctct gtgatgcacg aagcactgca taaccactac   1080
acccagaaga gcctgagcct gtcccccggg                                     1110

<210> SEQ ID NO 62
<211> LENGTH: 1005
<212> TYPE: DNA
<213> ORGANISM: Artificial
<220> FEATURE:
<223> OTHER INFORMATION: P-0314 Chain 1

<400> SEQUENCE: 62
atggatatgc gggtgcctgc tcagctgctg ggcctgctgc tgctgtggct gcgagggget     60 agatgtgata aaactcatac ttgtcctcca tgcccagcac ctgaggcagc aggcgcccca    120
tccgtgttcc tgtttccccc taagcccaag gacacactga tgatctcccg tacgccagag    180
gtgacatgcg tggtggtgga cgtgagccac gaggaccccg aggtgaagtt taactggtac    240
gtggacggcg tggaggtgca caatgccaag acaaagccta gggaggagca gtacaattct    300
acctatcgcg tggtgagcgt gctgacagtg ctgcaccagg attggctgaa cggcaaggag    360
tataagtgca aggtgtccaa taaggccctg cctgccccaa tcgagaagac catctctaag    420
gccaagggcc agcccagaga gcctcaggtg tacacactgc ctccaagcag agacgagctg    480
accaagaacc aggtgtccct gacatgtctg gtgaagggct tctatccctc tgatatcgcc    540
gtggagtggg agagcaatgg ccagcctgag aacaattaca gaccacacc cctgtgctg    600 gacagcgatg gctccttctt tctgtattcc aagctgaccg tggataagtc tcggtggcag    660
cagggcaacg tgttttcctg ctctgtgatg cacgaagcac tgcataacca ctacacccag    720
aagagcctga gcctgtcccc cggggggcgg cggcggcag cgaggcggcgg ctccatcacc    780 tgtccacccc ctatgagcgt ggagcacgcc gatatctggg tgaagagcta ctccctgtat    840
agccgggaga gatatatctg caattccggc tttaagcgca aggccggcac ctctagcctg    900
acagagtgcg tgctgaacaa ggccaccaat gtggcccact ggacaacccc aagcctgaag    960
tgtattagag accctgccct ggtgcatcag cggcctgctc cccca                   1005

<210> SEQ ID NO 63
<211> LENGTH: 402
<212> TYPE: DNA
<213> ORGANISM: Artificial
<220> FEATURE:
<223> OTHER INFORMATION: P-0314 Chain 2

<400> SEQUENCE: 63
atgtaccgga tgcagctgct gtcctgcatc gccctgtctc tggccctggt gaccaactct     60
aattgggtga acgtgatcag cgacctgaag aagatcgagg atctgatcca gtctatgcac    120
atcgacgcca ccctgtatac agagagcgat gtgcaccccc ctgcaaggt gacagccatg    180 aagtgtttcc tgctggagct gcaggtcatc agcctggaga gcggcgacgc agacatccac    240
gataccgtgg agaacctgat catcctggcc aataactccc tgagctccaa cggcaatgtg    300
acagagtctg gctgcaagga gtgtgaggag ctggaggaga agaacatcaa ggagttcctg    360
```
cagagctttg tgcacatcgt gcagatgttt atcaatacct cc                402

<210> SEQ ID NO 64
<211> LENGTH: 296
<212> TYPE: PRT
<213> ORGANISM: Artificial
<220> FEATURE:
<223> OTHER INFORMATION: Benchmark Chain1

<400> SEQUENCE: 64

```
Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Glu Pro Lys Ser Cys Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
        115                 120                 125

Val Asp Gly Val Glu Val His Asn Ala Lys Thr Lys Pro Arg Glu Glu
    130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Asp Glu Leu
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly
    290                 295
```

<210> SEQ ID NO 65
<211> LENGTH: 114
<212> TYPE: PRT
<213> ORGANISM: Artificial
<220> FEATURE:
<223> OTHER INFORMATION: Benchmark Chain 2

<400> SEQUENCE: 65

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35              40                  45

Val Ile Ser Leu Glu Ser Gly Asp Ala Ser Ile His Asp Thr Val Glu
    50              55                  60

Asn Leu Ile Ile Leu Ala Asn Asp Ser Leu Ser Ser Asn Gly Asn Val
65                  70              75                      80

Thr Glu Ser Gly Cys Lys Glu Cys Glu Glu Leu Glu Glu Lys Asn Ile
                85              90                  95

Lys Glu Phe Leu Gln Ser Phe Val His Ile Val Gln Met Phe Ile Asn
            100             105                 110

Thr Ser
```